(12) United States Patent
Shemesh et al.

(10) Patent No.: US 9,428,586 B2
(45) Date of Patent: Aug. 30, 2016

(54) HEPARANASE SPLICE VARIANT

(75) Inventors: Ronen Shemesh, Modiin (IL); Michal Ayalon-Soffer, Ramat Hasharon (IL); Zurit Levine, Herzliya (IL); Sergey Nemzer, Raanana (IL); Tomer Zekharya, Shimshon (IL); Gad S. Cojocaru, Ramat-HaSharon (IL); Uri Barash, Kiryat Ata (IL); Neta Ilan, Herzliya (IL); Israel Vlodavsky, Mevaseret Zion (IL); Iris Hecht, Tel-Aviv (IL)

(73) Assignee: COMPUGEN LTD, Holon (IL)

( * ) Notice: Subject to any disclaimer, the term of this patent is extended or adjusted under 35 U.S.C. 154(b) by 967 days.

(21) Appl. No.: 13/512,921

(22) PCT Filed: Nov. 30, 2010

(86) PCT No.: PCT/IB2010/055488
§ 371 (c)(1),
(2), (4) Date: Aug. 13, 2012

(87) PCT Pub. No.: WO2011/067711
PCT Pub. Date: Jun. 9, 2011

(65) Prior Publication Data
US 2012/0301475 A1    Nov. 29, 2012

(51) Int. Cl.
| | |
|---|---|
| A61K 39/395 | (2006.01) |
| C07K 16/30 | (2006.01) |
| C07K 16/40 | (2006.01) |
| C12N 15/113 | (2010.01) |
| C12N 9/24 | (2006.01) |

(52) U.S. Cl.
CPC .............. *C07K 16/30* (2013.01); *C07K 16/40* (2013.01); *C12N 9/2402* (2013.01); *C12N 15/1137* (2013.01); *C12Y 302/01166* (2013.01); *C12N 2310/11* (2013.01); *C12N 2310/12* (2013.01); *C12N 2310/14* (2013.01)

(58) Field of Classification Search
None
See application file for complete search history.

(56) References Cited

U.S. PATENT DOCUMENTS

| 6,562,950 | B2 * | 5/2003 | Peretz | C07K 16/40 530/388.26 |
| 7,049,407 | B2 * | 5/2006 | Pecker | A61M 15/009 435/69.1 |
| 2004/0170630 | A1 * | 9/2004 | Huang | A01K 67/0278 424/146.1 |
| 2004/0170631 | A1 * | 9/2004 | Yacoby-Zeevi | C07K 16/40 424/146.1 |
| 2004/0213789 | A1 * | 10/2004 | Yacoby-Zeevi et al. .. | 424/146.1 |
| 2006/0269552 | A1 * | 11/2006 | Yacoby-Zeevi | C07K 16/40 424/146.1 |
| 2010/0233154 | A1 * | 9/2010 | Elvin | C07K 16/40 424/130.1 |

FOREIGN PATENT DOCUMENTS

| WO | 2005118808 A1 | 12/2005 |
| WO | 2007034480 A2 | 3/2007 |

OTHER PUBLICATIONS

Pomes, A., Int Arch Allergy Immunol. 2010;152(1):1-11. doi: 10.1159/000260078. Epub Nov. 26, 2009.*
PCT search report and written opinion for corresponding PCT Application No. PCT/IB2010/055488, mailed on Feb. 14, 2012.
Zhang et al, Cancer Biology and Therapy, Landes Bioscience, vol. 6, 2007, pp. 587-595.
Nasser, BBRC, Academic Press, vol. 354, 2007, pp. 33-38.
Sato et al, Cell Biochemistry and Function, vol. 26, 2008, pp. 676-683.
Shirley et al, Cancer Science, vol. 98, 2007, pp. 844-849.
Fux et al, Trends in Biochemical Sciences, vol. 34, 2009, pp. 511-519.
Cohen-Kaplan et al, Cancer Research, vol. 68, 2008, pp. 10077-10085.
Ilan et al, International Journal of Biochemistry and Cell Biology, vol. 38, 2006, pp. 2018-2039.
Barash et al, FASEB Journal, vol. 24, 2010, pp. 1239-1248.
Barash et al, FEBS Journal, vol. 277, 2010, pp. 3890-3903.

* cited by examiner

*Primary Examiner* — Michael Szperka
(74) *Attorney, Agent, or Firm* — Graeser Associates International Inc; Dvorah Graeser

(57) ABSTRACT

The present invention, in at least some aspects, is of splice variants of heparanase, as well as diagnostic kits and methods of use, and therapeutic agents and methods of use based thereon, and antibodies specifically binding thereof.

3 Claims, 21 Drawing Sheets

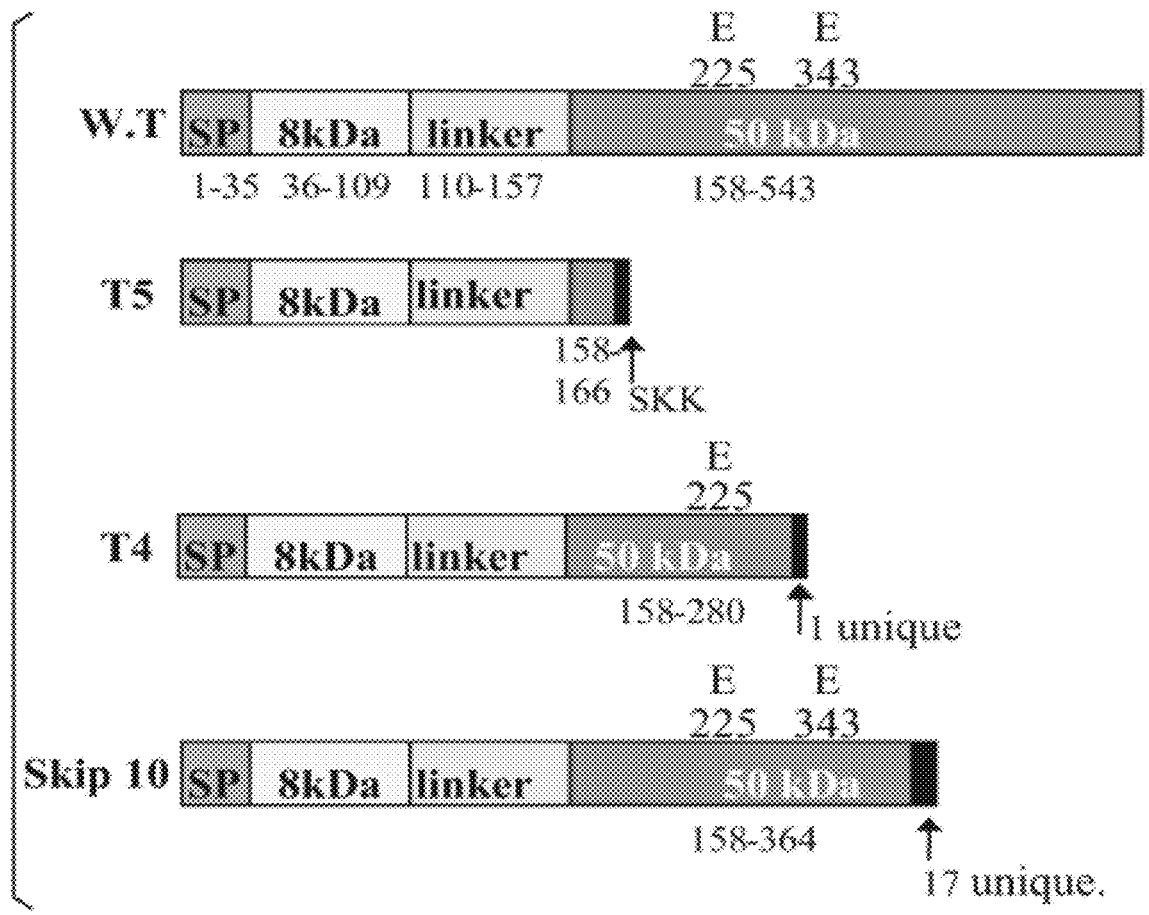

```
T5  CAGCGCTGCTCCCCGGGCGCTCCTCCCCGGGCGCTCCTCCCCAGGCCTCCCGGGCGCTTG 60
HPA CAGCGCTGCTCCCCGGGCGCTCCTCCCCGGGCGCTCCTCCCCAGGCCTCCCGGGCGCTTG 60
    ************************************************************

T5  GATCCCGGCCATCTCCGCACCCTTCAAGTGGGTGTGGGTGATTTCCTGGCGGGGGGAGCA 120
HPA GATCCCGGCCATCTCCGCACCCTTCAAGTGGGTGTGGGTGATTTCCTGGCGGGGGGAGCA 120
    ************************************************************

T5  GCCAGGTGAGCCCAAGATGCTGCTGCGCTCGAAGCCTGCGCTGCCGCCGCCGCTGATGCT 180
HPA GCCAGGTGAGCCCAAGATGCTGCTGCGCTCGAAGCCTGCGCTGCCGCCGCCGCTGATGCT 180
    ************************************************************

T5  GCTGCTCCTGGGGCCGCTGGGTCCCCTCTCCCCTGGCGCCCTGCCCGACCTGCGCAAGC 240
HPA GCTGCTCCTGGGGCCGCTGGGTCCCCTCTCCCCTGGCGCCCTGCCCGACCTGCGCAAGC 240
    ************************************************************

T5  ACAGGACGTCGTGGACCTGGACTTCTTCACCCAGGAGCCGCTGCACCTGGTGAGCCCTC 300
HPA ACAGGACGTCGTGGACCTGGACTTCTTCACCCAGGAGCCGCTGCACCTGGTGAGCCCTC 300
    ************************************************************

T5  GTTCCTGTCCGTCACCATTGACGCCAACCTGGCCACGGACCCGCGGTTCCTCATCCTCCT 360
HPA GTTCCTGTCCGTCACCATTGACGCCAACCTGGCCACGGACCCGCGGTTCCTCATCCTCCT 360
    ************************************************************

T5  GGGTTCTCCAAAGCTTCGTACCTTGGCCAGAGGCTTGTCTCCTGCGTACCTGAGGTTTGG 420
HPA GGGTTCTCCAAAGCTTCGTACCTTGGCCAGAGGCTTGTCTCCTGCGTACCTGAGGTTTGG 420
    ************************************************************

T5  TGGCACCAAGACAGACTTCCTAATTTTCGATCCCAAGAAGGAATCAACCTTTGAAGAGAG 480
HPA TGGCACCAAGACAGACTTCCTAATTTTCGATCCCAAGAAGGAATCAACCTTTGAAGAGAG 480
    ************************************************************

T5  AAGTTACTGGCAATCTCAAGTCAACCAGGATATTTGCAAATATGGATCCATCCCTCCTGA 540
HPA AAGTTACTGGCAATCTCAAGTCAACCAGGATATTTGCAAATATGGATCCATCCCTCCTGA 540
    ************************************************************

T5  TGTGGAGGAGAAGTTACGGTTGGAATGGCCCTACCAGGAGCAATTGCTACTCCGAGAACA 600
HPA TGTGGAGGAGAAGTTACGGTTGGAATGGCCCTACCAGGAGCAATTGCTACTCCGAGAACA 600
    ************************************************************

T5  CTACCAGAAAAAGTTCAAGAACAGCACCTACTCAAGTAAGAAATGAAAGGCACCCTAGAG 660
HPA CTACCAGAAAAAGTTCAAGAACAGCACCTACTCAAGAAGCTCTGTAGATGTGCTATACAC 660
    ************************************  *    *   *  * **  *

T5  ATGTTCCAGCC-CCAAAGAT----ATTTGAA---TAGGTTGGACTCGGGCACCAATCTAGC 713
HPA TTTTGCAAACTGCTCAGGACTGGACTTGATCTTTGGCCTAAATGCGTTATTAAGAACAGG 720
    * *** **  *   ** **    *  ****   **  *  *   **  *   *  * ***

T5  AAGTC--CTACGGAAGTTGTATAAAGCTGAA--AATACTGAAGCATTTCCCAAATGGGAA 769
HPA AGATTTGCAGTGGAACAGTTCTAATGCTCAGTTGCTCCTGGACTACTGCTCTTCCAAGGG 780
    *  *    *   **** ***  ** ***  *  *  * ** ****   * *    *

T5  ATCCTAAACT--------------------------------------------- 779
HPA GTATAACATTTCTTGGGAACTAGGCAATGAACCTAACAGTTTCCTTAAGAAGGCTGATAT 840
    ** * *
```

FIG. 1C

```
      1     2     3    4    5    6   7    8    9    10   11   12   13     14
WT [ 105 ][ 258 ][ 146 ][ 126 ][ 174 ][ 169 ][ 48 ][ 94 ][ 107 ][ 115 ][ 119 ][ 147 ][ 449 ][  1649  ]
      1     2     3    4
T5 [ 105 ][ 258 ][ 146 ][ 270 ]  (+144 bp of intron 5)
```

FIG. 1D

```
N3024_T5    1 MLLRSKPALPPPLMLLLLGPLGPLSPGALPRPAQAQDVVDLDFFTQEPLHLVSPSFLSVT 60
              ||||||||||||||||||||||||||||||||||||||||||||||||||||||||||||
HPSE_HUMAN  1 MLLRSKPALPPPLMLLLLGPLGPLSPGALPRPAQAQDVVDLDFFTQEPLHLVSPSFLSVT 60

N3024_T5   61 IDANLATDPRFLILLGSPKLRTLARGLSPAYLRFGGTKTDFLIFDPKKESTFEERSYWQS 120
              ||||||||||||||||||||||||||||||||||||||||||||||||||||||||||||
HPSE_HUMAN 61 IDANLATDPRFLILLGSPKLRTLARGLSPAYLRFGGTKTDFLIFDPKKESTFEERSYWQS 120

N3024_T5  121 QVNQDICKYGSIPPDVEEKLRLEWPYQEQLLLREHYQKKFKNSTYSRS.......... 169
              |||||||||||||||||||||||||||||||||||||||||||||||
HPSE_HUMAN 121 QVNQDICKYGSIPPDVEEKLRLEWPYQEQLLLREHYQKKFKNSTYS...RSVDVLYTFA 177

N3024_T5       .............................................................
HPSE_HUMAN 178 NCSGLDLIFGLNALLRTADLQWNSSNAQLLLDYCSSKGYNISWELGNEPNSFLKKADIFI 237

N3024_T5       .............................................................
HPSE_HUMAN 238 NGSQLGEDFIQLHKLLRKSTFKNAKLYGPDVGQPRRKTAKMLKSFLKAGGEVIDSVTWHH 297

N3024_T5       .............................................................
HPSE_HUMAN 298 YYLNGRTATREDFLNPDVLDTFISSVQKVFQVVESTRPGKKVWLGETSSAYGGGRPLLSD 357

N3024_T5       .............................................................
HPSE_HUMAN 358 TFAAGFMWLDKLGLSARMGIEVVMRQVFFGAGNYHLVDENFDPLPDYWLSLLFKKLVGTK 417

N3024_T5       .............................................................
HPSE_HUMAN 418 VLMASVQGSKRRKLRVYLHCTNTDNPRYKEGDLTLYAINLHNVTKYLRLPYPFSNKQVDK 477

N3024_T5       .............................................................
HPSE_HUMAN 478 YLLRPLGPHGLLSKSVQLNGLTLKMVDDQTLPPLMEKPLRPGSSLGLPAFSYSFFVIRNA 537

N3024_T5       ......
HPSE_HUMAN 538 KVAACI                                                      543
```

FIG. 1E

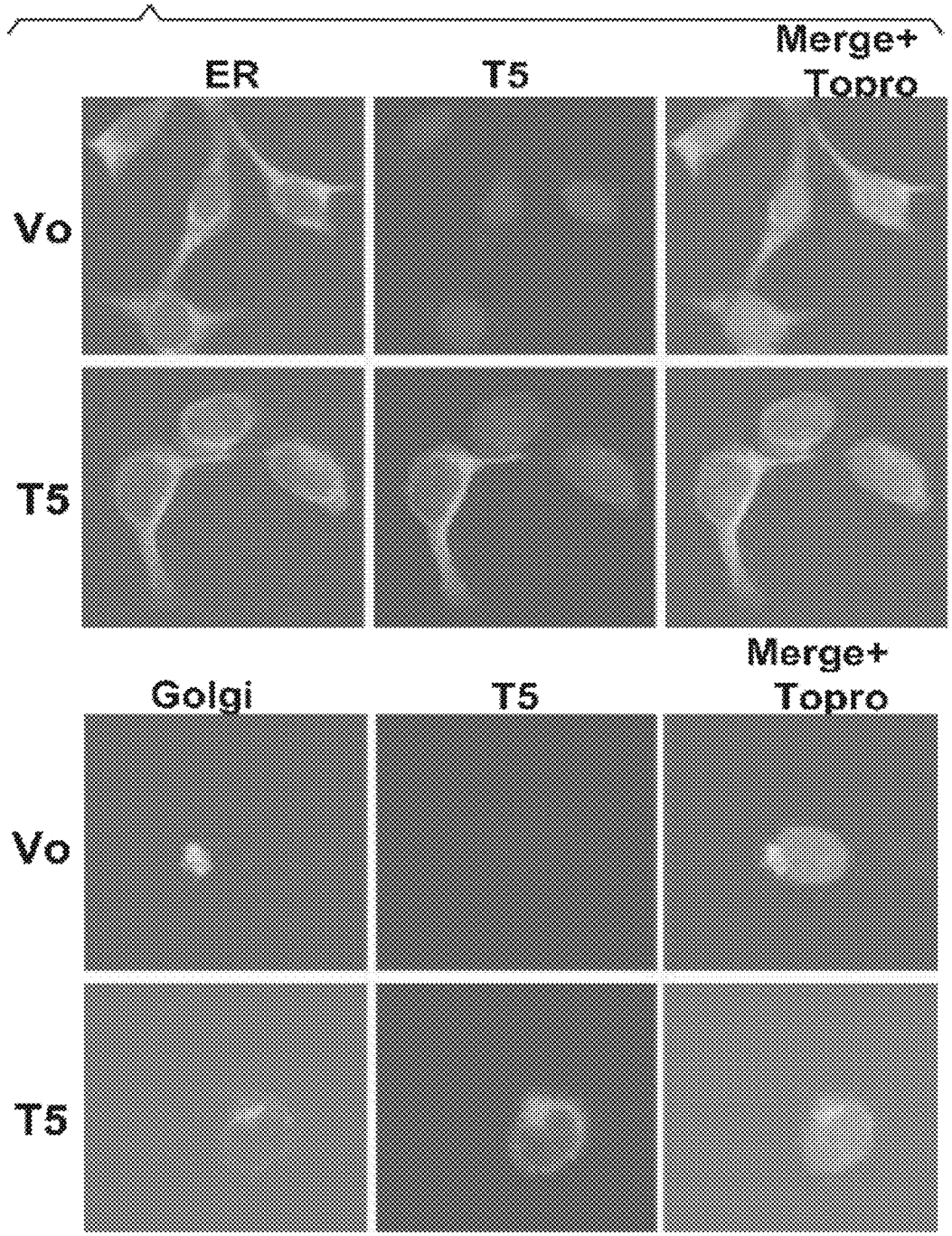

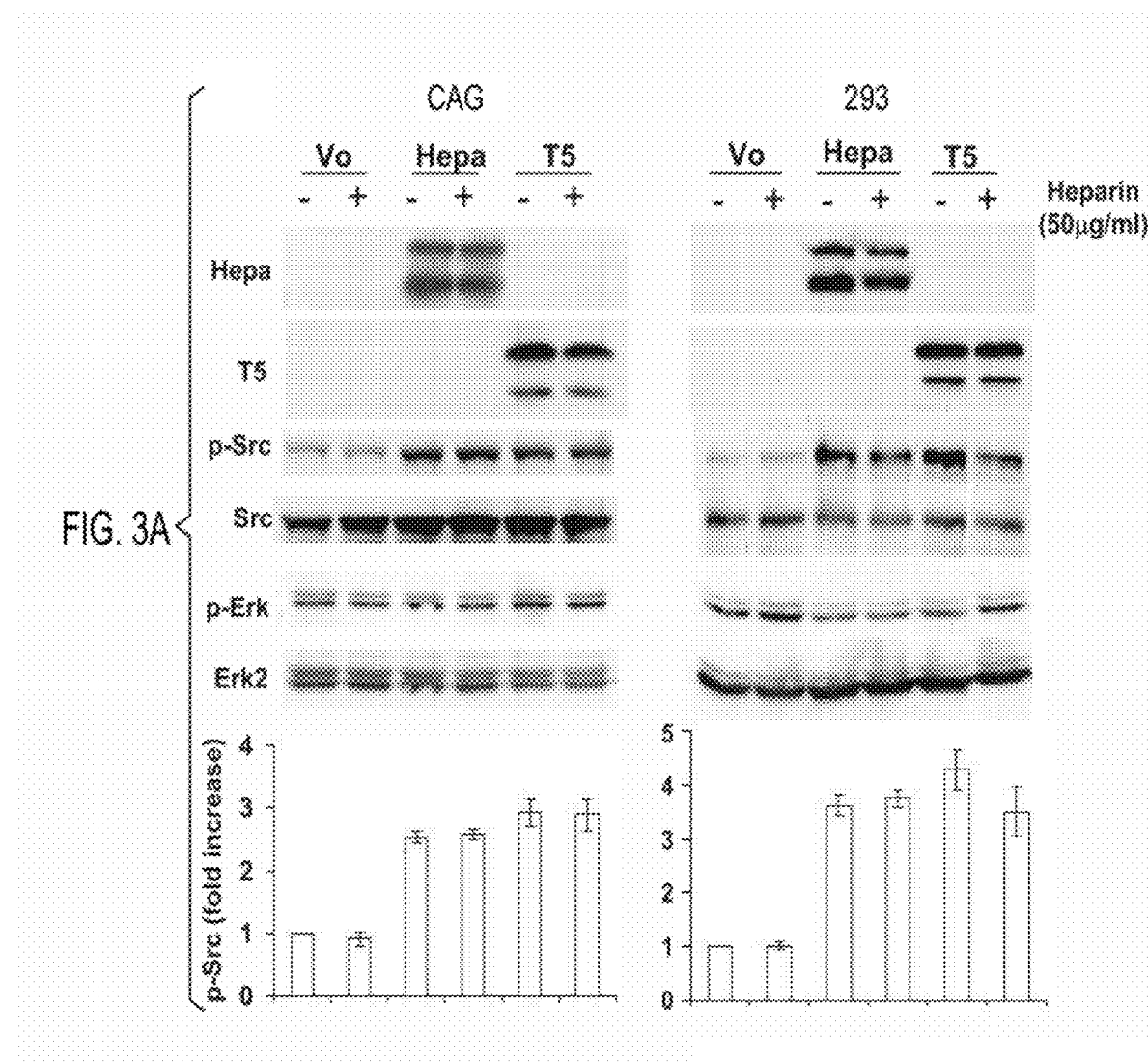

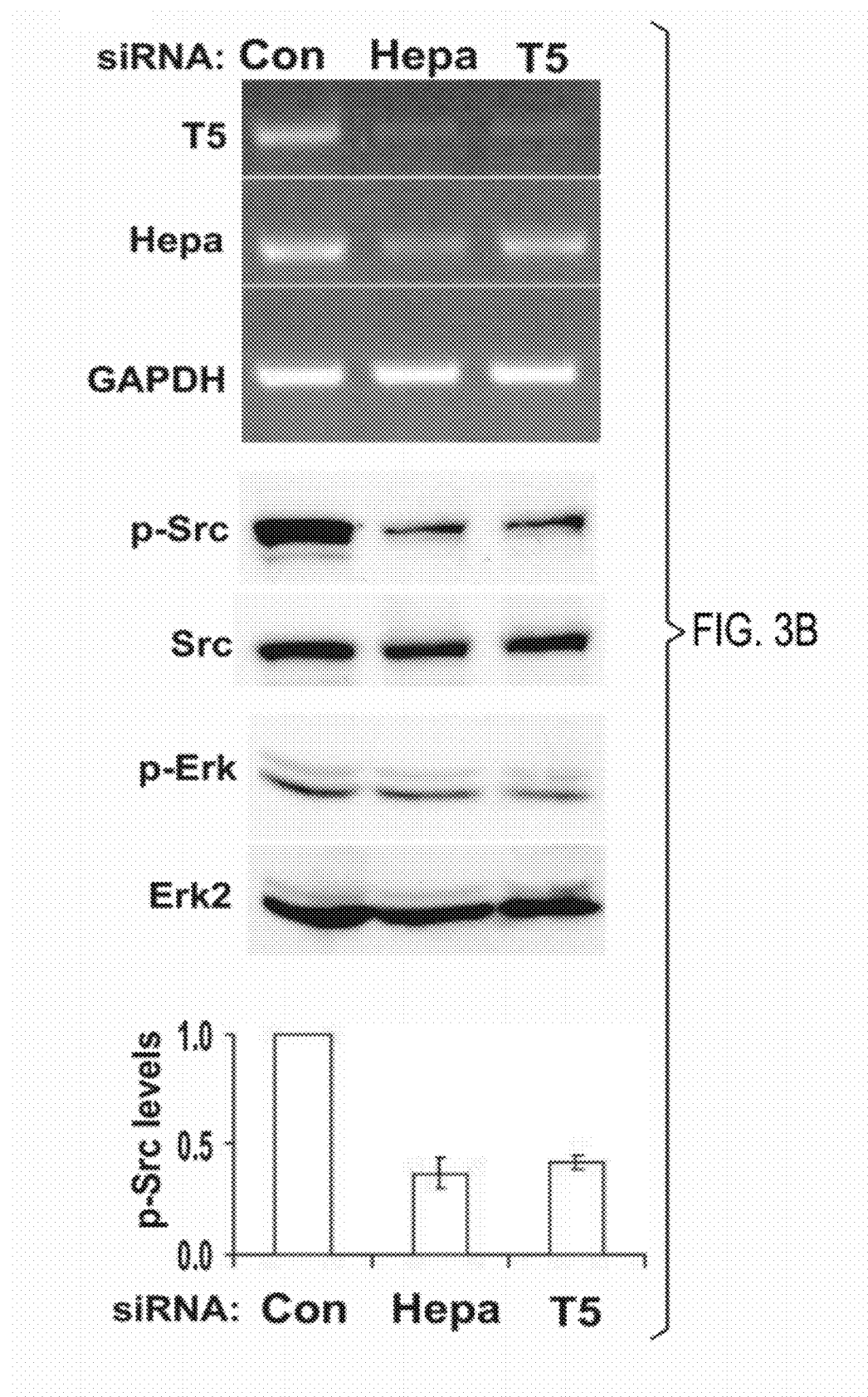

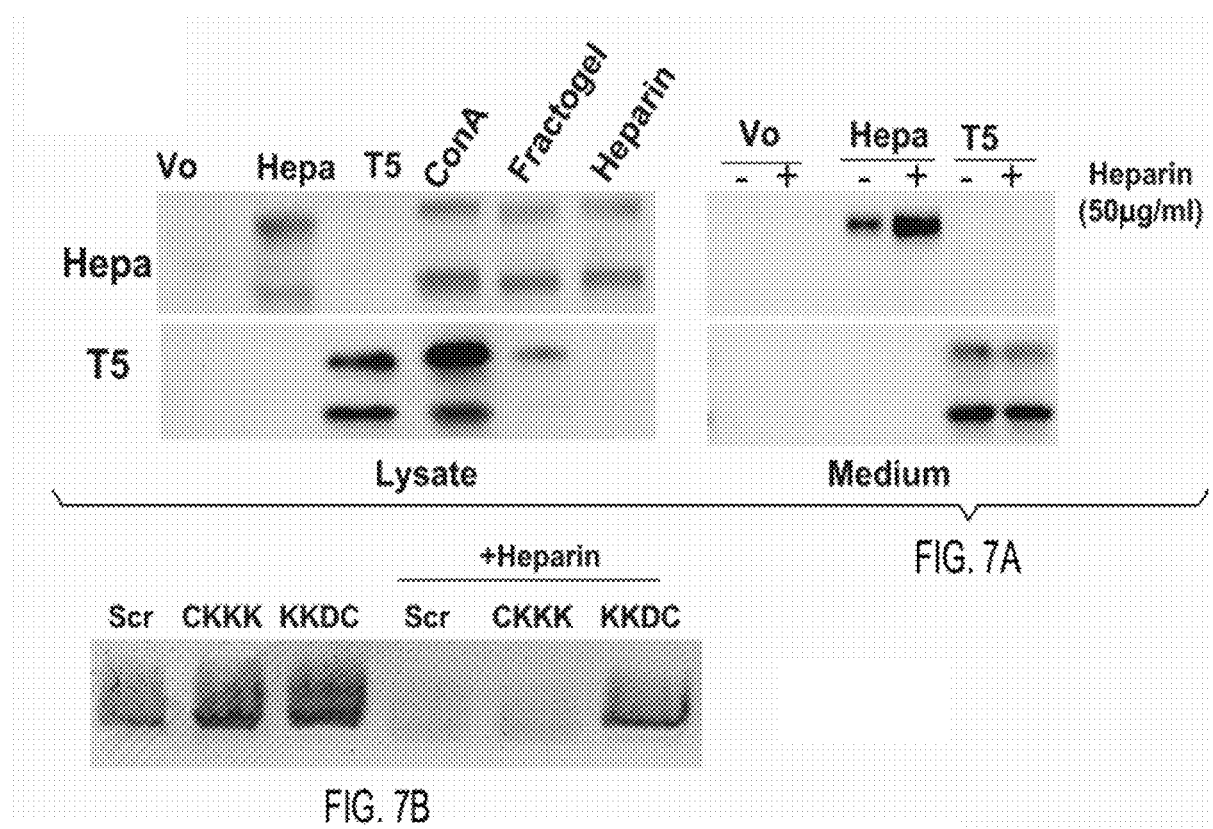

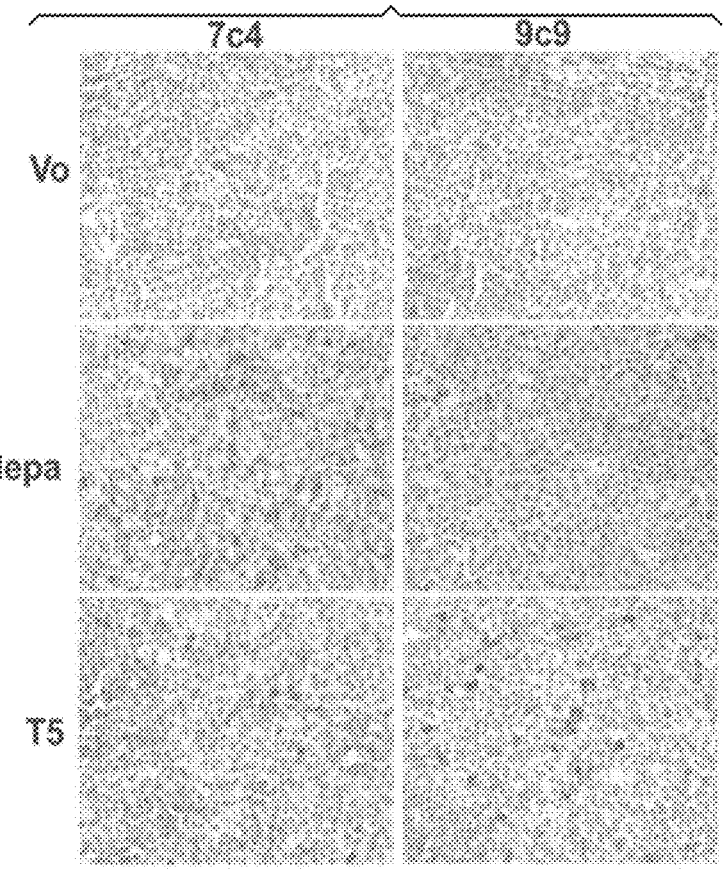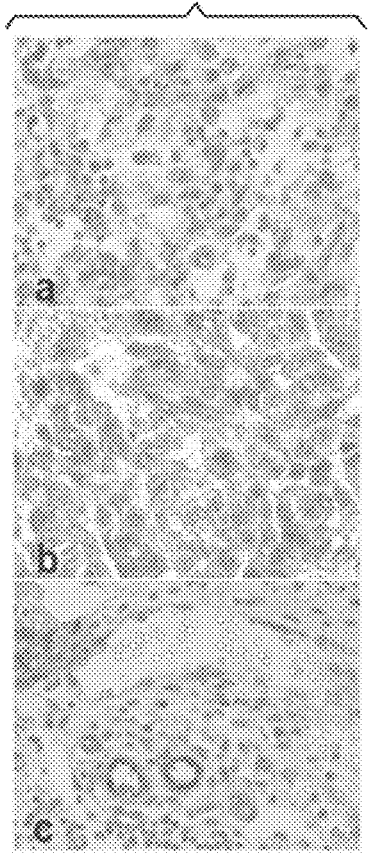

SEQUENCE LISTING

<160> NUMBER OF SEQ ID NOS: 23

<210> SEQ ID NO 1
<211> LENGTH: 169
<212> TYPE: PRT
<213> ORGANISM: Homo sapiens

<400> SEQUENCE: 1

Met Leu Leu Arg Ser Lys Pro Ala Leu Pro Pro Pro Leu Met Leu Leu
1               5                   10                  15

Leu Leu Gly Pro Leu Gly Pro Leu Ser Pro Gly Ala Leu Pro Arg Pro
            20                  25                  30

Ala Gln Ala Gln Asp Val Val Asp Leu Asp Phe Phe Thr Gln Glu Pro
        35                  40                  45

Leu His Leu Val Ser Pro Ser Phe Leu Ser Val Thr Ile Asp Ala Asn
    50                  55                  60

Leu Ala Thr Asp Pro Arg Phe Leu Ile Leu Leu Gly Ser Pro Lys Leu
65                  70                  75                  80

Arg Thr Leu Ala Arg Gly Leu Ser Pro Ala Tyr Leu Arg Phe Gly Gly
                85                  90                  95

Thr Lys Thr Asp Phe Leu Ile Phe Asp Pro Lys Lys Glu Ser Thr Phe
            100                 105                 110

Glu Glu Arg Ser Tyr Trp Gln Ser Gln Val Asn Gln Asp Ile Cys Lys
        115                 120                 125

Tyr Gly Ser Ile Pro Pro Asp Val Glu Glu Lys Leu Arg Leu Glu Trp
    130                 135                 140

Pro Tyr Gln Glu Gln Leu Leu Leu Arg Glu His Tyr Gln Lys Lys Phe
145                 150                 155                 160

Lys Asn Ser Thr Tyr Ser Ser Lys Lys
            165

<210> SEQ ID NO 2
<211> LENGTH: 780
<212> TYPE: DNA
<213> ORGANISM: Homo sapiens

<400> SEQUENCE: 2

```
ccagcgctgc tccccgggcg ctcctccccg ggcgctcctc cccaggcctc ccgggcgctt      60
ggatcccggc catctccgca cccttcaagt gggtgtgggt gatttcctgg cgggggggagc    120
agccaggtga gcccaagatg ctgctgcgct cgaagcctgc gctgccgccg ccgctgatgc    180
tgctgctcct ggggccgctg gtcccctct  ccctggcgc cctgccccga cctgcgcaag    240
cacaggacgt cgtggacctg gacttcttca cccaggagcc gctgcacctg gtgagcccct    300
cgttcctgtc cgtcaccatt gacgccaacc tggccacgga cccgcggttc ctcatcctcc    360
tgggttctcc aaagcttcgt accttggcca gaggcttgtc tcctgcgtac ctgaggtttg    420
gtggcaccaa gacagacttc ctaattttcg atcccaagaa ggaatcaacc tttgaagaga    480
gaagttactg gcaatctcaa gtcaaccagg atatttgcaa atatggatcc atccctcctg    540
atgtggagga gaagttacgg ttggaatggc cctaccagga gcaattgcta ctccgagaac    600
actaccagaa aaagttcaag aacagcacct actcaagtaa gaatgaaag gcaccctaga    660
gatgttccag ccccaaagat atttgaatag gttggactcg ggcaccaatc tagcaagtcc    720
tacggaagtt gtataaagct gaaaatactg aagcatttcc caaatgggaa atcctaaact    780
```

<210> SEQ ID NO 3
<211> LENGTH: 281
<212> TYPE: PRT
<213> ORGANISM: Homo sapiens

<400> SEQUENCE: 3

```
Met Leu Leu Arg Ser Lys Pro Ala Leu Pro Pro Leu Met Leu Leu
1               5                   10                  15

Leu Leu Gly Pro Leu Gly Pro Leu Ser Pro Gly Ala Leu Pro Arg Pro
            20                  25                  30

Ala Gln Ala Gln Asp Val Val Asp Leu Asp Phe Phe Thr Gln Glu Pro
        35                  40                  45

Leu His Leu Val Ser Pro Ser Phe Leu Ser Val Thr Ile Asp Ala Asn
    50                  55                  60

Leu Ala Thr Asp Pro Arg Phe Leu Ile Leu Leu Gly Ser Pro Lys Leu
65                  70                  75                  80

Arg Thr Leu Ala Arg Gly Leu Ser Pro Ala Tyr Leu Arg Phe Gly Gly
                85                  90                  95

Thr Lys Thr Asp Phe Leu Ile Phe Asp Pro Lys Lys Glu Ser Thr Phe
            100                 105                 110

Glu Glu Arg Ser Tyr Trp Gln Ser Gln Val Asn Gln Asp Ile Cys Lys
        115                 120                 125

Tyr Gly Ser Ile Pro Pro Asp Val Glu Glu Lys Leu Arg Leu Glu Trp
    130                 135                 140

Pro Tyr Gln Glu Gln Leu Leu Leu Arg Glu His Tyr Gln Lys Lys Phe
145                 150                 155                 160

Lys Asn Ser Thr Tyr Ser Arg Ser Ser Val Asp Val Leu Tyr Thr Phe
                165                 170                 175

Ala Asn Cys Ser Gly Leu Asp Leu Ile Phe Gly Leu Asn Ala Leu Leu
            180                 185                 190

Arg Thr Ala Asp Leu Gln Trp Asn Ser Ser Asn Ala Gln Leu Leu Leu
        195                 200                 205

Asp Tyr Cys Ser Ser Lys Gly Tyr Asn Ile Ser Trp Glu Leu Gly Asn
    210                 215                 220
```

Glu Pro Asn Ser Phe Leu Lys Lys Ala Asp Ile Phe Ile Asn Gly Ser
225                 230                 235                 240

Gln Leu Gly Glu Asp Phe Ile Gln Leu His Lys Leu Arg Lys Ser
            245                 250                 255

Thr Phe Lys Asn Ala Lys Leu Tyr Gly Pro Asp Val Gly Gln Pro Arg
            260                 265                 270

Arg Lys Thr Ala Lys Met Leu Lys Arg
            275                 280

<210> SEQ ID NO 4
<211> LENGTH: 1209
<212> TYPE: DNA
<213> ORGANISM: Homo sapiens

<400> SEQUENCE: 4

| | | |
|---|---|---|
| ccagcgctgc tccccgggcg ctcctccccg ggcgctcctc cccaggcctc ccgggcgctt | 60 |
| ggatcccggc catctccgca cccttcaagt gggtgtgggt gatttcctgg cgggggagc | 120 |
| agccaggtga gcccaagatg ctgctgcgct cgaagcctgc gctgccgccg ccgctgatgc | 180 |
| tgctgctcct ggggccgctg gtcccctct ccctggcgc cctgccccga cctgcgcaag | 240 |
| cacaggacgt cgtggacctg acttcttca cccaggagcc gctgcacctg gtgagcccct | 300 |
| cgttcctgtc cgtcaccatt gacgccaacc tggccacgga cccgcggttc ctcatcctcc | 360 |
| tgggttctcc aaagcttcgt accttggcca gaggcttgtc cctgcgtac ctgaggtttg | 420 |
| gtggcaccaa gacagacttc ctaattttcg atcccaagaa ggaatcaacc tttgaagaga | 480 |
| gaagttactg gcaatctcaa gtcaaccagg atatttgcaa atatggatcc atccctcctg | 540 |
| atgtggagga gaagttacgg ttggaatggc cctaccagga gcaattgcta ctccgagaac | 600 |
| actaccagaa aaagttcaag aacagcacct actcaagaag ctctgtagat gtgctataca | 660 |
| cttttgcaaa ctgctcagga ctggacttga tctttggcct aaatgcgtta ttaagaacag | 720 |
| cagatttgca gtggaacagt tctaatgctc agttgctcct ggactactgc tcttccaagg | 780 |
| ggtataacat ttcttgggaa ctaggcaatg aacctaacag tttccttaag aaggctgata | 840 |
| ttttcatcaa tgggtcgcag ttaggagaag attttattca attgcataaa cttctaagaa | 900 |
| agtccacctt caaaaatgca aaactctatg gtcctgatgt tggtcagcct cgaagaaaga | 960 |
| cggctaagat gctgaagagg taggaactag aggatgcaga atcactttac ttttcttctt | 1020 |
| tttcctttg agacagagtc tcactctgtc agccagactg gagtgcagtg gtacaatcat | 1080 |
| ggctcactgc aacttcgacc tcccaggctg gtctcttgaa ttcctgtgct caagccatcc | 1140 |
| ttccacctca gcctcccaga gtgccaggat tacaggcatg agccaccaca cccagccacc | 1200 |
| actttttctt | 1209 |

<210> SEQ ID NO 5
<211> LENGTH: 380
<212> TYPE: PRT
<213> ORGANISM: Homo sapiens

<400> SEQUENCE: 5

Met Leu Leu Arg Ser Lys Pro Ala Leu Pro Pro Pro Leu Met Leu Leu
1               5                   10                  15

Leu Leu Gly Pro Leu Gly Pro Leu Ser Pro Gly Ala Leu Pro Arg Pro
            20                  25                  30

Ala Gln Ala Gln Asp Val Val Asp Leu Asp Phe Phe Thr Gln Glu Pro
            35                  40                  45

```
Leu His Leu Val Ser Pro Ser Phe Leu Ser Val Thr Ile Asp Ala Asn
 50                  55                  60

Leu Ala Thr Asp Pro Arg Phe Leu Ile Leu Leu Gly Ser Pro Lys Leu
 65                  70                  75                  80

Arg Thr Leu Ala Arg Gly Leu Ser Pro Ala Tyr Leu Arg Phe Gly Gly
                 85                  90                  95

Thr Lys Thr Asp Phe Leu Ile Phe Asp Pro Lys Lys Glu Ser Thr Phe
             100                 105                 110

Glu Glu Arg Ser Tyr Trp Gln Ser Gln Val Asn Gln Asp Ile Cys Lys
             115                 120                 125

Tyr Gly Ser Ile Pro Pro Asp Val Glu Glu Lys Leu Arg Leu Glu Trp
130                 135                 140

Pro Tyr Gln Glu Gln Leu Leu Leu Arg Glu His Tyr Gln Lys Lys Phe
145                 150                 155                 160

Lys Asn Ser Thr Tyr Ser Arg Ser Ser Val Asp Val Leu Tyr Thr Phe
                165                 170                 175

Ala Asn Cys Ser Gly Leu Asp Leu Ile Phe Gly Leu Asn Ala Leu Leu
                180                 185                 190

Arg Thr Ala Asp Leu Gln Trp Asn Ser Ser Asn Ala Gln Leu Leu Leu
                195                 200                 205

Asp Tyr Cys Ser Ser Lys Gly Tyr Asn Ile Ser Trp Glu Leu Gly Asn
210                 215                 220

Glu Pro Asn Ser Phe Leu Lys Lys Ala Asp Ile Phe Ile Asn Gly Ser
225                 230                 235                 240

Gln Leu Gly Glu Asp Phe Ile Gln Leu His Lys Leu Leu Arg Lys Ser
                245                 250                 255

Thr Phe Lys Asn Ala Lys Leu Tyr Gly Pro Asp Val Gly Gln Pro Arg
                260                 265                 270

Arg Lys Thr Ala Lys Met Leu Lys Ser Phe Leu Lys Ala Gly Gly Glu
                275                 280                 285

Val Ile Asp Ser Val Thr Trp His His Tyr Tyr Leu Asn Gly Arg Thr
290                 295                 300

Ala Thr Arg Glu Asp Phe Leu Asn Pro Asp Val Leu Asp Ile Phe Ile
305                 310                 315                 320

Ser Ser Val Gln Lys Val Phe Gln Val Val Glu Ser Thr Arg Pro Gly
                325                 330                 335

Lys Lys Val Trp Leu Gly Glu Thr Ser Ser Ala Tyr Gly Gly Gly Ala
                340                 345                 350

Pro Leu Leu Ser Asp Thr Phe Ala Ala Gly Phe Met Ile Ile Gly Tyr
                355                 360                 365

Leu Phe Cys Ser Arg Asn Trp Trp Ala Pro Arg Cys
370                 375                 380

<210> SEQ ID NO 6
<211> LENGTH: 1517
<212> TYPE: DNA
<213> ORGANISM: Homo sapiens

<400> SEQUENCE: 6
atgctgctgc gctcgaagcc tgcgctgccg ccgccgctga tgctgctgct cctggggccg     60
ctgggtcccc tctcccctgg cgccctgccc cgacctgcgc aagcacagga cgtcgtggac    120
ctggacttct tcacccagga gccgctgcac ctggtgagcc cctcgttcct gtccgtcacc    180
attgacgcca acctggccac ggacccgcgg ttcctcatcc tcctgggttc tccaaagctt    240
```

```
cgtaccttgg ccagaggctt gtctcctgcg tacctgaggt ttggtggcac caagacagac    300
ttcctaattt tcgatcccaa gaaggaatca acctttgaag agagaagtta ctggcaatct    360
caagtcaacc aggatatttg caaatatgga tccatccctc ctgatgtgga ggagaagtta    420
cggttggaat ggccctacca ggagcaattg ctactccgag aacactacca gaaaagttc     480 aagaacagca cctactcaag aagctctgta gatgtgctat acacttttgc aaactgctca    540
ggactggact tgatctttgg cctaaatgcg ttattaagaa cagcagattt gcagtggaac    600
agttctaatg ctcagttgct cctggactac tgctcttcca aggggtataa catttcttgg    660
gaactaggca atgaacctaa cagtttcctt aagaaggctg atattttcat caatgggtcg    720
cagttaggag aagattttat tcaattgcat aaacttctaa gaaagtccac cttcaaaaat    780
gcaaaactct atggtcctga tgttggtcag cctcgaagaa agacggctaa gatgctgaag    840
agcttcctga aggctggtgg agaagtgatt gattcagtta catggcatca ctactatttg    900
aatggacgga ctgctaccag ggaagatttt ctaaaccctg atgtattgga catttttatt    960
tcatctgtgc aaaagttttt ccaggtggtt gagagcacca ggcctggcaa gaaggtctgg   1020
ttaggagaaa caagctctgc atatggaggc ggagcgccct tgctatccga cacctttgca   1080
gctggcttta tgattattgg ctatctcttc tgttcaagaa attggtgggc accaaggtgt   1140
taatggcaag cgtgcaaggt tcaaagagaa ggaagcttcg agtatacctt cattgcacaa   1200
acactgacaa tccaaggtat aaagaaggag atttaactct gtatgccata aacctccata   1260
atgtcaccaa gtacttgcgg ttaccctatc ctttttctaa caagcaagtg gataaatacc   1320
ttctaagacc tttgggacct catggattac tttccaaatc tgtccaactc aatggtctaa   1380
ctctaaagat ggtggatgat caaaccttgc cacctttaat ggaaaaacct ctccggccag   1440
gaagttcact gggcttgcca gctttctcat atagttttt tgtgataaga aatgccaaag   1500
ttgctgcttg catctga                                                 1517

<210> SEQ ID NO 7
<211> LENGTH: 3
<212> TYPE: PRT
<213> ORGANISM: Artificial
<220> FEATURE:
<223> OTHER INFORMATION: Synthetic polypeptide

<400> SEQUENCE: 7

Ser Lys Lys
1

<210> SEQ ID NO 8
<211> LENGTH: 11
<212> TYPE: DNA
<213> ORGANISM: Artificial
<220> FEATURE:
<223> OTHER INFORMATION: Synthetic oligonucleotide

<400> SEQUENCE: 8
gtaagaaatg a                                                         11

<210> SEQ ID NO 9
<211> LENGTH: 1
<212> TYPE: PRT
<213> ORGANISM: Artificial
<220> FEATURE:
<223> OTHER INFORMATION: Synthetic polypeptide

<400> SEQUENCE: 9
```

Arg
1

<210> SEQ ID NO 10
<211> LENGTH: 4
<212> TYPE: DNA
<213> ORGANISM: Artificial
<220> FEATURE:
<223> OTHER INFORMATION: Synthetic oligonucleotide

<400> SEQUENCE: 10 gtag                                                                    4

<210> SEQ ID NO 11
<211> LENGTH: 17
<212> TYPE: PRT
<213> ORGANISM: Artificial
<220> FEATURE:
<223> OTHER INFORMATION: Synthetic polypeptide

<400> SEQUENCE: 11

Met Ile Ile Gly Tyr Leu Phe Cys Ser Arg Asn Trp Trp Ala Pro Arg
1               5                   10                  15

Cys

<210> SEQ ID NO 12
<211> LENGTH: 54
<212> TYPE: DNA
<213> ORGANISM: Artificial
<220> FEATURE:
<223> OTHER INFORMATION: Synthetic oligonucleotide

<400> SEQUENCE: 12
atgattattg gctatctctt ctgttcaaga aattggtggg caccaaggtg ttaa            54

<210> SEQ ID NO 13
<211> LENGTH: 28
<212> TYPE: DNA
<213> ORGANISM: Artificial
<220> FEATURE:
<223> OTHER INFORMATION: Synthetic oligonucleotide

<400> SEQUENCE: 13
gtattggaca tttttatttc atctgtgc                                         28

<210> SEQ ID NO 14
<211> LENGTH: 20
<212> TYPE: DNA
<213> ORGANISM: Artificial
<220> FEATURE:
<223> OTHER INFORMATION: Synthetic oligonucleotide

<400> SEQUENCE: 14
ggtgttaatg gcaagcgtgc                                                  20

<210> SEQ ID NO 15
<211> LENGTH: 30
<212> TYPE: DNA
<213> ORGANISM: Artificial
<220> FEATURE:
<223> OTHER INFORMATION: Synthetic oligonucleotide

<400> SEQUENCE: 15
gagaattcag gtgagcccaa gatgctgctg                                       30

```
<210> SEQ ID NO 16
<211> LENGTH: 22
<212> TYPE: DNA
<213> ORGANISM: Artificial
<220> FEATURE:
<223> OTHER INFORMATION: Synthetic oligonucleotide

<400> SEQUENCE: 16
ggaattcatg ctgctgcgc tcg                                              22

<210> SEQ ID NO 17
<211> LENGTH: 23
<212> TYPE: DNA
<213> ORGANISM: Artificial
<220> FEATURE:
<223> OTHER INFORMATION: Synthetic oligonucleotide

<400> SEQUENCE: 17 acagttcta atgctcagtt gctc                                             23

<210> SEQ ID NO 18
<211> LENGTH: 22
<212> TYPE: DNA
<213> ORGANISM: Artificial
<220> FEATURE:
<223> OTHER INFORMATION: Synthetic oligonucleotide

<400> SEQUENCE: 18
ttgcctcatc accacttct att                                              22

<210> SEQ ID NO 19
<211> LENGTH: 20
<212> TYPE: DNA
<213> ORGANISM: Artificial
<220> FEATURE:
<223> OTHER INFORMATION: Synthetic oligonucleotide

<400> SEQUENCE: 19
ttggccagag gcttgtctcc                                                 20

<210> SEQ ID NO 20
<211> LENGTH: 21
<212> TYPE: DNA
<213> ORGANISM: Artificial
<220> FEATURE:
<223> OTHER INFORMATION: Synthetic oligonucleotide

<400> SEQUENCE: 20
cccatttggg aaatgcttca g                                               21

<210> SEQ ID NO 21
<211> LENGTH: 20
<212> TYPE: DNA
<213> ORGANISM: Artificial
<220> FEATURE:
<223> OTHER INFORMATION: Synthetic oligonucleotide

<400> SEQUENCE: 21
ccagccgagc cacatcgctc                                                 20

<210> SEQ ID NO 22
<211> LENGTH: 21
<212> TYPE: DNA
<213> ORGANISM: Artificial
<220> FEATURE:
<223> OTHER INFORMATION: Synthetic oligonucleotide
```

```
<400> SEQUENCE: 22
atgagcccca gccttctcca t                                              21

<210> SEQ ID NO 23
<211> LENGTH: 13
<212> TYPE: PRT
<213> ORGANISM: Artificial
<220> FEATURE:
<223> OTHER INFORMATION: Synthetic polypeptide

<400> SEQUENCE: 23

Cys Lys Lys Phe Lys Asn Ser Thr Tyr Ser Ser Lys Lys
1               5                   10
```

HEPARANASE SPLICE VARIANT

FIELD OF THE INVENTION

The present invention, in at least some aspects, is of splice variants of heparanase, as well as diagnostic kits and methods of use, and therapeutic agents and methods of use based thereon, and antibodies specifically binding thereof.

BACKGROUND OF THE INVENTION

Heparanase is an endo-β-D-glucuronidase capable of cleaving heparan sulfate (HS) side chains at a limited number of sites. The consequence of this activity combines structural alteration of the extracellular matrix (ECM) underlying epithelial and endothelial cells, making it more susceptible to cellular invasion, and liberation of a multitude of biological mediators sequestered in the ECM or tethered to HS on the cell membrane.

Heparanase activity has long been associated with metastatic potential of tumor-derived cells (Vlodaysky, I., et al., 1983, Cancer Res 43, 2704-2711), a notion that has been established by employing specific anti-heparanase siRNA and ribozyme methodologies (Edovitsky, E., et al., 2004, J Natl Cancer Inst 96, 1219-1230).

Apart from the well studied enzymatic feature of the enzyme, heparanase was noted to exert biological functions apparently independent of its enzymatic activity. Inactive heparanase was noted to enhance adhesion and migration of normal and tumor-derived cells (Gingis-Velitski, S., et al., 2004, J. Biol. Chem. 279, 23536-23541; Goldshmidt, O., et al., 2003, FASEB J. 17, 1015-1025), and to promote the phosphorylation of signaling molecules such as Akt (Ben-Zaken, O., et al., 2007, Biochem Biophys Res Commun 361, 829-834; Doviner, V., et al., 2006, Mod Pathol 19, 878-888), likely supporting cell survival (Cohen, I., et al., 2006, Int J Cancer 118, 1609-1617). Similarly, enzymatically inactive heparanase was noted to enhance the phosphorylation of p38 and Src, associated with induced tissue factor (TF) and VEGF expression (Zetser, A., et al., 2006, Cancer Res 66, 1455-1463). More recently, heparanase was noted to augment the phosphorylation of EGFR in a Src-dependent manner. EGFR activation by heparanase was associated with enhanced cell proliferation and colony formation in soft agar. Furthermore, a correlation between heparanase and EGFR phosphorylation levels was found in head and neck carcinoma, positioning the heparanase-Src-EGFR axis as an important route in tumor progression.

SUMMARY OF THE INVENTION

The background art does not teach or describe any form of heparanase which is known to participate in primary and secondary tumorigenesis.

The present invention overcomes these drawbacks of the background art by providing at least one novel splice variant of heparanase which is shown herein to be tumorigenic. This novel splice variant is termed "T5" herein. The splicing of this variant causes 144 bp of intron 5 to be joined with exon 4, resulting in a truncated 169 amino acid protein.

T5 is shown herein to have a number of novel effects which are related to tumorigenesis. For example, T5 over expression was associated with increased cell proliferation, larger colonies in soft agar, and a markedly enhanced tumor xenograft development. T5 is over expressed in the majority (75%) of human renal cell carcinoma biopsies examined, suggesting that this splice variant plays an important clinical role. Also T5 augments Src phosphorylation to levels comparable to the full length heparanase, yet T5 was shown to be enzymatically inactive with regard to endo-β-D-glucuronidase activity, as opposed to "known" or "wild type" heparanase, such that T5 is not capable of cleaving heparan sulfate side chains.

The present invention, in at least some embodiments, relates to any one of the polypeptides referred to as T5, T4 or "skip 10" polypeptides, and their corresponding nucleic acid sequence, and fragments and variants and homologs thereof, and the use thereof as a therapeutic and/or diagnostic target or tool.

According to at least some embodiments, there are provided uses of these polypeptides and discrete portions thereof as a drug target for therapeutic small molecules, peptides, antibodies, antisense RNAs, siRNAs, ribozymes, and the like. According to at least some embodiments, the invention relates to diagnostic and therapeutic polyclonal and monoclonal antibodies and fragments thereof that specifically bind the above polypeptides and portions and variants thereof, especially those that target the extracellular domains or portions or variants thereof, or the unique bridge, edge, tail portion, or fragment or variant thereof. According to at least some embodiments, the invention provides human or chimeric monoclonal antibodies and fragments thereof and anti-idiotypic antibodies, that bind specifically to any of the amino acid sequences as set forth in SEQ ID NOs: 1, 3, 5, 7 or 11, or any polypeptides encoded by the nucleic acid sequences as set forth in SEQ ID NOs. 2, 4, 6, 8 or 12, or any corresponding bridges thereof, and variants and fragments and homologs thereof.

According to at least some embodiments of the invention, the antibodies are derived from particular heavy and light chain germline sequences and/or comprise particular structural features such as CDR regions comprising particular amino acid sequences. The invention provides isolated antibodies, methods of making such antibodies, immunoconjugates and bispecific molecules comprising such antibodies and pharmaceutical and diagnostic compositions containing the antibodies, immunoconjugates or bispecific molecules.

According to at least some embodiments of the invention, the specific antibodies may be used for the treatment and/or diagnosis of cancer and/or immune related conditions, as described herein.

In at least some embodiments the present invention provides a diagnostic kit for diagnosis of cancer, including but not limited to renal cancer such as renal carcinoma for example, comprising markers and reagents for detecting qualitative and/or quantitative changes in the expression of a polypeptide or a polynucleotide according to at least some embodiments of the present invention.

In at least some embodiments of the present invention, the kit comprises markers and reagents for detecting the changes by employing a NAT-based technology.

In at least some embodiments of the present invention, the kit comprises at least one nucleotide probe or primer. In at least some embodiments of the present invention, the kit comprises at least one primer pair capable of selectively hybridizing to a nucleic acid sequence according to the teaching of the present invention. In at least some embodiments of the present invention, the kit comprises at least one oligonucleotide capable of selectively hybridizing to a nucleic acid sequence according to the teaching of the present invention.

In at least some embodiments of the present invention, the kit comprises an antibody capable of recognizing or interacting with a polypeptide or protein according to at least some embodiments of the present invention. In at least some embodiments of the present invention, the kit further comprises at least one reagent for performing an immunohistochemical assay, radioimaging assays, in-vivo imaging, positron emission tomography (PET), single photon emission computer tomography (SPECT), magnetic resonance imaging (MRI), Ultra Sound, Optical Imaging, Computer Tomography, radioimmunoassay (RIA), ELISA, slot blot, competitive binding assays, fluorimetric imaging assays, Western blot, FACS, and the like.

All nucleic acid sequences and/or amino acid sequences, according to at least some embodiments of the invention, relate to their isolated form.

It should be noted that oligonucleotide and polynucleotide, or peptide, polypeptide and protein, may optionally be used interchangeably.

According to at least some embodiments, there is provided a monoclonal or polyclonal antibody or an antigen binding fragment thereof comprising an antigen binding site that binds specifically to any one of T5 (SEQ ID NO: 1), T4 (SEQ ID NO: 3), skip 10 (SEQ ID NO: 5), or SEQ ID NO: 11 polypeptides, wherein the antibody binds to the known, wild type heparanase protein with a binding affinity that is at least 5 times lower than a binding affinity to any of the variant proteins of T5 (SEQ ID NO: 1), T4 (SEQ ID NO: 3), skip 10 (SEQ ID NO: 5), or SEQ ID NO: 11.

Optionally the antibody does not feature coagulation-related side effects.

Optionally the antibody is a conformational antibody.

Optionally the antibody is secreted by 9c9 hybridoma deposited according to the provisions of the Budapest Treaty with the Health Protection Agency Culture Collections (Centre for Emergency Preparedness & Response, Porton Down, Salisbury SP4 0JG, United Kingdom), having a Accession Number: 10111101.

An anti-idiotypic antibody that specifically binds an antibody or antigen binding fragment thereof as described herein.

According to the present invention, there is provided a polyclonal or monoclonal antibody that modulates an activity elicited by any one of the T5 (SEQ ID NO: 1), T4 (SEQ ID NO: 3), skip 10 (SEQ ID NO: 5) polypeptides, or a fragment or a variant thereof.

According to the present invention, there is provided an anti-idiotypic antibody that specifically binds an antibody or antigen binding fragment thereof as described herein.

Optionally the antibody blocks or inhibits the interaction of at least one of T5 (SEQ ID NO: 1), T4 (SEQ ID NO: 3), or skip 10 (SEQ ID NO: 5), polypeptide, or a fragment or variant thereof with a counterpart.

According to the present invention, there is provided a 9c9 hybridoma, deposited according to the provisions of the Budapest Treaty with the Health Protection Agency Culture Collections (Centre for Emergency Preparedness & Response, Porton Down, Salisbury SP4 0JG, United Kingdom), having an Accession Number: 10111101; and optionally also an antibody produced thereby.

According to the present invention, there is provided a pharmaceutical composition, comprising an antibody or fragment thereof as described herein, and a pharmaceutically acceptable carrier.

According to the present invention, there is provided use of the antibody or the pharmaceutical composition as described herein in a medicament for treating or preventing cancer or immune related condition, through administration to a subject in need thereof.

According to the present invention, there is provided an siRNA, antisense RNA, or ribozyme that binds the transcript encoding any one of the T5 (SEQ ID NO: 1), T4 (SEQ ID NO: 3), skip 10 (SEQ ID NO: 5), or SEQ ID NO: 11 polypeptides, or a fragment or variant thereof.

According to the present invention, there is provided a pharmaceutical composition comprising the siRNA, antisense RNA, or ribozyme as described herein.

According to the present invention, there is provided use of the siRNA, antisense RNA, or ribozyme or the pharmaceutical composition as described herein in a medicament for treating or preventing cancer or immune related condition, through administration to a subject in need thereof.

Optionally the cancer is selected from the group consisting of solid tumors, sarcomas, hematological malignancies, including but not limited to breast cancer, cervical cancer, ovary cancer, endometrial cancer, melanoma, bladder cancer, lung cancer, pancreatic cancer, colon cancer, prostate cancer, hematopoietic tumors of lymphoid lineage, leukemia, acute lymphocytic leukemia, chronic lymphocytic leukemia, B-cell lymphoma, Burkitt's lymphoma, multiple myeloma, Hodgkin's lymphoma, Non-Hodgkin's lymphoma, myeloid leukemia, acute myelogenous leukemia (AML), chronic myelogenous leukemia, thyroid cancer, thyroid follicular cancer, myelodysplastic syndrome (MDS), tumors of mesenchymal origin, fibrosarcomas and rhabdomyosarcomas, melanoma, uveal melanoma, teratocarcinoma, neuroblastoma, glioma, glioblastoma, benign tumor of the skin, keratoacanthomas, renal cancer, anaplastic large-cell lymphoma, esophageal squamous cells carcinoma, hepatocellular carcinoma, follicular dendritic cell carcinoma, intestinal cancer, muscle-invasive cancer, seminal vesicle tumor, epidermal carcinoma, spleen cancer, bladder cancer, head and neck cancer, stomach cancer, liver cancer, bone cancer, brain cancer, cancer of the retina, biliary cancer, small bowel cancer, salivary gland cancer, cancer of uterus, cancer of testicles, cancer of connective tissue, prostatic hypertrophy, myelodysplasia, Waldenstrom's macroglobinaemia, nasopharyngeal, neuroendocrine cancer, myelodysplastic syndrome, mesothelioma, angiosarcoma, Kaposi's sarcoma, carcinoid, oesophagogastric, fallopian tube cancer, peritoneal cancer, papillary serous mullerian cancer, malignant ascites, gastrointestinal stromal tumor (GIST), and a hereditary cancer syndrome such as Li-Fraumeni syndrome and Von Hippel-Lindau syndrome (VHL).

Optionally the cancer is selected from hepatocellular carcinoma, liver cancer and renal cancer.

Optionally there is provided such a use in combination with one or more of radiation therapy, antibody therapy, chemotherapy, surgery, or in combination therapy with other biological agents, conventional drugs, anti-cancer agents, immunosuppressants, cytotoxic drugs for cancer, chemotherapeutic agents, or in combination with therapeutic agents targeting other complement regulatory proteins (CRPs).

Optionally, the immune related condition is selected from the group consisting of autoimmune diseases, inflammatory diseases, autoinflammatory diseases and infectious diseases.

Optionally the autoimmune disease is selected from the group consisting of rheumatoid arthritis (RA), juvenile rheumatoid arthritis, psoriatic arthritis, rheumatic disease, connective tissue disease, inflammatory rheumatism, degenerative rheumatism, extra-articular rheumatism, arthritis uratica, muscular rheumatism, chronic polyarthritis, psoriasis, ulcerative colitis, Crohn's disease, ulcerative colitis, Crohn's disease, psoriasis arthropathica, asthma, allergy, myasthenia Gravis, autoimmune hemolytic anemia, pure red cell aplasia, thrombocytopenic purpura, Henoch-Schonlein purpura, Evans syndrome, vasculitis, cryoglobulinemic vasculitis, ANCA-associated vasculitis, Wegener's granulomatosis, microscopic polyangiitis, benign lymphocytic angiitis, idiopathic thrombocytopenia, primary biliary cirrhosis, chronic urticaria, dermatomyositis, polymyositis, fibromyositis, multiple sclerosis, bullous skin disorders, pemphigus, pemphigoid, atopic eczema, type 1 diabetes, type 2 diabetes, insulin dependent diabetes mellitus, pemphigus vulgarus, Sjogren's syndrome, antiphospholipid syndrome, Devic's disease, systemic lupus erythematosus, childhood autoimmune hemolytic anemia, Refractory or chronic Autoimmune Cytopenias, Autoimmune Anti-Factor VIII Antibodies in Acquired Hemophilia A, Cold Agglutinin Disease, Neuromyelitis Optica, Stiff Person Syndrome, Graves' Disease, Graves' Ophthalmopathy, autoimmune haemolytic anaemia, Guillian-Barre syndrome, chronic immune polyneuropathy, autoimmune thyroiditis, Addison's disease, membranous glomerulonephropathy, immunoglobulin A nephropathy, Goodpasture's disease, autoimmune gastritis, pernicious anaemia, myogelosis, celiac disease, atopic dermatitis, scleroderma, systemic scleroderma, Hashimoto's thyroiditis, primary myxedema, sympathetic ophthalmia, autoimmune uveitis, ankylosing spondylitis, periarthritis humeroscapularis, panarteritis nodosa, chondrocalcinosis, and immune disorders associated with graft transplantation rejection, such as acute and chronic rejection of organ transplantation, allogenic stem cell transplantation, autologous stem cell transplantation, bone marrow tranplantation, Graft-versus-Host disease.

Optionally the inflammatory disease is selected from the group consisting of gingivitis, periodontitis, hepatitis, chronic action hepatitis, collagen diseases, cirrhosis, pancreatitis, myocarditis, vasculitis, gastritis, gout, gouty arthritis, and inflammatory skin disorders, selected from the group consisting of psoriasis, atopic dermatitis, eczema, rosacea, urticaria, and acne.

Optionally the autoinflammatory disease is selected from the group consisting of normocomplementemic urticarial vasculitis, pericarditis, myositis, anti-synthetase syndrome, scleritis, macrophage activation syndrome, Bechet's Syndrome, PAPA Syndrome, Blau's Syndrome, gout, adult and juvenile Still's disease, cryropyrinopathy, Muckle-Wells syndrome, familial cold-induced auto-inflammatory syndrome, neonatal onset multisystemic inflammatory disease, familial Mediterranean fever, chronic infantile neurologic, cutaneous and articular syndrome, systemic juvenile idiopathic arthritis, Hyper IgD syndrome, Schnitzler's syndrome, and TNF receptor-associated periodic syndrome (TRAPS).

Optionally the infectious disease comprises a disease caused by pathogens such as viruses, bacteria, protozoans and intracellular parasites.

According to the present invention, there is provided a method for any one of screening for a disease, detecting a presence or a severity of a disease, diagnosing a disease, prognosis of a disease, monitoring disease progression or treatment efficacy or relapse of a disease, or selecting a therapy for a disease, comprising detecting in a subject or in a sample obtained from the subject a polypeptide having the sequence according to any of SEQ ID NOs: 1, 3, 5, or 11.

Optionally detecting the polypeptide is performed in vivo or in vitro.

Optionally the disease is selected from a group consisting of cancer and immune related condition.

Optionally the cancer is selected from the group consisting of solid tumors, sarcomas, hematological malignancies, including but not limited to breast cancer (e.g. breast carcinoma), cervical cancer, ovary cancer (ovary carcinoma), endometrial cancer, melanoma, bladder cancer (bladder carcinoma), lung cancer (e.g. adenocarcinoma and non-small cell lung cancer), pancreatic cancer (e.g. pancreatic carcinoma such as exocrine pancreatic carcinoma), colon cancer (e.g. colorectal carcinoma, such ascolon adenocarcinoma and colon adenoma), prostate cancer including the advanced disease, hematopoietic tumors of lymphoid lineage (e.g. leukemia, acute lymphocytic leukemia, chronic lymphocytic leukemia, B-cell lymphoma, Burkitt's lymphoma, multiple myeloma, Hodgkin's lymphoma, Non-Hodgkin's lymphoma), myeloid leukemia (for example, acute myelogenous leukemia (AML), chronic myelogenous leukemia), thyroid cancer, thyroid follicular cancer, myelodysplastic syndrome (MDS), tumors of mesenchymal origin (e.g. fibrosarcomas and rhabdomyosarcomas), melanoma, uveal melanoma, teratocarcinoma, neuroblastoma, glioma, glioblastoma, benign tumor of the skin (e.g. keratoacanthomas), renal cancer, anaplastic large-cell lymphoma, esophageal squamous cells carcinoma, hepatocellular carcinoma, follicular dendritic cell carcinoma, intestinal cancer, muscle-invasive cancer, seminal vesicle tumor, epidermal carcinoma, spleen cancer, bladder cancer, head and neck cancer, stomach cancer, liver cancer, bone cancer, brain cancer, cancer of the retina, biliary cancer, small bowel cancer, salivary gland cancer, cancer of uterus, cancer of testicles, cancer of connective tissue, prostatic hypertrophy, myelodysplasia, Waldenstrom's macroglobinaemia, nasopharyngeal, neuroendocrine cancer, myelodysplastic syndrome, mesothelioma, angiosarcoma, Kaposi's sarcoma, carcinoid, oesophagogastric, fallopian tube cancer, peritoneal cancer, papillary serous mullerian cancer, malignant ascites, gastrointestinal stromal tumor (GIST), and a hereditary cancer syndrome such as Li-Fraumeni syndrome and Von Hippel-Lindau syndrome (VHL).

Optionally the cancer is selected from hepatocellular carcinoma, liver cancer and renal cancer.

Optionally the immune related condition is selected from the group consisting of autoimmune diseases, inflammatory diseases, autoinflammatory diseases and infectious diseases.

Optionally the autoimmune disease is selected from the group consisting of rheumatoid arthritis (RA), juvenile rheumatoid arthritis, psoriatic arthritis, rheumatic disease, connective tissue disease, inflammatory rheumatism, degenerative rheumatism, extra-articular rheumatism, arthritis uratica, muscular rheumatism, chronic polyarthritis, psoriasis, ulcerative colitis, Crohn's disease, ulcerative colitis, Crohn's disease, psoriasis arthropathica, asthma, allergy, myasthenia Gravis, autoimmune hemolytic anemia, pure red cell aplasia, thrombocytopenic purpura, Henoch-Schonlein purpura, Evans syndrome, vasculitis, cryoglobulinemic vasculitis, ANCA-associated vasculitis, Wegener's granulomatosis, microscopic polyangiitis, benign lymphocytic angiitis, idiopathic thrombocytopenia, primary biliary cirrhosis, chronic urticaria, dermatomyositis, polymyositis, fibromyositis, multiple sclerosis, bullous skin disorders, pemphigus, pemphigoid, atopic eczema, type 1 diabetes, type 2 diabetes, insulin dependent diabetes mellitus, pemphigus vulgarus, Sjogren's syndrome, antiphospholipid syndrome, Devic's disease, systemic lupus erythematosus, childhood autoimmune hemolytic anemia, Refractory or chronic Autoimmune Cytopenias, Autoimmune Anti-Factor VIII Antibodies in Acquired Hemophilia A, Cold Agglutinin Disease, Neuromyelitis Optica, Stiff Person Syndrome, Graves' Disease, Graves' Ophthalmopathy, autoimmune haemolytic anaemia, Guillian-Barre syndrome, chronic immune polyneuropathy, autoimmune thyroiditis, Addison's disease, membranous glomerulonephropathy, immunoglobulin A nephropathy, Goodpasture's disease, autoimmune gastritis, pernicious anaemia, myogelosis, celiac disease, atopic dermatitis, scleroderma, systemic scleroderma, Hashimoto's thyroiditis, primary myxedema, sympathetic ophthalmia, autoimmune uveitis, ankylosing spondylitis, periarthritis humeroscapularis, panarteritis *nodosa*, chondrocalcinosis, and immune disorders associated with graft transplantation rejection, such as acute and chronic rejection of organ transplantation, allogenic stem cell transplantation, autologous stem cell transplantation, bone marrow tranplantation, Graft-versus-Host disease.

Optionally the inflammatory disease is selected from the group consisting of gingivitis, periodontitis, hepatitis, chronic action hepatitis, collagen diseases, cirrhosis, pancreatitis, myocarditis, vasculitis, gastritis, gout, gouty arthritis, and inflammatory skin disorders, selected from the group consisting of psoriasis, atopic dermatitis, eczema, rosacea, urticaria, and acne.

Optionally the autoinflammatory disease is selected from the group consisting of normocomplementemic urticarial vasculitis, pericarditis, myositis, anti-synthetase syndrome, scleritis, macrophage activation syndrome, Bechet's Syndrome, PAPA Syndrome, Blau's Syndrome, gout, adult and juvenile Still's disease, cryropyrinopathy, Muckle-Wells syndrome, familial cold-induced auto-inflammatory syndrome, neonatal onset multisystemic inflammatory disease, familial Mediterranean fever, chronic infantile neurologic, cutaneous and articular syndrome, systemic juvenile idiopathic arthritis, Hyper IgD syndrome, Schnitzler's syndrome, and TNF receptor-associated periodic syndrome (TRAPS).

Optionally the infectious disease comprises a disease caused by pathogens such as viruses, bacteria, protozoans and intracellular parasites.

According to at least some embodiments there is provided an isolated fusion protein comprising a peptide having an amino acid sequence selected from the group consisting of at least one of T5 (SEQ ID NO: 1), T4 (SEQ ID NO: 3), skip 10 (SEQ ID NO: 5), or SEQ ID NO: 11, joined to a peptide having a heterologous sequence.

Optionally the protein is attached to a detectable or therapeutic moiety.

Optionally a polyalkyl oxide moiety is attached to the polypeptide.

Optionally the protein is fused to at least a portion of an immunoglobulin.

Optionally the protein further comprises an immunoglobulin heavy chain constant region corresponding to an antibody isotype selected from the group consisting of an IgG1, IgG2, IgG3, IgG4, IgM, IgE, IgA and IgD.

According to at least some embodiments there is provided a polynucleotide having a nucleic acid sequence which encodes for at least one protein as above.

According to at least some embodiments there is provided a pharmaceutical composition comprising a polynucleotide as above and further comprising a pharmaceutically acceptable diluent or carrier.

Optionally the nucleotide sequence is comprised in an expression vector and the composition further comprises a pharmaceutically acceptable diluent or carrier.

Optionally the pharmaceutical composition comprises at least one protein as above, and further comprises a pharmaceutically acceptable diluent or carrier.

According to at least some embodiments there is provided use of the protein as above, or the pharmaceutical composition as above, for a condition characterized by angiogenesis and/or by tissue regeneration.

Optionally the condition is selected from the group consisting of conditions wherein induction of neovascular formation in hypoperfused and normoperfused tissues is of a therapeutic value.

Optionally the conditions are selected from the group consisting of ischemic heart disease, peripheral artery disease or severe limb ischemia; conditions wherein replacement of infracted tissue with autologous cardiac muscle and/or natural development of hypertrophic and dilated cardiomyopathies of any etiology is required; chronic graft rejection and diffuse coronary disease; diabetic neuropathy, vasa-vasorum disease, ischemic heart disease, peripheral artery disease and severe limb ischemia; induction of localized angiogenesis, either in vivo or ex vivo.

The term "immune response" refers to the action of, for example, lymphocytes, antigen presenting cells, phagocytic cells, granulocytes, and soluble macromolecules produced by the above cells or cells produced by the liver or spleen (including antibodies, cytokines, and complement) that results in selective damage to, destruction of, or elimination from the human body of invading pathogens, cells or tissues infected with pathogens, cancerous cells, or, in cases of autoimmunity or pathological inflammation, normal human cells or tissues.

The term "antibody" as referred to herein includes whole polyclonal and monoclonal antibodies and any antigen binding fragment (i.e., "antigen-binding portion") or single chains thereof. An "antibody" refers to a glycoprotein comprising at least two heavy (H) chains and two light (L) chains inter-connected by disulfide bonds, or an antigen binding portion thereof. Each heavy chain is comprised of a heavy chain variable region (abbreviated herein as VH) and a heavy chain constant region. The heavy chain constant region is comprised of three domains, CH1, CH2 and CH3. Each light chain is comprised of a light chain variable region (abbreviated herein as VL) and a light chain constant region. The light chain constant region is comprised of one domain, CL. The VH and VL regions can be further subdivided into regions of hypervariability, termed complementarity determining regions (CDR), interspersed with regions that are more conserved, termed framework regions (FR). Each VH and VL is composed of three CDRs and four FRs, arranged from amino-terminus to carboxy-terminus in the following order: FR1, CDR1, FR2, CDR2, FR3, CDR3, FR4. The variable regions of the heavy and light chains contain a binding domain that interacts with an antigen. The constant regions of the antibodies may mediate the binding of the immunoglobulin to host tissues or factors, including various cells of the immune system (e.g., effector cells) and the first component (Clq) of the classical complement system.

The term "antigen-binding portion" of an antibody (or simply "antibody portion"), as used herein, refers to one or more fragments of an antibody that retain the ability to specifically bind to an antigen (e.g., T4, T5 or "skip 10" polypeptides and proteins). It has been shown that the antigen-binding function of an antibody can be performed by fragments of a full-length antibody. Examples of binding fragments encompassed within the term "antigen-binding portion" of an antibody include (i) a Fab fragment, a monovalent fragment consisting of the V Light, V Heavy, Constant light (CL) and CH1 domains; (ii) a F(ab').2 fragment, a bivalent fragment comprising two Fab fragments linked by a disulfide bridge at the hinge region; (iii) a Fd fragment consisting of the VH and CH1 domains; (iv) a Fv fragment consisting of the VL and VH domains of a single arm of an antibody, (v) a dAb fragment (Ward et al., (1989) Nature 341:544-546), which consists of a VH domain; and (vi) an isolated complementarity determining region (CDR). Furthermore, although the two domains of the Fv fragment, VL and VH, are coded for by separate genes, they can be joined, using recombinant methods, by a synthetic linker that enables them to be made as a single protein chain in which the VL and VH regions pair to form monovalent molecules (known as single chain Fv (scFv); see e.g., Bird et al. (1988) Science 242:423-426; and Huston et al. (1988) Proc. Natl. Acad. Sci. USA 85:5879-5883). Such single chain antibodies are also intended to be encompassed within the term "antigen-binding portion" of an antibody. These antibody fragments are obtained using conventional techniques known to those with skill in the art, and the fragments are screened for utility in the same manner as are intact antibodies.

An "isolated antibody", as used herein, is intended to refer to an antibody that is substantially free of other antibodies having different antigenic specificities (e.g., an isolated antibody that specifically binds T4, T5 or "skip 10" proteins or T4, T5 or "skip 10" polypeptides, such as for example to their unique tails or bridges to these tails, is substantially free of antibodies that specifically bind antigens other than T4, T5 or "skip 10" proteins or polypeptides, respectively). An isolated antibody that specifically binds T4, T5 or "skip 10" proteins or polypeptides may, however, have cross-reactivity to other antigens, such as T4, T5 or "skip 10" proteins or polypeptides from other species, respectively. Moreover, an isolated antibody may be substantially free of other cellular material and/or chemicals.

The terms "monoclonal antibody" or "monoclonal antibody composition" as used herein refer to a preparation of antibody molecules of single molecular composition. A monoclonal antibody composition displays a single binding specificity and affinity for a particular epitope.

The term "human antibody", as used herein, is intended to include antibodies having variable regions in which both the framework and CDR regions are derived from human germline immunoglobulin sequences. Furthermore, if the antibody contains a constant region, the constant region also is derived from human germline immunoglobulin sequences. The human antibodies according to at least some embodiments of the invention may include amino acid residues not encoded by human germline immunoglobulin sequences (e.g., mutations introduced by random or site-specific mutagenesis in vitro or by somatic mutation in vivo). However, the term "human antibody", as used herein, is not intended to include antibodies in which CDR sequences derived from the germline of another mammalian species, such as a mouse, have been grafted onto human framework sequences.

The term "human monoclonal antibody" refers to antibodies displaying a single binding specificity which have variable regions in which both the framework and CDR regions are derived from human germline immunoglobulin sequences. In one embodiment, the human monoclonal antibodies are produced by a hybridoma which includes a B cell obtained from a transgenic nonhuman animal, e g, a transgenic mouse, having a genome comprising a human heavy chain transgene and a light chain transgene fused to an immortalized cell.

The term "recombinant human antibody", as used herein, includes all human antibodies that are prepared, expressed, created or isolated by recombinant means, such as (a) antibodies isolated from an animal (e.g., a mouse) that is transgenic or transchromosomal for human immunoglobulin genes or a hybridoma prepared therefrom (described further below), (b) antibodies isolated from a host cell transformed to express the human antibody, e.g., from a transfectoma, (c) antibodies isolated from a recombinant, combinatorial human antibody library, and (d) antibodies prepared, expressed, created or isolated by any other means that involve splicing of human immunoglobulin gene sequences to other DNA sequences. Such recombinant human antibodies have variable regions in which the framework and CDR regions are derived from human germline immunoglobulin sequences. In certain embodiments, however, such recombinant human antibodies can be subjected to in vitro mutagenesis (or, when an animal transgenic for human Ig sequences is used, in vivo somatic mutagenesis) and thus the amino acid sequences of the VH and VL regions of the recombinant antibodies are sequences that, while derived from and related to human germline VH and VL sequences, may not naturally exist within the human antibody germline repertoire in vivo.

As used herein, "isotype" refers to the antibody class (e.g., IgM or IgG1) that is encoded by the heavy chain constant region genes.

The phrases "an antibody recognizing an antigen" and "an antibody specific for an antigen" are used interchangeably herein with the term "an antibody which binds specifically to an antigen."

As used herein, a "conformational epitope" refers to a sequence of linear or non-linear amino acid segments, composing a structural antigen that comes in direct contact with an antibody and is specifically recognized by the antibody, referred herein as a "conformational antibody".

As used herein, an antibody that "specifically binds" to human T4, T5 or "skip 10" proteins or polypeptides is intended to refer to an antibody that binds to human T4, T5 or "skip 10" proteins or polypeptides optionally one with a KD of $5 \times 10^{-8}$ M or less, $3 \times 10^{-8}$ M or less, or $1 \times 10^{-9}$ M or less.

The term "K-assoc" or "Ka", as used herein, is intended to refer to the association rate of a particular antibody-antigen interaction, whereas the term "Kdiss" or "Kd," as used herein, is intended to refer to the dissociation rate of a particular antibody-antigen interaction. The term "KD", as used herein, is intended to refer to the dissociation constant, which is obtained from the ratio of Kd to Ka (i.e., Kd/Ka) and is expressed as a molar concentration (M). KD values for antibodies can be determined using methods well established in the art. A preferred method for determining the KD of an antibody is by using surface Plasmon resonance, optionally using a biosensor system such as a Biacore® system.

As used herein, the term "high affinity" for an IgG antibody refers to an antibody having a KD of $10^{-8}$ M or less, $10^{-9}$ M or less or $10^{-10}$ M or less for a target antigen. However, "high affinity" binding can vary for other antibody isotypes. For example, "high affinity" binding for an IgM isotype refers to an antibody having a KD of $10^{-7}$ M or less, or $10^{-8}$ M or less.

As used herein, the term "tail" refers to a peptide sequence at the end of an amino acid sequence that is unique to a splice variant according to the present invention. Therefore, a splice variant having such a tail may optionally be considered as a chimera, in that at least a first portion of the splice variant is typically highly homologous (often 100% identical) to a portion of the corresponding known protein, while at least a second portion of the variant comprises the tail.

As used herein, the term "an edge portion" refers to a connection between two portions of a splice variant according to the present invention that were not joined in the wild type or known protein. An edge may optionally arise due to a join between the above "known protein" portion of a variant and the tail, for example, and/or may occur if an internal portion of the wild type sequence is no longer present, such that two portions of the sequence are now contiguous in the splice variant that were not contiguous in the known protein. A "bridge" may optionally be an edge portion as described above, but may also include a join between a tail and a "known protein" portion of a variant.

In some embodiments, a bridge between a tail and a "known protein" portion of a variant, comprises at least about 10 amino acids, or in some embodiments at least about 20 amino acids, or in some embodiments at least about 30 amino acids, or in some embodiments at least about 40 amino acids, in which at least one amino acid is from the tail and at least one amino acid is from the "known protein" portion of a variant. In some embodiments, the bridge may comprise any number of amino acids from about 10 to about 40 amino acids (for example, 10, 11, 12, 13 . . . 37, 38, 39, 40 amino acids in length, or any number in between).

It should be noted that a bridge cannot be extended beyond the length of the sequence in either direction, and it should be assumed that every bridge description is to be read in such manner that the bridge length does not extend beyond the sequence itself.

Furthermore, bridges are described with regard to a sliding window in certain contexts below. For example, certain descriptions of the bridges feature the following format: a bridge between two edges (in which a portion of the known protein is not present in the variant) may optionally be described as follows: a bridge portion of CONTIG-NAME_P1 (representing the name of the protein), comprising a polypeptide having a length "n", wherein n is at least about 10 amino acids in length, optionally at least about 20 amino acids, at least about 30 amino acids, at least about 40 amino acids, or at least about 50 amino acids in length, wherein at least two amino acids comprise XX (2 amino acids in the center of the bridge, one from each end of the edge), having a structure as follows (numbering according to the sequence of CONTIG-NAME_P1): a sequence starting from any of amino acid numbers 49−x to 49 (for example); and ending at any of amino acid numbers 50+((n−2)−x) (for example), in which x varies from 0 to n−2. In this example, it should also be read as including bridges in which n is any number of amino acids between 10-50 amino acids in length. Furthermore, the bridge polypeptide cannot extend beyond the sequence, so it should be read such that 49−x (for example) is not less than 1, nor 50+((n−2)−x) (for example) greater than the total sequence length.

The term "cancer" as used herein should be understood to encompass any neoplastic disease (whether invasive or metastatic) which is characterized by abnormal and uncontrolled cell division causing malignant growth or tumor. In addition, the term "cancer" as used herein encompasses conditions characterized by any disregulated blood and/or lymph vessel formation (angiogenesis) which promotes tumor cell growth and/or metastatic spread.

Non-limiting examples of cancer which may be treated with a composition according to at least some embodiments of the present invention are solid tumors, sarcomas, hematological malignancies, including but not limited to breast cancer (e.g. breast carcinoma), cervical cancer, ovary cancer (ovary carcinoma), endometrial cancer, melanoma, bladder cancer (bladder carcinoma), lung cancer (e.g. adenocarcinoma, small cell lung cancer, large cell lung cancer and non-small cell lung cancer), pancreatic cancer (e.g. pancreatic carcinoma such as exocrine pancreatic carcinoma), colon cancer (e.g. colorectal carcinoma, such as colon adenocarcinoma and colon adenoma), prostate cancer including the advanced disease, hematopoietic tumors of lymphoid lineage (e.g. leukemia, acute lymphocytic leukemia, chronic lymphocytic leukemia, B-cell lymphoma, Burkitt's lymphoma, multiple myeloma, Hodgkin's lymphoma, Non-Hodgkin's lymphoma), myeloid leukemia (for example, acute myelogenous leukemia (AML), chronic myelogenous leukemia), thyroid cancer, thyroid follicular cancer, myelodysplastic syndrome (MDS), tumors of mesenchymal origin (e.g. fibrosarcomas and rhabdomyosarcomas), melanoma, uveal melanoma, teratocarcinoma, neuroblastoma, glioma, glioblastoma, benign tumor of the skin (e.g. keratoacanthomas), renal cancer, anaplastic large-cell lymphoma, esophageal squamous cells carcinoma, hepatocellular carcinoma, follicular dendritic cell carcinoma, intestinal cancer, muscle-invasive cancer, seminal vesicle tumor, epidermal carcinoma, spleen cancer, bladder cancer, head and neck cancer, stomach cancer, liver cancer, bone cancer, brain cancer, cancer of the retina, biliary cancer, small bowel cancer, salivary gland cancer, cancer of uterus, cancer of testicles, cancer of connective tissue, prostatic hypertrophy, myelodysplasia, Waldenstrom's macroglobinaemia, nasopharyngeal, neuroendocrine cancer, myelodysplastic syndrome, mesothelioma, angiosarcoma, Kaposi's sarcoma, carcinoid, oesophagogastric, fallopian tube cancer, peritoneal cancer, papillary serous mullerian cancer, malignant ascites, gastrointestinal stromal tumor (GIST), and a hereditary cancer syndrome such as Li-Fraumeni syndrome and Von Hippel-Lindau syndrome (VHL), wherein the cancer is non-metastatic, invasive or metastatic.

With regard to ovarian cancer, the disease is selected from the group including but not limited to primary and metastatic cancer of the ovary, including epithelial ovarian cancer such as serous, mucinous, endometroid, clear cell, mixed epithelial, undifferentiated carcinomas and Brenner tumor, as well as other non-epithelial neoplasms of the ovary, including germ cell malignancies.

With regard to breast cancer, the disease is selected from the group including but not limited to primary and metastatic cancer of the breast, including mammary carcinomas such as Infiltrating Ductal carcinoma, Ductal carcinoma in-situ, Infiltrating Lobular carcinoma, Lobular carcinoma in-situ, Inflammatory breast cancer, Paget's disease of the breast, and other non-epithelial neoplasms of the breast, including fibrosarcomas, leiomyosarcomas, rhapdomyosarcomas, angiosarcomas, cystosarcoma phyllodes.

With regard to lung cancer, the disease is selected from the group consisting of but not limited to squamous cell lung carcinoma, lung adenocarcinoma, carcinoid, small cell lung cancer or non-small cell lung cancer.

With regard to liver cancer, the disease is selected from the group consisting of but not limited to primary and metastatic cancers of the liver and intrahepatic bile duct, including hepatocellular carcinoma, cholangiocarcinoma, hepatic angiosarcoma and hepatoblastoma.

With regard to renal cancer, the disease is selected from the group consisting of but not limited to primary and metastatic cancer of the kidney, including renal cell carcinoma (i.e. renal adenocarcinoma), as well as other non-epithelial neoplasms of the kidney, including nephroblastoma (i.e. Wilm's tumor), transitional cell neoplasms of the renal pelvis, and various sarcomas of renal origin.

With regard to colon cancer, the disease is selected from the group consisting of but not limited to primary and metastatic cancer of the colon, including adenocarcinoma, mucinous carcinoma (including signet ring cell-type and medullary), adenosquamous carcinoma, carcinoid, small cell carcinoma, squamous cell carcinoma, undifferentiated carcinoma, as well as other non-epithelial neoplasms of the colon, including lymphoma, melanoma and sarcoma.

With regard to pancreatic cancer, the disease is selected from the group consisting of but not limited to primary and metastatic cancers of the exocrine pancreas, including adenocarcinoma, serous and mucinous cystadenocarcinomas, acinar cell carcinoma, undifferentiated carcinoma, pancreatoblastoma and neuroendocrine tumors such as insulinoma.

With regard to melanoma, the disease is selected from the group consisting of but not limited to primary and metastatic malignant melanoma, including cutaneous melanoma such as superficial spreading melanoma, nodular melanoma, acral lentiginous melanoma and lentigo maligna melanoma, as well as mucosal melanoma, intraocular melanoma, desmoplastic/neurotropic melanoma and melanoma of soft parts (clear cell sarcoma).

With regard to prostate cancer, the disease is selected from the group consisting of but not limited to primary and metastatic cancer of the prostate, including prostatic intra-epithelial neoplasia, atypical adenomatous hyperplasia, prostate adenocarcinoma, mucinous or signet ring tumor, adenoid cystic carcinoma, prostatic duct carcinoma, carcinoid and small-cell undifferentiated cancer.

As used herein the term "hematological malignancies" refers to acute lymphocytic leukemia, chronic lymphocytic leukemia (CLL), acute lymphoblastic leukemia, acute myelogenous leukemia, chronic myelogenous leukemia, multiple myeloma, B-cell lymphoma, such as Hodgkin's lymphoma, non-Hodgkin's lymphoma (NHL), low grade/follicular NHL, small cell lymphocytic (SL) NHL, small cell NHL, grade I small cell follicular NHL, grade II mixed small and large cell follicular NHL, grade III large cell follicular NHL, large cell NHL, Diffuse Large B-Cell NHL, intermediate grade diffuse NHL, high grade immunoblastic NHL, high grade lymphoblastic NHL, high grade small non-cleaved cell NHL, bulky disease NHL, mantle cell lymphoma, Mucosa-Associated Lymphatic Tissue lymphoma (MALT), Burkitt lymphoma, Mediastinal large B cell lymphoma, Nodal marginal zone B cell lymphoma (NMZL), Splenic marginal zone lymphoma (SMZL), Extranodal marginal zone B cell lymphoma, Intravascular large B cell lymphoma, Primary effusion lymphoma, Lymphomatoid granulomatosis, B-cell prolymphocytic leukemia, Precursor B lymphoblastic leukemia, Hairy cell leukemia, AIDS-related lymphoma and Waldenstrom's Macroglobulinernia.

The term "immune related condition" as used herein will encompass any disease disorder or condition selected from the group including but not limited to autoimmune diseases, inflammatory diseases, autoinflammatory diseases and infectious diseases.

As used herein the term "autoimmune diseases" refers to a group of diseases characterized by generation of an immune response against self tissues or cells. For example, the term autoimmune diseases refers to rheumatoid arthritis (RA), juvenile rheumatoid arthritis, psoriatic arthritis, rheumatic disease, connective tissue disease, inflammatory rheumatism, degenerative rheumatism, extra-articular rheumatism, arthritis uratica, muscular rheumatism, chronic polyarthritis, psoriasis, inflammatory bowel disease (IBD), ulcerative colitis, Crohn's disease, psoriasis arthropathica, asthma, allergy, myasthenia Gravis, autoimmune hemolytic anemia, pure red cell aplasia, thrombocytopenic purpura, Henoch-Schonlein purpura, Evans syndrome, vasculitis, cryoglobulinemic vasculitis, ANCA-associated vasculitis, Wegener's granulomatosis, microscopic polyangiitis, benign lymphocytic angiitis, idiopathic thrombocytopenia, primary biliary cirrhosis, chronic urticaria, dermatomyositis, polymyositis, fibromyositis, multiple sclerosis, bullous skin disorders, pemphigus, pemphigoid, atopic eczema, type 1 diabetes, type 2 diabetes, insulin dependent diabetes mellitus, pemphigus vulgarus, Sjogren's syndrome, antiphospholipid syndrome, Devic's disease, systemic lupus erythematosus, childhood autoimmune hemolytic anemia, Refractory or chronic Autoimmune Cytopenias, Autoimmune Anti-Factor VIII Antibodies in Acquired Hemophilia A, Cold Agglutinin Disease, Neuromyelitis Optica, Stiff Person Syndrome, Graves' Disease, Graves' Ophthalmopathy, autoimmune haemolytic anaemia, Guillian-Barre syndrome, chronic immune polyneuropathy, autoimmune thyroiditis, Addison's disease, membranous glomerulonephropathy, immuno-globulin A nephropathy, Goodpasture's disease, autoimmune gastritis, pernicious anaemia, myogelosis, celiac disease, atopic dermatitis, scleroderma, systemic scleroderma, Hashimoto's thyroiditis, primary myxedema, sympathetic ophthalmia, autoimmune uveitis, ankylosing spondylitis, periarthritis humeroscapularis, panarteritis nodosa, chondrocalcinosis, and immune disorders associated with graft transplantation rejection, such as acute and chronic rejection of organ transplantation, allogenic stem cell transplantation, autologous stem cell transplantation, bone marrow tranplantation, Graft-versus-Host disease.

The term "inflammatory disease" as used herein should be understood to encompass any inflammatory disease. Non-limiting examples of such diseases which are gingivitis, periodontitis, hepatitis, chronic action hepatitis, collagen diseases, cirrhosis, pancreatitis, myocarditis, vasculitis, gastritis, gout, gouty arthritis, and inflammatory skin disorders, selected from the group consisting of psoriasis, atopic dermatitis, eczema, rosacea, urticaria, and acne.

The term "autoinflammatory disease" as used herein should be understood to encompass any autoinflammatory disease. Non-limiting examples of an autoinflammatory disease are normocomplementemic urticarial vasculitis, pericarditis, myositis, anti-synthetase syndrome, scleritis, macrophage activation syndrome, Bechet's Syndrome, PAPA Syndrome, Blau's Syndrome, gout, adult and juvenile Still's disease, cryropyrinopathy, Muckle-Wells syndrome, familial cold-induced auto-inflammatory syndrome, neonatal onset multisystemic inflammatory disease, familial Mediterranean fever, chronic infantile neurologic, cutaneous and articular syndrome, systemic juvenile idiopathic arthritis, Hyper IgD syndrome, Schnitzler's syndrome, and TNF receptor-associated periodic syndrome (TRAPS).

The term "infectious disease" as used herein should be understood to encompass any disease caused by pathogens such as viruses, bacteria, protozoans and intracellular parasites.

Non-limiting examples of viral diseases are hepatitis type B virus, hepatitis type C virus, hepatitis type A virus, parvoviruses such as adeno-associated virus and cytomegalovirus, papovaviruses such as papilloma virus, polyoma viruses, SV40, adenoviruses, herpes viruses such as herpes simplex type I (HSV-I), herpes simplex type II (HSV-II), and Epstein-Barr virus (EBV), poxviruses such as variola (smallpox) and vaccinia virus, RNA viruses including but not limited to human immunodeficiency virus type I (HIV-I), human immunodeficiency virus type II (HIV-II), human T-cell lymphotropic virus type II (HTLV-II), influenza virus, measles virus, rabies virus, Sendai virus, picornaviruses such as poliomyelitis virus, coxsackieviruses, rhinoviruses, reoviruses, togaviruses such as rubella virus and Semliki forest virus, and arboviruses.

Non-limiting examples of bacterial infections are *Streptococcus pyogenes, Streptococcus pneumoniae, Neisseria gonorrhoea, Neisseria meningitides, Corynebacterium diphtheriae, Clostridium botulinum, Clostridium perfringens, Clostridium tetani, Haemophilus influenzae, Klebsiella pneumoniae, Klebsiella ozaenae, Klebsiella rhinoscleromotis, Staphylococcus aureus, Vibrio cholerae, Escherichia coli, Pseudomonas aeruginosa, Campylobacter (Vibrio) fetus, Campylobacter jejuni, Aeromonas hydrophila, Vacillus cereus, Edwardsiella tarda, Yersinia enterocolitica, Yersinia pestis, Yersinia pseudotuberculosis, Shigella dysenteriae, Shigella flexneri, Shigella sonnei, Salmonella typhiimurium, Salmonella typhii, Treponema pallidum, Treponema pertenue, Treponema carateneum, Borrelia vincentii, Borrelia burgdorferi, Leptospira icterohemorrhagiae, Mycobacterium tuberculosis, Toxoplasma gondii, Pneumocystis carinii, Francisella tularensis, Brucella abortus, Brucella suis, Brucella melitensis, Mycoplasma* spp., *Rickettsia prowazeki, Rickettsia tsutsugumushi, Chlamydia* spp., and *Helicobacter pylori*.

Non-limiting examples of protozoal infections are *Entomoeba histolytica, Trichomonas tenas, Trichomonas hominis, Trichomonas vaginalis, Trypanosoma gambiense, Trypanosoma rhodesiense, Trypanosoma cruzi, Leishmania donovani, Leishmania tropica, Leishmania braziliensis, Pneumocystis pneumonia, Plasmodium vivax, Plasmodium falciparum*, and *Plasmodium malaria*.

The term "angiogenesis and regeneration related condition" as used herein will encompass any disease disorder or condition wherein inducing arteriogenesis, lymphangiogenesis, vasculogenesis, cardiomyogenesis, mitosis or proliferation of a smooth muscle cell, a skeletal muscle cell, or a cardiomyocyte, and tissue regeneration is of a therapeutic value. Non-limiting examples of angiogenesis and regeneration related conditions which may be treated with a composition according to at least some embodiments of the present invention are conditions wherein induction of neovascular formation in hypoperfused and normoperfused tissues is of a therapeutic value. By utilizing embodiments of the invention, it is possible, e.g., to stimulate the neoformation, development, proliferation and growth of vessels. Embodiments of the invention are effective also for the neoformation, development, proliferation and growth of smooth and striated muscular cells. Non-limiting examples of such conditions are ischemic heart disease, peripheral artery disease or severe limb ischemia. Another non-limiting example of angiogenesis and regeneration related conditions which may be treated with a composition according to at least some embodiments of the present invention are conditions wherein regeneration of myocardial tissue, induction of cardiomyocyte mitosis and/or proliferation is of a therapeutic value. Non-limiting examples of such conditions are conditions wherein replacement of infracted tissue with autologous cardiac muscle and/or natural development of hypertrophic and dilated cardiomyopathies of any etiology is required. Another non-limiting example of angiogenesis and regeneration related conditions which may be treated with a composition according to at least some embodiments of the present invention is transplant medicine. Non-limiting examples of such conditions are chronic graft rejection and diffuse coronary disease. Another non-limiting example of angiogenesis and regeneration related conditions which may be treated with a composition according to at least some embodiments of the present invention are conditions wherein increasing perfusion in ischemic tissues of patients with diabetes-related micro and macroangiopathy is of a therapeutic value, such as diabetic neuropathy, vasa-vasorum disease, ischemic heart disease, peripheral artery disease and severe limb ischemia, among others.

Another embodiment of the invention is the induction of localized angiogenesis, either in vivo or ex vivo. Preferably, the angiogenesis is induced in ischemic tissue, either in vivo, in vitro or ex vivo. Preferably, the angiogenesis is induced in hypoperfused myocardial tissue, either in vivo, in vitro or ex vivo. Hypoperfused myocardial tissue may be ischemic, viable, hibernated, stunned, preconditioned, injured, infarcted, non-viable, fibrosed or necrosed. More preferably, the claimed method induces angiogenesis in vivo in hypoperfused myocardial tissue.

Another embodiment of the invention is the induction of arteriogenesis in vivo, in vitro or ex vivo. In one embodiment of the present invention, arteriogenesis is induced in normoperfused tissue in vivo, in vitro or ex vivo. In another embodiment of the present invention, arteriogenesis is induced in ischemic tissue, in vivo, in vitro or ex vivo. Preferably, the arteriogenesis is induced in hypoperfused myocardial tissue in vivo, in vitro or ex vivo. Hypoperfused myocardial tissue may be ischemic, viable, hibernated, stunned, preconditioned, injured, infarcted, non-viable, fibrosed or necrosed. More preferably, the claimed method induces arteriogenesis in hypoperfused myocardial tissue in vivo.

Another embodiment of the invention is the induction of vasculogenesis in vivo, in vitro or ex vivo. In one embodiment of the present invention, vasculogenesis is induced in normoperfused tissue in vivo, in vitro or ex vivo. In another embodiment of the present invention, vasculogenesis is induced in ischemic tissue, in vivo, in vitro or ex vivo. Preferably, the vasculogenesis is induced in hypoperfused myocardial tissue, in vivo, in vitro or ex vivo. Hypoperfused myocardial tissue may be ischemic, viable, hibernated, stunned, preconditioned, injured, non-viable, infarcted, necrosed or fibrosed. Morepreferably, the vasculogenesis is induced in hypoperfused myocardial tissue in vivo.

Another embodiment of the invention is the induction of lymphangiogenesis in vivo, in vitro or ex vivo. In one embodiment of the present invention, lymphangiogenesis is induced in normoperfused tissue, in vivo, in vitro or ex vivo. In another embodiment of the present invention, lymphangiogenesis is induced in ischemic tissue, in vivo, in vitro or ex vivo. Preferably, the lymphangiogenesis is induced in hypoperfused myocardial tissue, in vivo, in vitro or ex vivo. Hypoperfused myocardial tissue may be ischemic, viable, hibernated, stunned, preconditioned, injured, non-viable, infarcted, necrosed orfibrosed. More preferably, the lymphangiogenesis is induced in hypoperfused myocardial tissue in vivo.

Another embodiment of the invention is the induction of mitosis in vivo, in vitro or ex vivo. In one embodiment of the present invention, mitosis is induced in normoperfused tissue, in vivo, in vitro or ex vivo. In another embodiment of the present invention, mitosis is induced in ischemic tissue in vivo, in vitro or ex vivo. Preferably, the mitosis is induced in hypoperfused myocardial tissue, in vivo, in vitro or ex vivo. Hypofused myocardial tissue may be ischemic, viable, hibernated, stunned, preconditioned, injured, non-viable, infarcted, necrosed or fibrosed. More preferably, the mitosis is induced inhypoperfused myocardial tissue in vivo.

The method also relates to the induction of proliferation of cells in which mitosis has been induced. In preferred embodiments, the mitosis or proliferation is in smooth muscle cells, skeletal muscle cells, or cardiomyocytes. In embodiments of the invention, a smooth muscle cell, skeletal muscle cell or cardiomyocyte in which mitosis or proliferation is induced is in myocardial tissue, skeletal tissue, or muscle tissue. Any type of muscle tissue may be regenerated by methods of the invention.

Another embodiment of the invention is the induction of tissue regeneration in vivo, in vitro or ex vivo. In one embodiment of the present invention, tissue regeneration is induced in normoperfused territories, in vivo, in vitro or ex vivo. In another embodiment of the present invention, tissue regeneration is induced in ischemic territories, in vivo, in vitro or ex vivo. Preferably, the tissue regeneration is induced in hypoperfused myocardial territories, in vivo, in vitro or ex vivo. Hypoperfused myocardial territory may be ischemic, viable, hibernated, stunned, preconditioned, injured, non-viable, infarcted, necrosed or fibrosed. More preferably, the tissue regeneration is induced in hypoperfused myocardial territories in vivo.

The present invention can be utilized as sole therapy or associated with conventional angiogenesis, revascularization and/or regeneration procedures. As used herein the term "treatment" refers to care provided to relieve illness and refers to both a therapeutic treatment or prophylactic/preventative measures, wherein the objective is to prevent or slow down (lessen) the targeted pathologic condition or disorder. Those in need of treatment include those already with the disorder as well as those prone to have the disorder or those in whom the disorder is to be prevented. The term treatment as used herein refers also to "maintenance therapy", which is a treatment that is given to keep a pathologic condition or disorder from coming back after it has disappeared following the initial therapy.

The term "therapeutically effective amount" refers to an amount of agent according to the present invention that is effective to treat a disease or disorder in a mammal.

As used herein the term "diagnosis" refers to the process of identifying a medical condition or disease by its signs, symptoms, and in particular from the results of various diagnostic procedures, including e.g. detecting the expression of the nucleic acids or polypeptides according to at least some embodiments of the invention in a biological sample (e.g. in cells, tissue or serum, as defined below) obtained from an individual. Furthermore, as used herein the term "diagnosis" encompasses screening for a disease, detecting a presence or a severity of a disease, distinguishing a disease from other diseases including those diseases that may feature one or more similar or identical symptoms, providing prognosis of a disease, monitoring disease progression or relapse, as well as assessment of treatment efficacy and/or relapse of a disease, disorder or condition, as well as selecting a therapy and/or a treatment for a disease, optimization of a given therapy for a disease, monitoring the treatment of a disease, and/or predicting the suitability of a therapy for specific patients or subpopulations or determining the appropriate dosing of a therapeutic product in patients or subpopulations. The diagnostic procedure can be performed in vivo or in vitro. It should be noted that a "biological sample obtained from the subject" may also optionally comprise a sample that has not been physically removed from the subject.

As used herein the term "combination therapy" refers to the simultaneous or consecutive administration of two or more medications or types of therapy to treat a single disease. In particular, the term refers to the use of any of the polypeptides, polynucleotides, antibodies or pharmaceutical compositions according to at least some embodiments of the invention in combination with at least one additional medication or therapy. Thus, treatment of a disease using the agents according to at least some embodiments of the present invention may be combined with therapies well known in the art that include, but are not limited to, radiation therapy, antibody therapy, chemotherapy or surgery or in combination therapy with other biological agents, conventional drugs, anti-cancer agents, immunosuppressants, cytotoxic drugs for cancer, chemotherapeutic agents. According to at least some embodiments, treatment of kidney cancer using the agents according to at least some embodiments of the present invention may be combined with an agent including but not limited to Sunitinib, Sorafenib, Temsirolimus, Nexavar, Pazopanib, and Rapamycin. Optionally, treatment of liver cancer using the agents according to at least some embodiments of the present invention may be combined with an agent including but not limited to combination of 5-Fluorouracil (5 FU) and Leucovorin and 5 FU, Tomudex, Mitomycin C, and CPT-11.

According to at least some embodiments, treatment of ovarian cancer using the agents according to at least some embodiments of the present invention may be combined with an agent including but not limited to paclitaxol and cisplatin.

According to at least some embodiments, as a non-limiting example of combination treatment of an immune related disorder, treatment of rheumatoid arthritis disorder using the agents according to at least some embodiments of the present invention may be combined with but not limited to a first-line combination treatment with a drug such as aspirin and cortisone (corticosteroids), which are used to reduce pain and inflammation, and one or more second-line combination drugs, such as gold, methotrexate, and hydroxychloroquine (Plaquenil), promote disease remission and prevent progressive joint destruction. According to at least some embodiments, treatment of rheumatoid arthritis disorder may optionally feature an agent according to the present invention combined with an agent including but not limited to methotrexate and retuximab. Other immune related disorders may optionally be treated with a combination of the appropriate agent(s) as selected by one of ordinary skill in the art, along with at least one agent according to the present invention.

As used herein, the term "subject" includes any human or nonhuman animal. The term "nonhuman animal" includes all vertebrates, e.g., mammals and non-mammals, such as nonhuman primates, sheep, dogs, cats, horses, cows, chickens, amphibians, reptiles, etc.

Without wishing to be limited by a closed list, the advantages of the variant heparanases described herein, and in particular T5, over the wild type heparanase (known in the literature to enhance proliferation and endothelial cell growth, as well as growth of other types of cells) include but are not limited to: T5 is shorter in length, therefore easier to produce/handle and probably more stable in-vivo; the T5 variant lacks the hydrolase activity and is not functional as an ECM (extra cellular matrix) degrading agent (as it doesn't degrade heparan sulfate) and therefore cannot enhance metastasis, unlike the wild type heparanase; and the T5 variant is apparently not affected by heparin, and the unique tail is not a heparin binding site.

BRIEF DESCRIPTION OF THE DRAWINGS

FIG. 1. Expression of T5 splice variant. A. Schematic structure of heparanase splice variants emerging from Compugen's LEADS search. B. 3'RACE analysis of RNA extracted from white blood cells collected from healthy donor (WBC), chronic myeloid leukemia patient (CML), lung carcinoma and adjacent normal lung tissue. C. Sequence alignment indicating that the 3'RACE product corresponds to the predicted T5 splice variant sequence. D. Schematic presentation of heparanase (WT) and T5 exon composition. E. Sequence alignment for the amino acid sequences of the T5 variant and the wild type heparanase (swissprot accession number: HPSE_HUMAN).

FIG. 3. T5 augments Src phosphorylation. A. Over expression. CAG myeloma (left) and 293 (right) cells infected with heparanase (Hepa), T5, or control empty vector (Vo) were grown in the absence (−) or presence (+) of heparin (50 μg/ml) under serum-free conditions. Total cell lysates were subjected to immunoblotting applying anti-heparanase 1453 (upper and second panels), anti-phospho-Src (p-Src, third panels), anti-Src (fourth panels) anti-phospho-Erk (p-Erk, fifth panels), and anti-Erk2 (sixth panels) antibodies. Src phosphorylation index was calculated by densitometry analysis of phosphorylated Src levels divided by the total Src values. Data is presented as average fold increase ±SE of Src phosphorylation compared with control, Vo cells, set arbitrary to a value of 1 (lower panels) of five independent experiments. B. Gene silencing. Parental 293 cells were transfected with anti-heparanase, anti-T5, or control siRNAs. Total RNA was extracted and RT-PCR analysis was performed applying T5 (upper panel), heparanase (Hepa, second panel) and GAPDH (third panel) specific primers. Corresponding cell lysates were subjected to immunoblotting applying phospho-Src (p-Src, fourth panel), Src (fifth panel), phospho-Erk (p-Erk, sixth panel) and Erk2 (seventh panel) antibodies. Src phosphorylation index was calculated as above and is shown graphically in the lower panel. Note decreased Src phosphorylation levels upon T5 down regulation.

FIG. 11 presents the results of the hybridoma screening. FIG. 11B presents immunohistochemical results, demonstrating the reacton of the 7c4 antibody with tumor xenografts generated by CAG myeloma cells over expressing either a wild type heparanase or T5 (FIG. 11B, left); while the 9c9 antibody only reacted specifically with tumor xenografts produced by CAG cells over expressing T5 (FIG. 11B, right lower panel). FIG. 11C presents staining of human tumor biopsies with 9c9 antibody.

DESCRIPTION OF SOME EMBODIMENTS

Figure 2A:
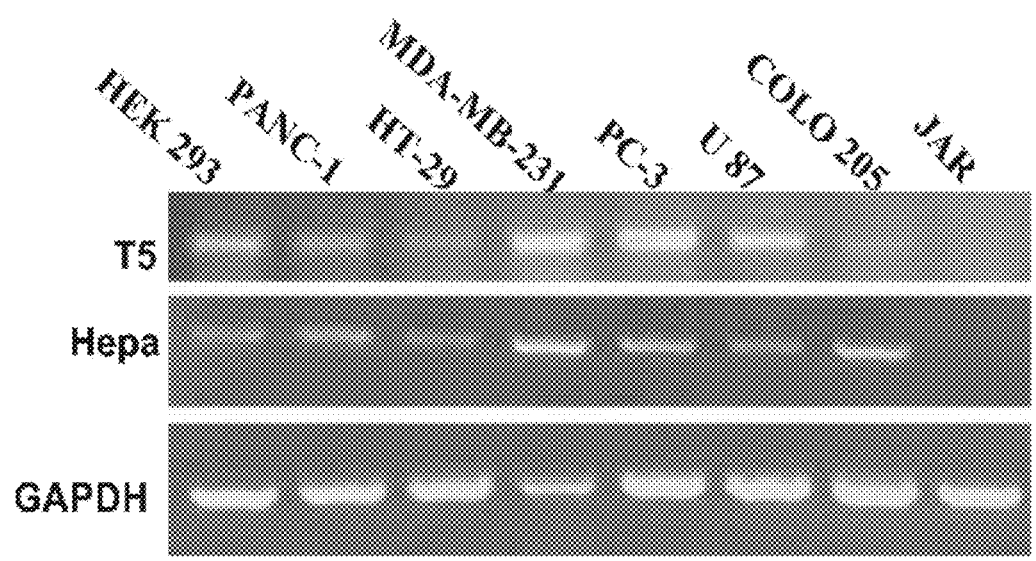
FIG. 2. Cloning and expression of T5. A. RT-PCR analysis. Total RNA was extracted from the indicated cell line and subjected to RT-PCR analysis applying T5 (upper panel), heparanase (second panel) and GAPDH (third panel) specific primers, specified in the 'Materials and Methods' section. B. T5 transfection. T5 was cloned into mammalian expression vector (pcDNA3) and transfected 293 cells were left untreated (0) or incubated with tunicamycin (10, 20 μg/ml) or chloroquine (Chl; 100 μM). Control cells were transfected with an empty vector (Vo). Cell lysates (left) and cell conditioned medium (right) were blotted with anti-heparanase 1453 antibody. C. Cellular localization. Stably transfected 293 cells were triple stained for Myc-tag (T5; middle, red), the ER marker calnexin (ER, left, green), and merged with cell nuclei labeled with TO-PRO (right, blue). Cells were similarly stained with anti-Myc-tag (T5; middle, red), the Golgi marker wheat germ agglutinin-FITC (Golgi, left, green) and merged with cell nuclei labeled with TO-PRO (right, blue). Shown is one image in which the two colors are of equal intensities, representative of many images, all exhibiting similar localization pattern. D. Enzymatic activity. 293 cells transfected with heparanase (Hepa), T5 or control empty vector (Vo) were subjected to three freeze-thaw cycles and applied onto culture dishes coated with $^{35}$S-labelled ECM. Release of sulfate-labeled material eluted in fractions 15-30 was evaluated as measure of heparanase activity, as described in 'Materials and Methods'.

According to at least some embodiments of the present invention, there is provided the T5 human heparanase splice variant, as well as diagnostic kits and methods of use, and therapeutic agents and methods of use based thereon.

The T5 human heparanase splice variant was first discovered in silico by using LEADS, Compugen's alternative splicing modeling platform. Tumor-derived cell lines (i.e., CAG myeloma) and tumor biopsies were utilized to validate T5 expression and function in vivo. Signaling (i.e., Src phosphorylation) was evaluated following T5 gene silencing or over-expression, and correlated with cell proliferation, colony formation, and tumor xenograft development when T5 was overexpressed (with a corresponding reduction or elimination when T5 was suppressed). Interestingly, the T5 splice variant was shown to lack the enzymatic activity of full length human heparanase (endo-β-D-glucuronidase activity which is capable of cleaving heparan sulfate side chains).

T5 expression is up-regulated in 75% of human renal cell carcinoma biopsies examined, suggesting that this splice variant is clinically important for renal cancer. Overall, T5 was shown to be pro-tumorigenic.

In terms of structural differences, WT pro-heparanase is catalytically inactive and features an 8 kDa portion joined to a 50 kDa portion by a linker. Upon cleavage of the linker, the 8 kDa portion and the 50 kDa portion form a heterodimer, which is enzymatically active.

T5, T4 and the skip 10 variants all feature the complete 8 kDa portion and linker; however, they all feature a truncated version of the WT 50 kDa portion and instead feature a unique tail in place of the missing part of the WT 50 kDa portion. The BLAST alignment of T5 variant protein as compared to the WT protein is shown in FIG. 1. T5 protein, according to at least some embodiments of the invention, comprises a first amino acid sequence being at least 90% homologous to MLLRSKPALPPPLMLLLLGPLGPLSP-GALPRPAQAQDVVDLDFFTQEPLHLVSP SFLSVTI-DANLATDPRFLILLGSPKLRTLARGLSPAYLRFGGTK-TDFLIFDPKKE STFEERSYWQSQVNQDICKYGSIPPDVEEKLR-LEWPYQEQLLLREHYQKKFKN STYS, corresponding to amino acids 1-166 of known protein heparanase protein HPSE_HUMAN, which also corresponds to amino acids 1-166 of T5 variant, and a second amino acid sequence comprising or consisting of a polypeptide having the sequence SKK, corresponding to amino acids 166-169 of T5 variant, wherein said first amino acid sequence and second amino acid sequence are contiguous and in a sequential order.

The signal peptide of the wild type heparanase is retained in T5 variant, enabling its delivery to the ER and Golgi apparatus, glycosylation and secretion. Protein N-glycosylation likely occurs on a single asparagine residue (Asn$^{162}$), which is preserved in T5 and shown to be required for protein secretion. However, the T5 variant protein is devoided of heparanase enzymatic activity, and, as shown herein, the T5 variant protein cannot compete with endogenous heparanase. This is largely because T5 is incapable of heparin binding. Although the basic heparin binding domain of heparanase (Lys$^{158}$-Asn$^{162}$) is retained in T5 and is followed by additional positively-charged amino acids (KK), it is demonstrated herein that T5 fails to interact with heparin. Based upon the analysis of the other variant sequences, it is expected that the T4 and skip 10 variant proteins also have similar properties. Therefore each such variant protein lacks the enzymatic activity of the WT protein and also is not functional as an ECM (extra cellular matrix) degrading agent (as it doesn't degrade heparan sulfate). At least the T5 variant, and possibly the other variants as well, are apparently not at all affected by heparin, while the unique tail is not a heparin binding site.

The lack of heparin binding and lack of enzymatic domain of these variant proteins might circumvent the coagulation-related side effects, shown for the WT protein, such as injection site hemorrhage (J Hepatol. 2009 May; 50(5):958-68); serious bleeding and a positive anti-platelet antibody test (Invest New Drugs. 2008 February; 26(1):89-94); thrombocytopenia and pulmonary embolism (Clin Cancer Res. 2006 Sep. 15; 12(18):5471-80).

For the sake of convenience, the correspondence between the SEQ ID NOs and the names of the sequences according to at least some embodiments of the present invention are provided in the below table.

Table of Sequences

| SEQ ID NO | Name in text |
|---|---|
| 1 | T5 protein |
| 2 | T5 polynucleotide |
| 3 | T4 protein |
| 4 | T4 polynucleotide |
| 5 | Skip 10 protein |
| 6 | Skip 10 polynucleotide |
| 7 | T5 amino acids of the unique tail |
| 8 | T5 polynucleotide encoding the unique tail |
| 9 | T4 amino acids of the unique tail |
| 10 | T4 polynucleotide encoding the unique tail |
| 11 | Skip 10 amino acids of the unique tail |
| 12 | Skip 10 polynucleotide encoding the unique tail |

The following examples are offered for illustrative purposes only, and are not intended to limit the scope of the present invention in any way.

All patent and literature references cited in the present specification are hereby incorporated by reference in their entirety.

EXAMPLE 1

Heparanase T5 Function

Materials and Methods
Discovery of Heparanase Splice Variants.

The discovery of T4 and T5 heparanase splice variants and/or their functionality was carried out using LEADS, Compugen's alternative splicing modeling platform (Sorek, R., et al., 2002, Genome Res 12, 1060-1067; Sorek, R., et al., 2004, Genome Res 14, 1617-1623). Briefly, human ESTs and cDNAs were obtained from NCBI GenBank and aligned to the human genome build (www "." ncbi "." nlm " " nih "." gov/genome/guide/human) using the LEADS clustering and assembly algorithms The platform cleans the expressed sequences from vectors and immunoglobulins, masks them for repeats and low-complexity regions, and aligns the expressed sequences to the genome while modeling alternative splicing. The discovery of the skip 10 splice variant was carried out using "non-EST-based method for exon-skipping prediction". In principle, this method relies on a gene's exon structure/size and the human/mouse homology of the exon and its surrounding sequences.

T5 Cloning and gene constructs.
3' rapid amplification of cDNA ends (RACE) analysis was performed using the following forward heparanase primers:
5'-GAGAATTCAGGTGAGCCCAAGATGCTGCTG-3' (SEQ ID NO:15),
5'-GGAATTCATGCTGCTGCGCTCG-3' (SEQ ID NO:16), according to the manufacturer's (Ambion, Austin, Tex.) instructions. The PCR product was purified by Wizard SV Gel PCR Clean-Up System (Promega, Madison, Wis.), and sequenced. The T5 cDNA was sub-cloned into eukaryotic expression plasmids pcDNA3, pSecTag2A or pTK208 lentivirus vector, essentially as described (Ben-Zaken, O., et al., 2008, Int J Biochem Cell Biol 40, 530-542).

Antibodies and reagents.
Anti-Myc-tag (sc-40), anti-Src (sc-18) and anti-calnexin (sc-11397) antibodies were purchased from Santa Cruz Biotechnology (Santa Cruz, Calif.). Anti-phospho-Src (Tyr416) antibody was purchased from Cell Signaling Technologies (Beverly, Mass.). Anti-heparanase #1453 and #733 have previously been characterized ( ). Anti mouse platelet endothelial cell adhesion molecule (PECAM)-1 (CD31) polyclonal antibody was kindly provided by Dr. Joseph A. Madri (Yale University, New Haven, Conn.). Concanavalin A-Sepharose and bromodeoxyuridine (BrdU) were purchased from GE Healthcare (Buckinghamshire, England) and anti-BrdU monoclonal antibody-HRP conjugated was purchased from Roche (Mannheim, Germany). Fluorescein wheat germ agglutinin was purchased from Vector Laboratories (Burlingame, Calif.). Src inhibitors PP1, PP2 and Src inhibitor I (Merck Biosciences, GmbH, Germany) were dissolved in DMSO as stock solution. DMSO was added to the cell culture as a control.

Cells and Cell Culture.
HEK 293, human choriocarcinoma JAR, U87-MG glioma, Colo205 and HT29 colon carcinoma, PC-3 prostate carcinoma, MDA-MB-231 breast carcinoma, and PANC-1 pancreatic carcinoma cells were purchased from the American Type Culture Collection (ATCC, Manassas, Va.). FaDu pharynx carcinoma cells were kindly provided by Dr. Eben L. Rosenthal (University of Alabama at Birmingham, Birmingham, Ala.) and CAG myeloma cells were kindly donated (Nadav, L., et al., 2006, Cancer Res 66, 8608-8616). Cells were grown in Dulbecco's modified Eagle's medium (Biological Industries, Beit Haemek, Israel) supplemented with 10% fetal calf serum and antibiotics. Human umbilical vein endothelial cells (HUVEC) were isolated and grown essentially as described.

Gene Silencing and PCR Analysis.
Anti-heparanase and anti-T5 siRNA oligonucleotides (si-GENOME ON-TARGET plus SMART pool duplex) were purchased from Dharmacon (Thermo Fisher Scientific Inc, Waltham, Mass.) and transfection was carried out with DharmaFECT reagent, according to the manufacturer's (Dharmacon) instruction. PCR was preformed with the following sets of primer: Heparanase F: 5'-ACAGT-TCTAATGCTCAGTTGCTC-3' (SEQ ID NO:17), Heparanase R: 5'-TTGCCTCATCACCACTTCTATT-3' (SEQ ID NO:18); T5 F: 5'-TTGGCCAGAGGCTTGTCTCC-3' (SEQ ID NO:19), T5 R: 5'-CCCATTTGGGAAATGCTTCAG-3' (SEQ ID NO:20); GAPDH F: 5'-CCAGCCGAGCCA-CATCGCTC-3' (SEQ ID NO:21), and GAPDH R: 5'-AT-GAGCCCCAGCCTTCTCCAT-3' (SEQ ID NO:22).

Immunocytochemistry.
Immunofluorescent staining was performed essentially as described (Fux, L., et al., 2009, Cancer Res 69, 1758-1767).

Cell Lysates, Activity Assay and Protein Blotting.
Preparation of cell lysates, protein blotting, and measurement of heparanase enzymatic activity were carried out as described previously (Zetser, A., et al., 2006, Cancer Res 66, 1455-1463; Fux, L., et al., 2009, Cancer Res 69, 1758-1767).

Cell proliferation.
Cell proliferation was analyzed by BrdU incorporation using cell proliferation labeling reagent (1:1000, GE Healthcare), as described in Zetser, A., et al (2003 Cancer Res 63, 7733-7741). At least 1000 cells were counted for each cell type.

Colony Formation in Soft Agar.

Three ml of DMEM containing 0.5% low melt agarose (Bio-Rad, Hercules, Calif.) and 10% fetal calf serum was poured into 60 mm petri dishes. The layer was covered with cell suspension ($0.5 \times 10^4$ cells) in 1.5 ml DMEM containing 0.3% low melt agarose and 10% fetal calf serum, followed by addition of 2 ml DMEM containing 10% fetal calf serum. Medium was exchanged every 3 days. Colonies were visualized and counted under a microscope after 2-5 weeks, as described.

Tumorigenicity and Immunohistochemistry.

Cells from exponential cultures of control-, heparanase-, and T5-infected CAG myeloma cells were detached with trypsin/EDTA, washed with PBS and brought to a concentration of $1 \times 10^7$ cells/ml. Cell suspension ($1 \times 10\%.1$ ml) was inoculated subcutaneously at the right flank of 5-weeks old female athymic nude mice (n=7). Xenograft size was determined twice a week by externally measuring tumors in two dimensions using a caliper. At the end of the experiment, mice were sacrificed and xenografts were removed, weighted and fixed in formalin. Paraffin-embedded 5 micron sections were subjected to immunostaining with anti-PECAM-1 (CD31) or anti-smooth muscle actin (1A4, Sigma) antibodies, using the Envision kit, according to the manufacturer's (Dako, Glostrup, Denmark) instructions, as described (Fux, L., et al., 2009, Cancer Res 69, 1758-1767). All animal experiments were approved by the Animal Care Committee of the Technion, Haifa, Israel.

Statistics.

Data are presented as mean±SE. Statistical significance was analyzed by two-tailed Student's t test. The value of $p<0.05$ was considered significant. All experiments were repeated at least three times with similar results.

Results

Discovery, Cloning and Expression of Heparanase Splice Variant, T5.

Three different splice forms of heparanase (T4, T5, skip 10; FIG. 1A) were discovered in silico using Compugen's alternative splicing modeling platform LEADS (T4 and T5), and a non-EST-based method for exon-skipping prediction (skip 10). 3'rapid amplification of cDNA ends (RACE) analysis yielded a product of 687 by that was highly enriched in RNA extracted from lung carcinoma tissue and chronic myeloid leukemia (CML) cells compared with controls [adjacent normal lung tissue and white blood cells collected from healthy donors (WBC), respectively] (FIG. 1B). Sequencing of the 3'RACE product matched the expected T5 sequence (FIG. 1C), indicating that the T5 splice variant is being expressed. The expression of T4 and Skip 10 splice variants could not be detected under these experimental settings. T5 expression was subsequently confirmed by RT-PCR analysis of total RNA extracted from several cancer-derived cell lines applying T5-specific primers (FIG. 2A, upper panel). T5 expression is detected, along with heparanase, to various levels in essentially all cell lines examined JAR cells reported to be negative for heparanase (Shteper, P. J., et al., 2003, Oncogene 22, 7737-7749) (FIG. 2A, middle panel) were also negative for T5 expression (FIG. 2A, upper panel).

Figure 2B:
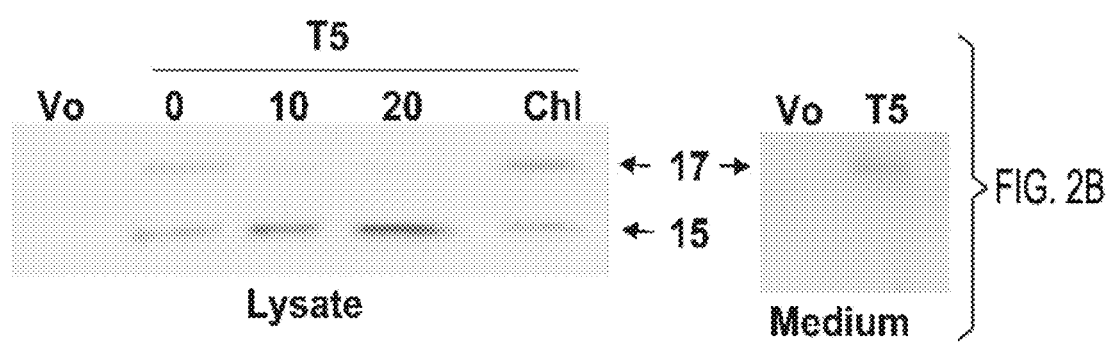

In order to verify that T5 encodes for a protein, the T5 sequence was cloned into a mammalian expression vector and lysate samples prepared from stably transfected 293 cells were subjected to immunoblotting. Anti-heparanase antibody clearly detected a ~15 kDa protein band, a molecular weight slightly higher than that anticipated from the deduced amino acid sequence (14,207; FIG. 2B, 0) while no reactivity was detected in control cells transfected with an empty plasmid (FIG. 2B, Vo). In addition, a ~17 kDa protein band was also seen (FIG. 2B, 0).

Figure 10:
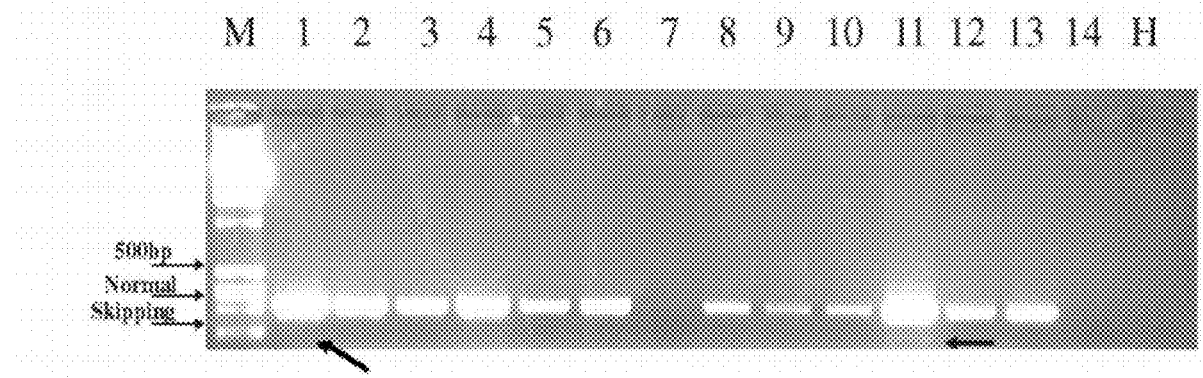
FIG. 10 presents RT-PCR results demonstrating expression of the Skip 10 variant in various tissue samples and cell lines. Lane 1:Cervix+HeLa; lane 2:Uterus; lane 3-Ovary; lane 4-Placenta; lane 5-Breast; lane 6-Colon; lane 7-Pancreas; lane 8-Liver+Spleen; lane 9-Brain; lane 10-Prostate; lane 11-Testis; lane 12-Kidney; lane 13-Thyroid; lane 14-Assorted Cell-lines (5). M=1 kb ladder marker; H=H2O negative control.

Two possibilities were considered for the appearance of two T5 protein bands: different glycosylation pattern or proteolytic cleavage of the high molecular weight protein. The first possibility was examined by incubating T5 over expressing cells with increasing concentrations of tunicamycin, an inhibitor of protein N-glycosylation. Indeed, tunicamycin treatment markedly reduced the amount of the ~17 kDa band, while levels of the ~15 kDa protein were increased (FIG. 2B, 10, 20). In contrast chloroquine, reported to inhibit proteolytic processing of heparanase within lysosomes (Zetser, A., et al., 2004, J Cell Sci 117, 2249-2258), did not significantly affect the ratio between the two T5 forms (FIG. 2, Chi). These results indicate that T5 is being expressed as a ~15 kDa protein and a more glycosylated 17 kDa form, and that T5 is not subjected to processing within lysosomes.

As would be expected from the presence of a signal peptide, T5 is secreted and found in the cell conditioned medium (FIG. 2B, right). This is in agreement with its localization to the ER and Golgi apparatus (FIG. 2C), as demonstrated previously for heparanase (Fux, L., et al., 2009, Cancer Res 69, 1758-1767). Subjecting lysates of stably transfected cells to heparanase activity assay indicated that T5 lacks heparanase enzymatic activity (FIG. 2D, T5 vs. Hepa) as would be expected from a heparanase variant comprising only a small portion of the 50 kDa subunit (FIG. 1A, T5). Moreover, T5 expression did not seem to significantly impinge on the activity of endogenous heparanase (FIG. 2D, T5 vs. Vo), suggesting that T5 does not function as a modulator of heparanase enzymatic activity.

T5 Activates Src and Facilitates Cell Proliferation.

Since T5 does not appear to modulate heparanase enzymatic activity (FIG. 2D), an alternative function of the splice variant was considered with regard to whether T5 facilitates the phosphorylation of Src, shown previously to be induced by heparanase. Src phosphorylation was increased nearly 3-fold in CAG myeloma cells infected with heparanase (FIG. 3A, left, third and lower panels, Hepa), in agreement with a similar effect noted in diverse cell systems. Notably, CAG cells infected with T5 exhibited comparable induction of Src phosphorylation (FIG. 3A, left, third panel, T5), as determined by densitometry analysis (FIG. 3A, left, lower panel). Even higher enhancement of Src phosphorylation (~4-fold) was found in 293 cells over expressing heparanase or T5 proteins (FIG. 3A, right panels). Src phosphorylation enhanced by heparanase or T5 was not affected by heparin (FIG. 3A, +), suggesting that the observed stimulation is not mediated by cell surface HS (Levy-Adam, F., et al., 2008, PLoS ONE 3, e2319). In contrast, Erk phosphorylation was not affected by heparanase or T5 over expression (FIG. 3A, fifth and sixth panels), suggesting a specific trait.

Next the opposite approach was utilized and siRNA specific for the inhibition of endogenous heparanase or T5 expression by 293 cells was designed (FIG. 3B). Anti-T5 siRNA significantly and specifically decreased T5 expression while heparanase expression was not inhibited (FIG. 3B, T5, upper and second panels). In contrast, anti-heparanase siRNA inhibited both heparanase and T5 expression (FIG. 3B, upper and second panel). Heparanase gene silencing was associated with reduced Src phosphorylation (FIG. 3B, Hepa, fourth panel), in agreement with the notion that endogenous heparanase is engaged in Src regulation. Notably, not only heparanase but also T5 silencing resulted in reduced Src phosphorylation (FIG. 3B, T5, fourth panel). Densitometry analysis revealed >2-fold decrease in Src phosphorylation levels following heparanase and T5 silencing (FIG. 3B, lower panel). In contrast, the phosphorylation levels of Erk were not affected (FIG. 3C, sixth panel), suggesting a specific effect.

Figure 7C:
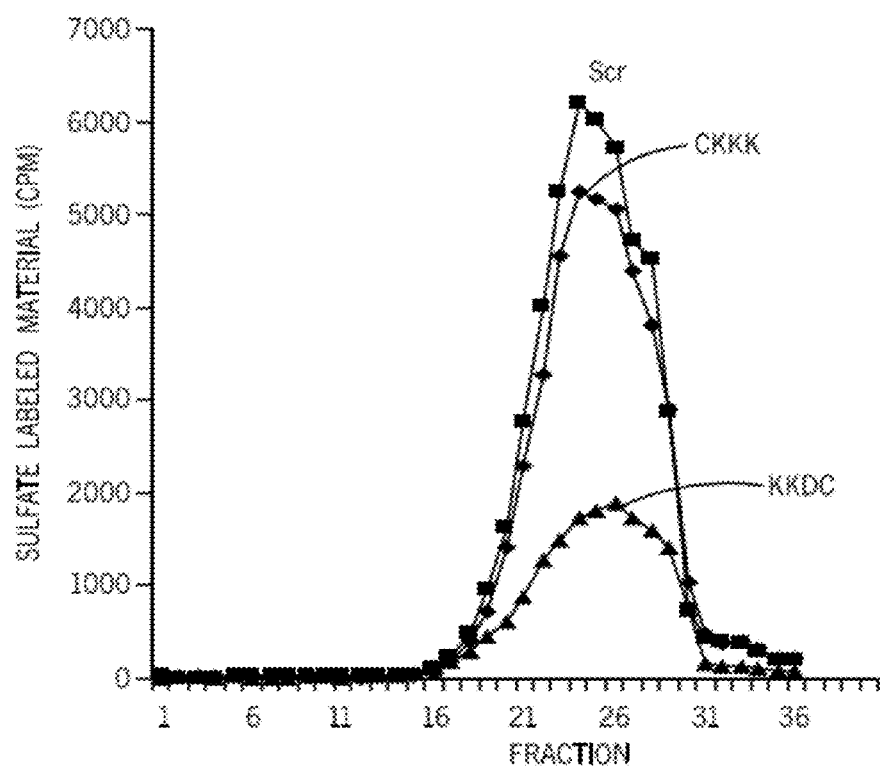
FIG. 7. T5 does not interact with heparin. A. Cell lysates. Lysate samples prepared from control (Vo), heparanase (Hepa) and T5 over expressing 293 cells were subjected to immunoblotting without or following incubation with concanavalin A (Con A), Fractogel, or heparin beads, applying anti-heparanase (left, upper panel) and anti-T5 (left, lower panel) antibodies. Control (Vo), heparanase and T5 transfected 293 cells were left untreated (−) or incubated with heparin (+, 50 μg/ml) for 20 h under serum-free conditions. Cell conditioned medium was subjected to immunoblotting applying anti heparanase (right, upper panel) and anti-T5 (right, lower panel) antibodies. Note that T5 does not bind heparin. B,C. Peptide analysis. Peptides corresponding to the heparin binding domain of heparanase (KKDC) or T5 (CKKK) which includes its unique three amino acids (SKK), and control scrambled (Scr) peptide were subjected to gel electrophoresis prior to or following incubation with heparin beads (+Heparin). C. Enzymatic activity. Purified active heparanase (40 ng) was applied onto $^{35}$S-labeled ECM in the presence of control (Scr), KKDC or CKKK peptides (50 µg/ml) and release of sulfate labeled material was evaluated by gel filtration on a Sepharose-6B column, as described under 'Materials and Methods'. Note that in contrast to the KKDC peptide, the CKKK peptide failed to interact with heparin or to inhibit heparanase enzymatic activity.

It has been reported previously that interaction of heparanase with cell membrane HS results in clustering of syndecans. Syndecan clustering by heparanase or by a peptide (termed KKDC) corresponding to the heparin-binding domain of heparanase, stimulated the adhesion and spreading of various cell types, involving PKC, Src, and Rac1 activity. The heparin binding sequence $Lys^{158}$-$ASn^{162}$ (Levy-Adam, F., et al., 2008, PLoS ONE 3, e2319) is retained in the T5 splice variant and is followed by the addition of three unique amino acids, SKK, thought to comprise additional binding sites for heparin (FIG. 1A). Src activation by T5, noted above, may therefore result from clustering and activation of cell membrane HSPG. Our findings argue however against this possibility. First, inclusion of heparin did not inhibit Src activation by T5 (FIG. 3A, +). In fact, T5 failed to bind heparin (FIG. 7A, left, lower panel), while interaction with the lectin Concanavalin A was retained (FIG. 7A, lower panel, ConA), in agreement with T5 being glycosylated (FIG. 2B). Similarly, T5 levels in the cell culture medium were not affected by the addition of heparin, while heparanase levels are markedly increased (FIG. 7A, right). Second, a peptide harboring the heparin binding domain, including the unique SKK residues (CK-KFKNSTYSSKK, SEQ ID NO:23) failed to interact with heparin (FIG. 7B, CKKK) or to inhibit heparanase enzymatic activity (FIG. 7C), both accomplished by the KKDC peptide (FIG. 7B, C). Therefore it was concluded that Src activation by T5 is HS-independent, but rather likely involves interaction with other cell surface molecule(s).

Figure 4A:
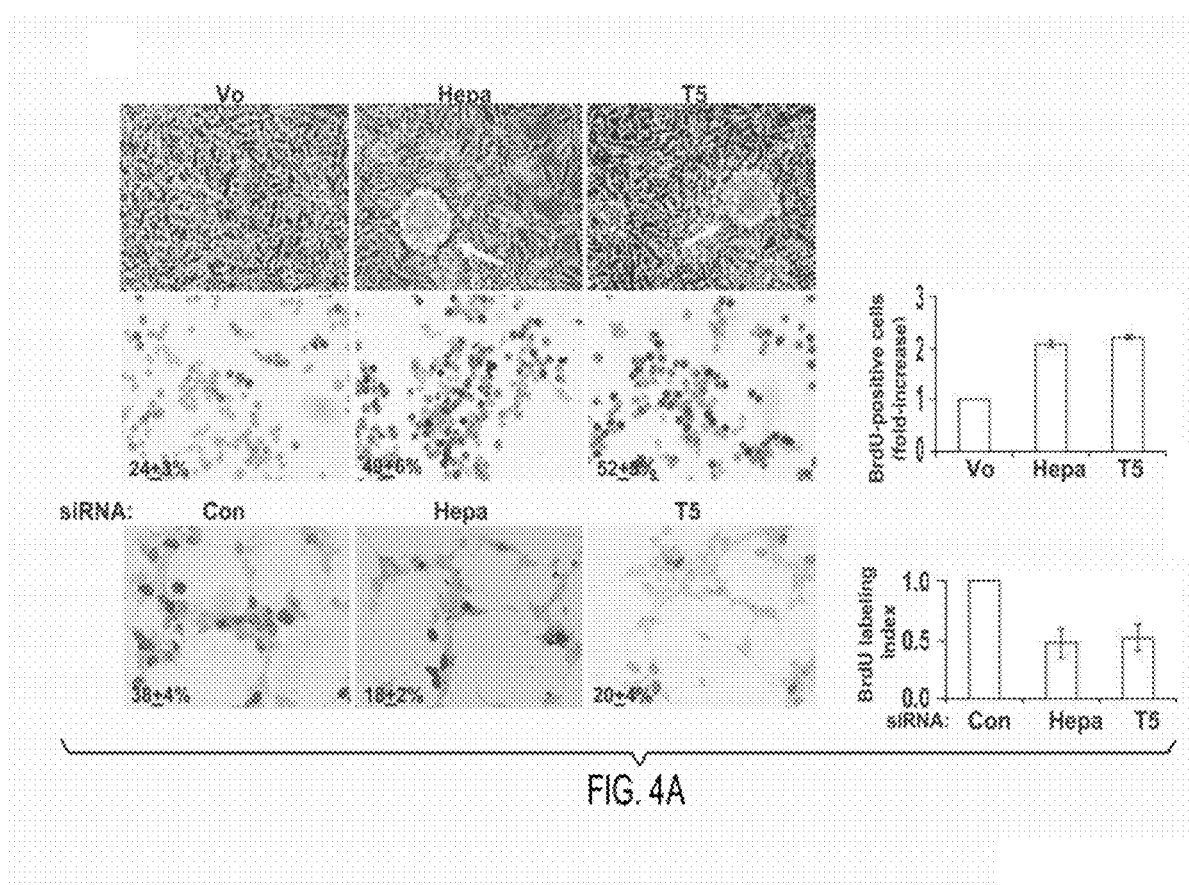
FIG. 4. T5 augments cell proliferation. A. BrdU incorporation. Morphology of control (Con), heparanase (Hepa)- and T5-infected CAG myeloma cell cultures is shown in the upper panels. Direct evaluation of DNA synthesis is demonstrated by BrdU incorporation (second panels). Sub-confluent cultures of control (Vo), heparanase (Hepa)- and T5-infected CAG cells were grown in serum-free medium for 20 h followed by incubation with BrdU (1:1000) for 2 h. Cells were then fixed and immunostained with anti BrdU monoclonal antibody. Positively stained, red-brown nuclei were counted vs. blue, hematoxylin counter-stained nuclei. At least 1000 cells were counted for each cell type and the percentage of positively stained cells is noted in each panel. Fold increase in BrdU incorporation is shown graphically on the right panel. Gene silencing. 293 cells were transfected with anti-GFP (si-GFP), anti-heparanase (si-Hepa) or anti-T5 siRNA oligonucleotides and BrdU incorporation was evaluated as above except that cells were kept in serum-containing medium (lower panels). Note 2-fold decrease in BrdU incorporation following heparanase or T5 gene silencing (lower right panel). B. Colony formation in soft agar. Control (Vo) heparanase (Hepa)- and T5-infected CAG (upper panel), Fadu (second panel) and 293 (third panels) cells (5×10$^3$ cells/dish) were mixed with soft agar and cultured for 3-5 weeks. CAG cells were similarly grown in the absence (DMSO; fourth panels) or presence of Src inhibitor (PP2, 0.4 nM; lower panels). Shown are representative photomicrographs of colonies at high (×100) magnification.

Further the involvement of Src in different aspects of tumor progression including cell proliferation was examined in heparanase and T5 over expressing cells (FIG. 4). Control CAG cells mainly grow while adhering to the culture dish as a monolayer (FIG. 4A, Vo; upper panel). In contrast, heparanase and T5 infected CAG cells were noted to form large foci (FIG. 4A, Hepa, T5; upper panel, arrows), indicating their overgrowth. Increased cell proliferation was further revealed by BrdU incorporation (FIG. 4A, second panels). Thus, while 24±3% of control CAG cells incorporated BrdU (FIG. 4A, second panel, Vo), heparanase- and T5-infected cells exhibited 49±6% and 52±5% BrdU incorporation, respectively, an increase that is statistically highly significant (p=0.0002 and 0.00001 for heparanase vs. Vo and T5 vs. Vo, respectively), reflecting over 2-fold increase in cell proliferation (FIG. 4A, second panel, right). Similar results were also observed in heparanase- and T5-over expressing 293 cells (data not shown). Likewise, heparanase- and T5-silencing was associated with a comparable, ~50% decrease in BrdU incorporation (FIG. 4A, third panels).

Figure 4B:
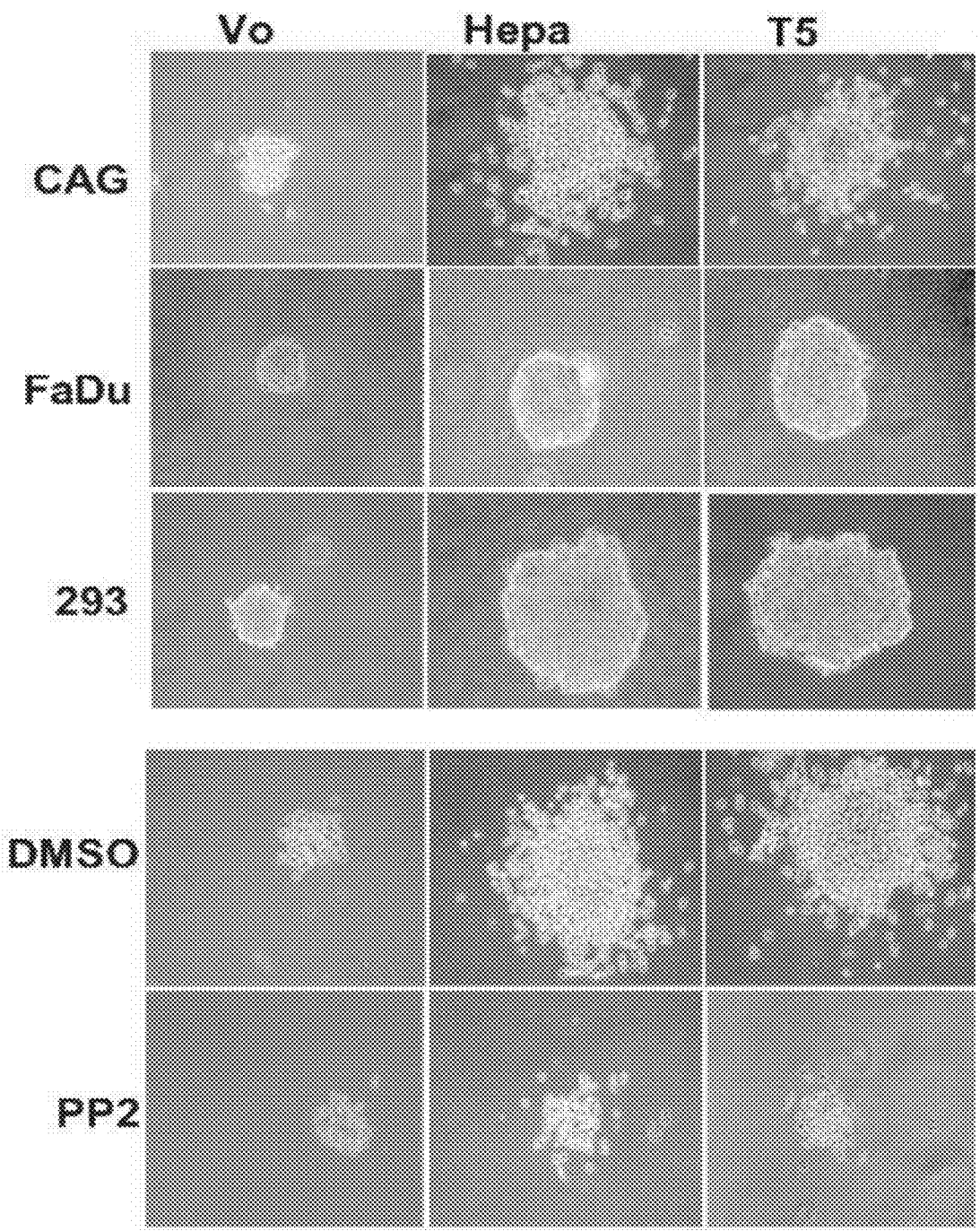
Figure 8:
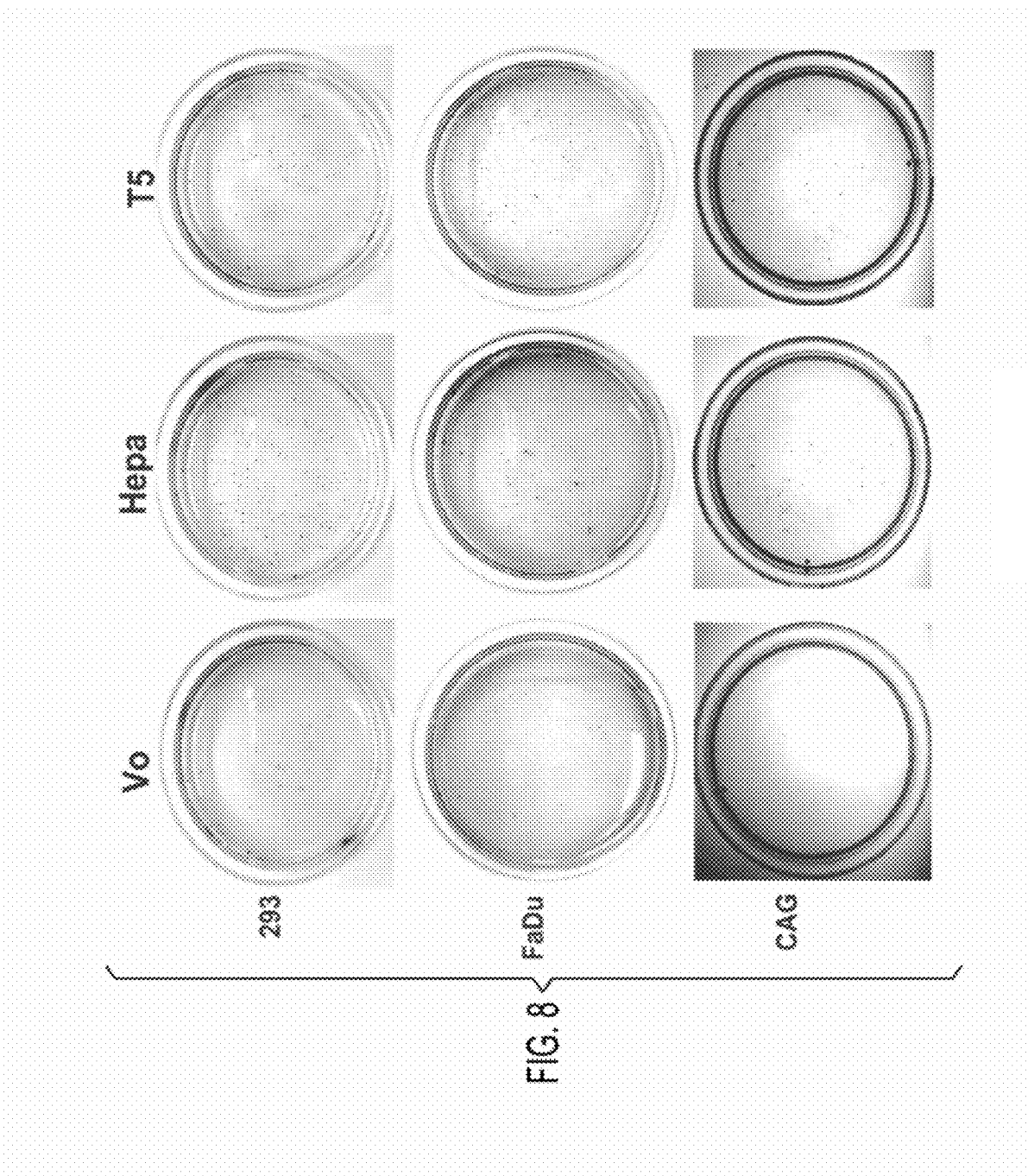
FIG. 8. T5 enhances colony formation in soft agar. Control (Vo), heparanase (Hepa)-, and T5-infected 293 (upper panels), FaDu (second panels) and CAG (lower panel) cells (5×10$^3$ cells/dish) were mixed with soft agar and cultured for 2-5 weeks. Shown are photomicrographs of the culture plates at their original size. Note increased colony number upon heparanase or T5 over expression.

The effect of heparanase and T5 on cell proliferation was further evaluated by monitoring cell growth and colony formation in soft agar (FIG. 4B; FIG. 8). Colony number (FIG. 8), size and cell density were markedly increased following heparanase or T5 over expression in CAG myeloma (FIG. 4B, upper panel), FaDu pharynx carcinoma (FIG. 4B, second panel) and 293 cells (FIG. 4B, third panel). Enhanced colony formation upon heparanase or T5 over expression appeared to be mediated by Src activation, because colonies formed in the presence of the Src inhibitor PP2 (FIG. 4B, fourth and fifth panels) as well as two additional Src inhibitors (PP1, Src inhibitor I; data not shown) were similar in shape and size to control colonies. Collectively, these findings strongly imply that heparanase and the T5 splice variant enhance cell proliferation and anchorage-independent cell growth by activating Src.

T5 Enhances Myeloma Xenograft Development.

Figure 5A:
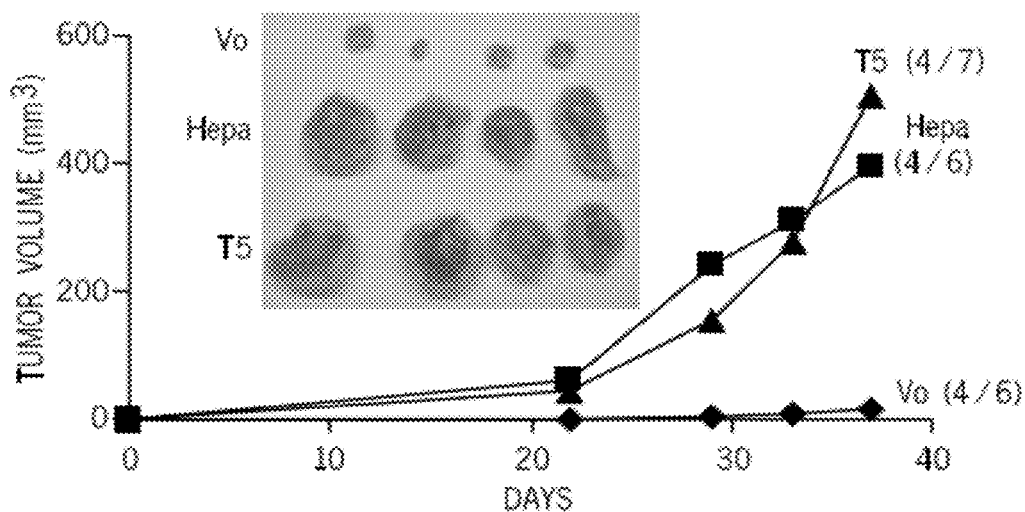
FIG. 5. T5 enhances tumor xenograft development. Control (Vo), heparanase-, and T5-infected CAG myeloma cells were injected subcutaneously (1×10$^6$/0.1 ml) and tumor volume was calculated (A). At the end of the experiment on day 37, tumors were resected, photographed (A, inset) and weighted (B). C. Immunohistochemical analysis. Paraffin-embedded 5 micron sections were stained with hematoxylin & eosin (left column), anti-CD31 (second left column), and anti-smooth muscle actin (SMA, two right columns) antibodies. Note increased blood vessels density and maturation (recruitment of SMA-positive cells) in xenografts produced by heparanase- and T5-infected cells.
Figure 9A:
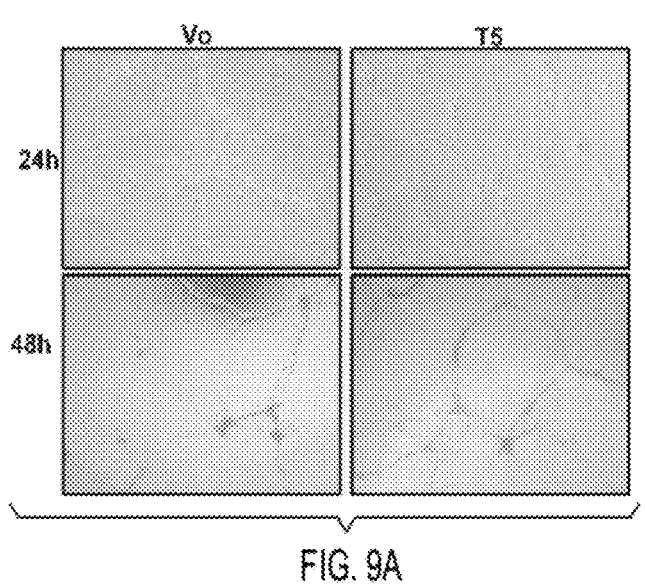
FIG. 9. A. Tube-like structure formation. Human umbilical vein endothelial cells (HUVEC) were infected with control (Vo) or T5 lenti virus constructs and plated on reconstituted basement membrane (Matrigel). Spontaneous organization into tube-like structures was examined after 24 h (upper panels) and 48 h (lower panels). Note network stabilization upon T5 over expression at 48 h. B Immunofluorescent staining of control (Vo), heparanase-, and T5-infected HUVEC cells applying anti-heparanase 733 antibody (green, left panels). Merged images with nuclear staining (Topro, red) are shown in the right panels. Note T5 localization to endocytic vesicles.

Having demonstrated a role for T5 in cell proliferation and colony formation, the potential role of T5 for enhancing tumor development was considered. Until day 21, xenografts produced by control (Vo)-, heparanase-, and T5-infected CAG myeloma cells exhibited similar growth rates upon subcutaneous inoculation into athymic nude mice (FIG. 5A). Thereafter, however, the development of tumor xenografts produced by heparanase- and T5-infected cells was markedly enhanced compared with xenografts generated by control cells (FIG. 5A). Upon termination of the experiment on day 37, noticeable differences in tumor xenograft development were observed (FIG. 5A, inset). Thus, average weight of control xenografts was 58±11 mg compared with 648±69 and 738±114 mg for heparanase and T5 xenografts, respectively, differences that are statistically highly significant (p=0.00007 and 0.0005 for heparanase vs. Vo and T5 vs. Vo, respectively). Next the micro vessel density was evaluated in the resulting CAG xenografts by immunohistochemical analysis of the endothelial cell marker, CD31. A two-fold increase in vessel density was found following heparanase over expression (FIG. 5C, CD31, Hepa), in agreement with previous studies utilizing this cell system (Kelly, T., Met al., 2003, Cancer Res 63, 8749-8756), and a similar elevation of vessel density was observed upon T5 over expression (FIG. 5C, CD31, T5). Not only vessel density but also vessel maturation was affected by heparanase and T5 over expression. Staining for smooth muscle actin which labels vessel-associated pericytes showed a significantly increased number of pericytes associated with blood vessels in xenografts produced by heparanase- and T5-infected CAG cells (FIG. 5C, SMA low), in agreement with previous findings. Closer examination revealed that while the pericyte coverage appeared discontinuous in xenografts produced by heparanase over expressing CAG cells (FIG. 5C, right most, Hepa), a dense pericyte layer surrounded even small capillaries following T5 over expression (FIG. 5C, right most, T5). The Pro-angiogenic feature of T5 was further concluded from endothelial cell organization (tube formation) on reconstituted basement membrane (Matrigel) that was maintained for a relatively long period of time vs. control (Vo) cells (FIG. 9A). These results suggest that enhanced xenograft progression is due, in part, to augmented tumor angiogenesis and blood vessel maturation.

T5 is Abundantly Expressed in Renal Cell Carcinoma.

Figure 6:
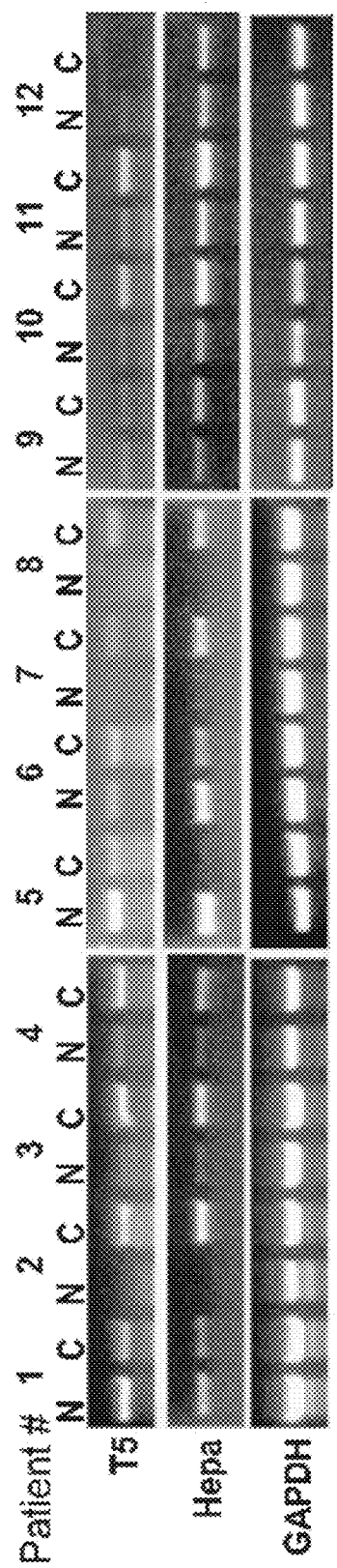
FIG. 6. Clinical relevance of T5. Total RNA was extracted from biopsies of renal cell carcinoma (C) and adjacent normal looking tissue (N) and subjected to RT-PCR analysis applying T5 (upper panel), heparanase (second panel) and GAPDH (lower panel) primers.

In order to investigate the clinical significance of T5, its expression in renal cell carcinoma biopsies was examined applying RT-PCR analysis (FIG. 6). T5 expression was readily observed in the carcinoma (C) samples and appeared to be elevated in 75% of the cases available for us (8/12) compared to the adjacent, normal-looking tissue (N). Moreover, renal cell carcinomas appeared to contain similar levels of heparanase and T5, suggesting that both wild type and spliced heparanase T5 contribute to the progression of this and likely other carcinomas.

Figure 5B:
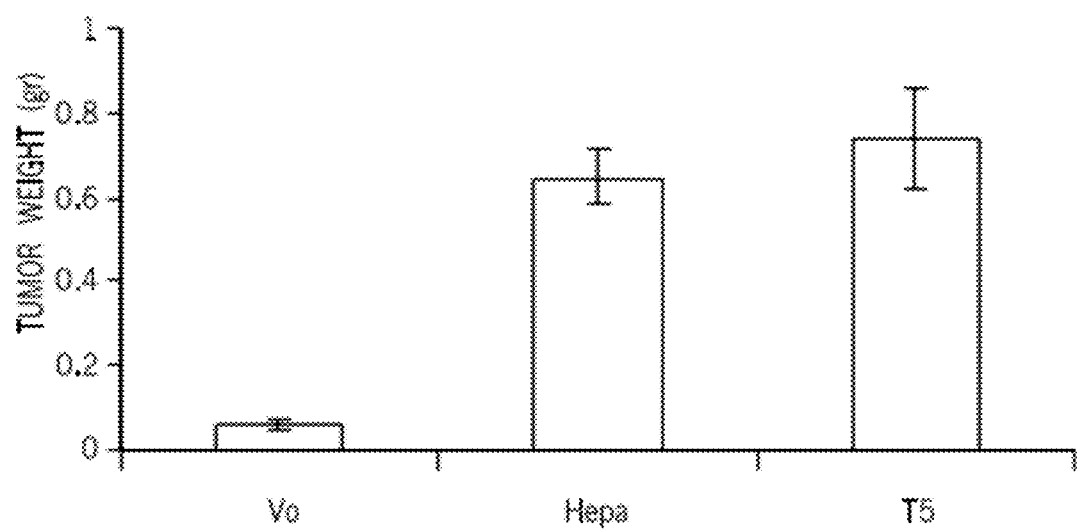
Figure 5C:
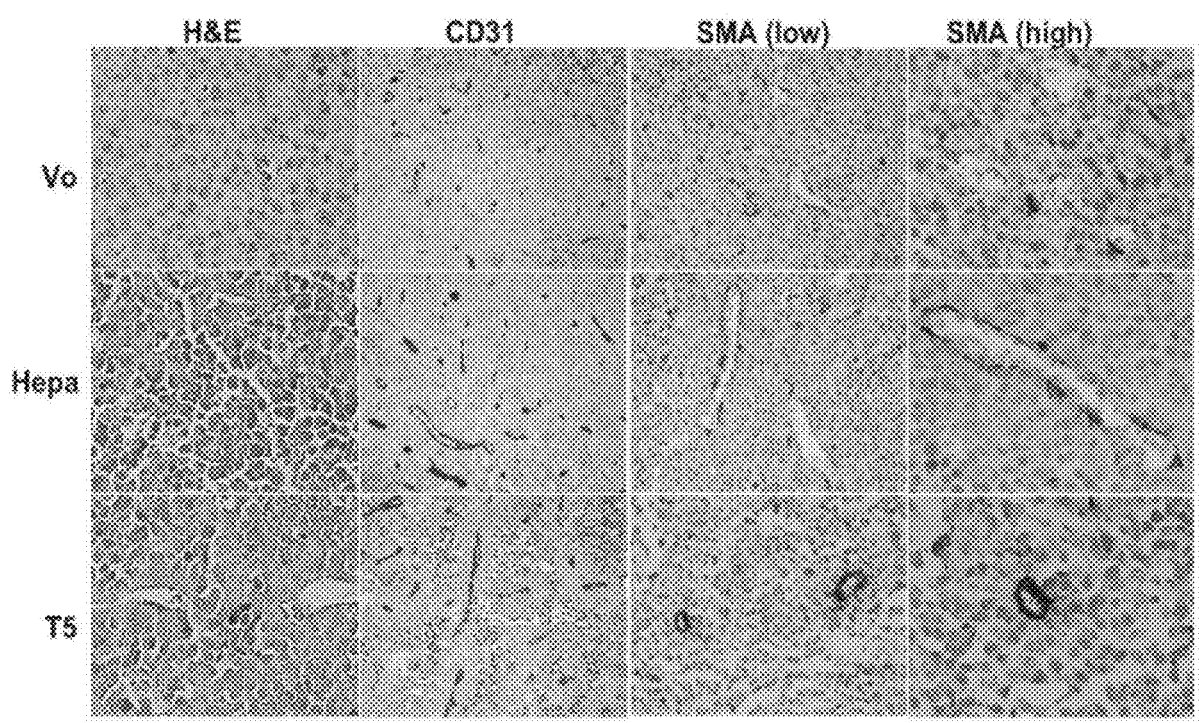

From the above results, clearly, the T5 splice variant is endowed with pro-tumorigenic properties, enhancing cell proliferation, anchorage independent growth and tumor xenograft development (FIGS. 4, 5). These features were observed in several tumor-derived cell lines over expressing T5, or following T5 gene silencing (FIGS. 3, 4), suggesting that its function is relevant to multiple tumor types. The clinical relevance of T5 critically emerged from analysis of renal cell carcinoma biopsies, where T5 and heparanase expression appeared to be induced in 75% of the cases (FIG. 6).

Compelling evidence indicate that heparanase expression is elevated in the vast majority of primary hematological and solid malignancies (Vreys, V., et al., 2007, *J Cell Mol Med* 11, 427-452; Ilan, N., et al., 2006, *Int J Biochem Cell Biol* 38, 2018-2039; Vlodaysky, I., et al., 2007, *Curr Pharm Des* 13, 2057-2073) yet the role that heparanase plays in primary tumor progression is incompletely understood. The discovery of the T5 splice variant provides another explanation for the pro-tumorigenic and pro-angiogenic properties of heparanase. This is because T5 is being expressed along with heparanase in tumor-derived cells (FIG. 2A) and in clinical specimens (FIG. 6) to comparable levels and appears to promote cell proliferation (FIG. 4A), colony formation (FIG. 4B), xenograft progression (FIG. 5A) and tumor angiogenesis (FIG. 5C). Thus, while inhibitors directed against the enzymatic activity of heparanase are currently evaluated in clinical trials (Fairweather, J. K., et al., 2008, Bioorganic & Medicinal Chem 16, 699-709; Ferro, V., et al., 2007, Seminars in Throm Hemost 33, 557-568), T5 as well as the heparanase C-domain responsible for enzymatic activity-independent functions of heparanase are not expected to be affected by these inhibitors. It appears therefore that a well defined enzymatic activity thought to be relatively easy to target, turned, at least in certain tumor systems, into a complex matter as more knowledge accumulates and the biology of the protein is revealed.

Figure 2D:
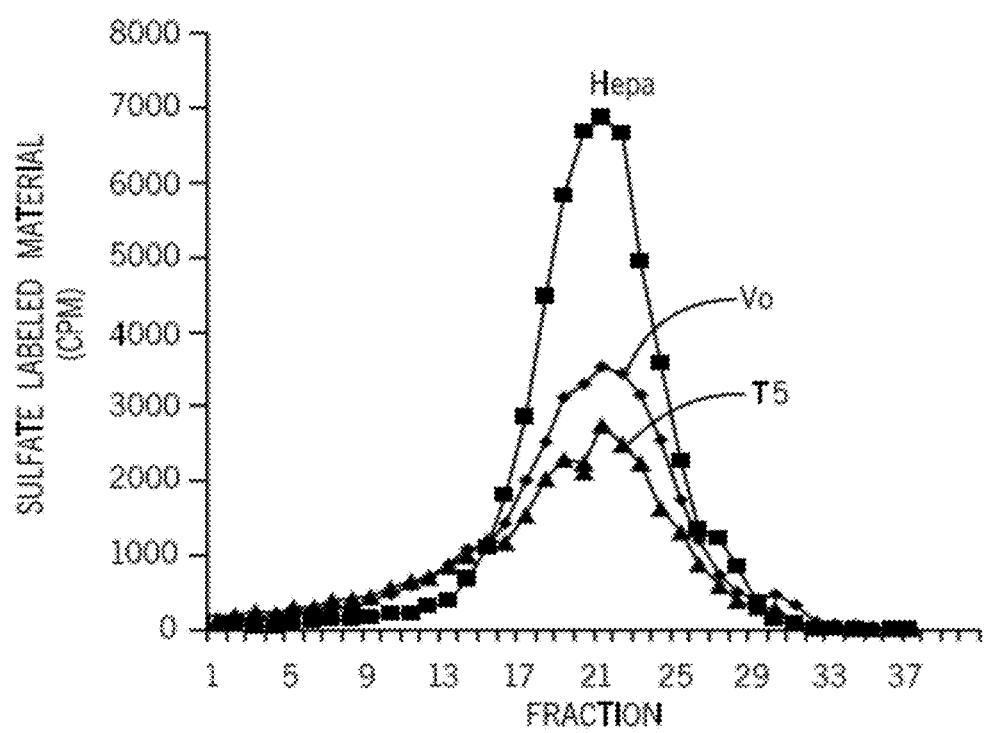

Heparanase and T5 share several biochemical characteristics. The signal peptide of heparanase is retained in T5, enabling its delivery to the ER and Golgi apparatus (FIG. 2C), glycosylation (evident by sensitivity to Tunicamycin and binding to Con A; FIG. 2B, FIG. 7A), and secretion (FIG. 2B). Protein N-glycosylation likely occurs on a single asparagine residue ($Asn^{162}$) preserved in T5 and shown to be required for protein secretion. Not surprisingly, T5 is devoid of heparanase enzymatic activity, nor did it compete with the endogenous heparanase activity (FIG. 2D). This is largely because T5 is incapable of heparin binding (FIG. 7). Although the basic heparin binding domain of heparanase ($Lys^{158}$-$Asn^{162}$) is retained in T5 and is followed by additional positively-charged amino acids (KK) thought to create an even more potent heparin binding domain, T5 failed to interact with heparin (FIG. 7A). Similarly, a peptide corresponding to this sequence including the unique amino acids introduced in T5 (CKKK; FIG. 7B) failed to interact with heparin and to inhibit heparanase enzymatic activity, as opposed to the KKDC peptide which efficiently accomplished both tasks (FIG. 7B, C). Thus, the mere presence of Cardin-Weintraub consensus sequence appears insufficient to ensure high affinity binding to heparin and neighboring amino acids dictate the functional outcome.

Src activation by T5 can not be therefore explained by interaction with HS and/or clustering of syndecans. The rational behind this function is likely structural. According to this notion, the alternative splicing generated a truncated protein that acquired a novel conformation not normally present in the heparanase molecule.

Figure 9B:
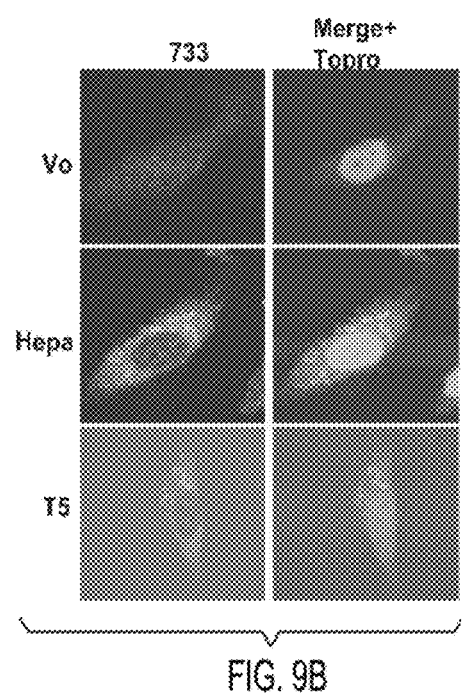

Interestingly, heparanase and T5 appear to be localized in endocytic vesicles (FIG. 9B). While heparanase is subjected to cellular uptake together with syndecans and accumulates in the lysosomal compartment (Gingis-Velitski, S., et al., 2004, J Biol Chem 279, 44084-44092; Goldshmidt, O., et al., 2002, Exp Cell Res 281, 50-62.) where it undergoes proteolytic processing by cathepsin L (Abboud-Jarrous, et al., 2005, J Biol Chem 280, 13568-13575; Cohen, E., et al., 2005, FEBS Lett 579, 2334-2338), T5 does not interacts with HS. Its delivery to endocytic vesicles is therefore likely mediated by interaction with other cell surface molecule(s) responsible for its signaling and pro-tumorigenic properties.

These data together demonstrate that a functional splice variant of heparanase has been discovered through Compugen's LEADS platform. The T5 splice variant possesses pro-tumorigenic properties, facilitating cell proliferation, colony formation and tumor xenograft development. Furthermore, T5 is expressed in the majority of renal cell carcinoma biopsies examined, strongly supporting the clinical relevance of this protein variant. T5 appears therefore as a valid target for the development of anti-cancer drugs, introducing another level of complexity to the heparanase field and the attempts to neutralize its growing repertoire of biological activities.

EXAMPLE 2

The Skip 10 Variant is Expressed in Cervical Cancer Cell Line (HeLa) and in Testis An RT PCR reaction was conducted on RNA extracted from selected tissue samples and cell lines (FIG. 10). The reaction used the following primers: F—GTATTGGA-CATTTTTATTTCATCTGTGC (SEQ ID NO:13) and R—GGTGTTAATGGCAAGCGTGC (SEQ ID NO:14) and was done at standard RT-PCR conditions using the annealing temperature of 620 C. Experssion of the WT Heparanase product (Normal) was found in all tested tissues but was not found in a mixure of assorte4d cell lines (lane 14). However, expression was very low in Pancreas (lane 7). The skip 10 variant was found in two samples: the Cervical cancer cell line (HeLa—Lane 1) and Testis (Lane 11) and was found to be correlated with the level of wt expression (marked by arrows). Bands marked by written numbers (1 and 2 on the gel figure) were taken for sequencing (Sanger) which confirmed band 1 to be the wild-type and band 2 to be the skip 10 variant.

EXAMPLE 3

General Aspects of at Least Some Embodiments of the Present Invention

Nucleic Acids

A "nucleic acid fragment" or an "oligonucleotide" or a "polynucleotide" are used herein interchangeably to refer to a polymer of nucleic acid residues. A polynucleotide sequence according to at least some embodiments of the present invention refers to a single or double stranded nucleic acid sequences which is isolated and provided in the form of an RNA sequence, a complementary polynucleotide sequence (cDNA), a genomic polynucleotide sequence and/ or a composite polynucleotide sequences (e.g., a combination of the above).

Thus, the present invention encompasses nucleic acid sequences described hereinabove; fragments thereof, sequences hybridizable therewith, sequences homologous thereto [e.g., at least 90%, at least 95, 96, 97, 98 or 99% or more identical to the nucleic acid sequences set forth herein], sequences encoding similar polypeptides with different codon usage, altered sequences characterized by mutations, such as deletion, insertion or substitution of one or more nucleotides, either naturally occurring or man induced, either randomly or in a targeted fashion. The present invention also encompasses homologous nucleic acid sequences (i.e., which form a part of a polynucleotide sequence according to at least some embodiments of the present invention), which include sequence regions unique to the polynucleotides according to at least some embodiments of the present invention.

In cases where the polynucleotide sequences according to at least some embodiments of the present invention encode previously unidentified polypeptides, the present invention also encompasses novel polypeptides or portions thereof, which are encoded by the isolated polynucleotide and respective nucleic acid fragments thereof described hereinabove.

Thus, the present invention also encompasses polypeptides encoded by the polynucleotide sequences according to at least some embodiments of the present invention. The present invention also encompasses homologues of these polypeptides, such homologues can be at least 90%, at least 95, 96, 97, 98 or 99% or more homologous to the amino acid sequences set forth below, as can be determined using BlastP software of the National Center of Biotechnology Information (NCBI) using default parameters. Finally, the present invention also encompasses fragments of the above described polypeptides and polypeptides having mutations, such as deletions, insertions or substitutions of one or more amino acids, either naturally occurring or man induced, either randomly or in a targeted fashion.

Oligonucleotides designed for carrying out the methods according to at least some embodiments of the present invention for any of the sequences provided herein (designed as described above) can be generated according to any oligonucleotide synthesis method known in the art such as enzymatic synthesis or solid phase synthesis. Equipment and reagents for executing solid-phase synthesis are commercially available from, for example, Applied Biosystems. Any other means for such synthesis may also be employed; the actual synthesis of the oligonucleotides is well within the capabilities of one skilled in the art.

Oligonucleotides used according to this aspect according to at least some embodiments of the present invention are those having a length selected from a range of about 10 to about 200 bases, optionally about 15 to about 150 bases, about 20 to about 100 bases, or about 20 to about 50 bases.

The oligonucleotides according to at least some embodiments of the present invention may comprise heterocyclic nucleosides consisting of purines and the pyrimidines bases, bonded in a 3' to 5' phosphodiester linkage.

Peptides

The terms "polypeptide," "peptide" and "protein" are used interchangeably herein to refer to a polymer of amino acid residues. The terms apply to amino acid polymers in which one or more amino acid residue is an analog or mimetic of a corresponding naturally occurring amino acid, as well as to naturally occurring amino acid polymers. Polypeptides can be modified, e.g., by the addition of carbohydrate residues to form glycoproteins. The terms "polypeptide," "peptide" and "protein" include glycoproteins, as well as non-glycoproteins.

Polypeptide products can be biochemically synthesized such as by employing standard solid phase techniques. Such methods include exclusive solid phase synthesis, partial solid phase synthesis methods, fragment condensation, classical solution synthesis. These methods are optionally used when the peptide is relatively short (i.e., 10 kDa) and/or when it cannot be produced by recombinant techniques (i.e., not encoded by a nucleic acid sequence) and therefore involves different chemistry.

Solid phase polypeptide synthesis procedures are well known in the art and further described by John Morrow Stewart and Janis Dillaha Young, Solid Phase Peptide Syntheses (2nd Ed., Pierce Chemical Company, 1984).

Synthetic polypeptides can be purified by preparative high performance liquid chromatography [Creighton T. (1983) Proteins, structures and molecular principles. WH Freeman and Co. N.Y.] and the composition of which can be confirmed via amino acid sequencing.

In cases where large amounts of a polypeptide are desired, it can be generated using recombinant techniques such as described by Bitter et al., (1987) Methods in Enzymol. 153:516-544, Studier et al. (1990) Methods in Enzymol. 185:60-89, Brisson et al. (1984) Nature 310:511-514, Takamatsu et al. (1987) EMBO J. 6:307-311, Coruzzi et al. (1984) EMBO J. 3:1671-1680 and Brogli et al., (1984) Science 224:838-843, Gurley et al. (1986) Mol. Cell. Biol. 6:559-565 and Weissbach & Weissbach, 1988, Methods for Plant Molecular Biology, Academic Press, NY, Section VIII, pp 421-463.

It will be appreciated that peptides according to at least some embodiments of the present invention may be degradation products, synthetic peptides or recombinant peptides as well as peptidomimetics, typically, synthetic peptides and peptoids and semipeptoids which are peptide analogs, which may have, for example, modifications rendering the peptides more stable while in a body or more capable of penetrating into cells. Such modifications include, but are not limited to N terminus modification, C terminus modification, peptide bond modification, including, but not limited to, CH2-NH, CH2-S, CH2-S=O, O=C—NH, CH2-O, CH2-CH2, S=C—NH, CH=CH or CF=CH, backbone modifications, and residue modification. Methods for preparing peptidomimetic compounds are well known in the art and are specified, for example, in Quantitative Drug Design, C A Ramsden Gd., Chapter 17.2, F. Choplin Pergamon Press (1992), which is incorporated by reference as if fully set forth herein. Further details in this respect are provided hereinunder.

Peptide bonds (—CO—NH—) within the peptide may be substituted, for example, by N-methylated bonds (—N(CH3)-CO—), ester bonds (—C(R)H—C—O—O—C(R)—N—), ketomethylen bonds (—CO—CH2-), α-aza bonds (—NH—N(R)—CO—), wherein R is any alkyl, e.g., methyl, carba bonds (—CH2-NH—), hydroxyethylene bonds (—CH(OH)—CH2-), thioamide bonds (—CS—NH—), olefinic double bonds (—CH=CH—), retro amide bonds (—NH—CO—), peptide derivatives (—N(R)—CH2-CO—), wherein R is the "normal" side chain, naturally presented on the carbon atom.

These modifications can occur at any of the bonds along the peptide chain and even at several (2-3) at the same time.

Natural aromatic amino acids, Trp, Tyr and Phe, may be substituted by synthetic non-natural acid such as Phenylglycine, TIC, naphthylelanine (Nol), ring-methylated derivatives of Phe, halogenated derivatives of Phe or o-methyl-Tyr.

In addition to the above, the peptides according to at least some embodiments of the present invention may also include one or more modified amino acids or one or more non-amino acid monomers (e.g. fatty acids, complex carbohydrates etc).

As used herein in the specification and in the claims section below the term "amino acid" or "amino acids" is understood to include the 20 naturally occurring amino acids; those amino acids often modified post-translationally in vivo, including, for example, hydroxyproline, phosphoserine and phosphothreonine; and other unusual amino acids including, but not limited to, 2-aminoadipic acid, hydroxylysine, isodesmosine, nor-valine, nor-leucine and ornithine. Furthermore, the term "amino acid" includes both D- and L-amino acids.

The peptides according to at least some embodiments of the present invention might include one or more non-natural or natural polar amino acids, including but not limited to serine and threonine which are capable of increasing peptide solubility due to their hydroxyl-containing side chain.

The peptides according to at least some embodiments of the present invention can be biochemically synthesized such as by using standard solid phase techniques. These methods include exclusive solid phase synthesis, partial solid phase synthesis methods, fragment condensation, classical solution synthesis. These methods are optionally used when the peptide is relatively short (i.e., 10 kDa) and/or when it cannot be produced by recombinant techniques (i.e., not encoded by a nucleic acid sequence) and therefore involves different chemistry.

Solid phase peptide synthesis procedures are well known in the art and further described by John Morrow Stewart and Janis Dillaha Young, Solid Phase Peptide Syntheses (2nd Ed., Pierce Chemical Company, 1984).

Synthetic peptides can be purified by preparative high performance liquid chromatography [Creighton T. (1983) Proteins, structures and molecular principles. WH Freeman and Co. N.Y.] and the composition of which can be confirmed via amino acid sequencing.

In cases where large amounts of the peptides according to at least some embodiments of the present invention are desired, the peptides can be generated using recombinant techniques such as described by Bitter et al., (1987) Methods in Enzymol. 153:516-544, Studier et al. (1990) Methods in Enzymol. 185:60-89, Brisson et al. (1984) Nature 310:511-514, Takamatsu et al. (1987) EMBO J. 6:307-311, Coruzzi et al. (1984) EMBO J. 3:1671-1680 and Brogli et al., (1984) Science 224:838-843, Gurley et al. (1986) Mol. Cell. Biol. 6:559-565 and Weissbach & Weissbach, 1988, Methods for Plant Molecular Biology, Academic Press, NY, Section VIII, pp 421-463.

Recombinant Expression of Polypeptides

Methods for introduction of heterologous polynucleotides into mammalian cells are well known in the art and include dextran-mediated transfection, calcium phosphate precipitation, polybrene-mediated transfection, protoplast fusion, electroporation, encapsulation of the polynucleotide(s) in liposomes, biolistic injection and direct microinjection of the DNA into nuclei. In addition, nucleic acid molecules may be introduced into mammalian cells by viral vectors. Methods of transforming cells are well known in the art. See, e.g., U.S. Pat. Nos. 4,399,216, 4,912,040, 4,740,461, and 4,959,455 (which patents are hereby incorporated herein by reference). Methods of transforming plant cells are well known in the art, including, e.g., *Agrobacterium*-mediated transformation, biolistic transformation, direct injection, electroporation and viral transformation. Methods of transforming bacterial and yeast cells are also well known in the art.

Mammalian cell lines available as hosts for expression are well known in the art and include many immortalized cell lines available from e.g. the American Type Culture Collection (ATCC). These include, inter alia, Chinese hamster ovary (CHO) cells, NS0, SP2 cells, HEK-293T cells, NIH-3T3 cells, HeLa cells, baby hamster kidney (BHK) cells, monkey kidney cells (COS), human hepatocellular carcinoma cells (e.g., Hep G2), A549 cells, 3T3 cells, and a number of other cell lines. Mammalian host cells include human, mouse, rat, dog, monkey, pig, goat, bovine, horse and hamster cells. Cell lines of particular preference are selected through determining which cell lines have high expression levels. Other cell lines that may be used are insect cell lines, such as Sf9 cells, amphibian cells, bacterial cells, plant cells and fungal cells. When recombinant expression vectors encoding the polypeptides according to at least some embodiments of the invention or fragments thereof are introduced into mammalian host cells, the polypeptides are produced by culturing the host cells for a period of time sufficient to allow for expression of the polypeptide in the host cells or, more preferably, secretion of the polypeptide into the culture medium in which the host cells are grown. Polypeptides can be recovered from the culture medium using standard protein purification methods. Plant host cells include, e.g., *Nicotiana, Arabidopsis*, duckweed, corn, wheat, potato, etc. Bacterial host cells include *E. coli* and *Streptomyces* species. Yeast host cells include *Schizosaccharomyces pombe, Saccharomyces cerevisiae* and *Pichia pastoris*.

Further, expression of the polypeptides according to at least some embodiments of the invention (or other moieties derived therefrom) from production cell lines can be enhanced using a number of known techniques. For example, the glutamine synthetase gene expression system (the GS system) is a common approach for enhancing expression under certain conditions. The GS system is discussed in whole or part in connection with European Patent Nos. 0 216 846, 0 256 055, 0 338 841 and 0 323 997.

It is likely that polypeptides expressed by different cell lines or in transgenic animals will have different glycosylation patterns. However, all polypeptides encoded by the nucleic acid molecules provided herein, or comprising the amino acid sequences provided herein are part of the instant invention, regardless of their glycosylation pattern.

Vectors

According to at least some embodiments, the invention provides vectors comprising the nucleic acid molecules that encode the polypeptides, fusion proteins, modified polypeptides, and polypeptide fragments of at least some embodiments the invention.

To express the polypeptides according to at least some embodiments of the invention, or fragments thereof, DNAs encoding partial or full-length polypeptides, obtained as described above, are inserted into expression vectors such that the genes are operatively linked to transcriptional and translational control sequences. Expression vectors include plasmids, retroviruses, adenoviruses, adeno-associated viruses (AAV), plant viruses such as cauliflower mosaic virus, tobacco mosaic virus, cosmids, YACs, EBV derived episomes, and the like. The gene is ligated into a vector such that transcriptional and translational control sequences within the vector serve their intended function of regulating the transcription and translation of the gene. The expression vector and expression control sequences are chosen to be compatible with the expression host cell used. The gene is inserted into the expression vector by standard methods (e.g., ligation of complementary restriction sites on the gene fragment and vector, or blunt end ligation if no restriction sites are present).

A convenient vector is one that encodes a functionally complete sequence, with appropriate restriction sites engineered so that any sequence can be easily inserted and expressed, as described above. Polyadenylation and transcription termination occur at native chromosomal sites downstream of the coding regions. The recombinant expression vector can also encode a signal peptide that facilitates secretion of the polypeptide from a host cell. The gene may be cloned into the vector such that the signal peptide is linked in-frame to the amino terminus of the gene.

In addition to the nucleic acid according to at least some embodiments of the invention, the recombinant expression vectors carry regulatory sequences that control the expression of the gene in a host cell. It will be appreciated by those skilled in the art that the design of the expression vector, including the selection of regulatory sequences may depend on such factors as the choice of the host cell to be transformed, the level of expression of protein desired, etc. Preferred regulatory sequences for mammalian host cell expression include viral elements that direct high levels of protein expression in mammalian cells, such as promoters and/or enhancers derived from retroviral LTRs, cytomegalovirus (CMV) (such as the CMV promoter/enhancer), Simian Virus 40 (SV40) (such as the SV40 promoter/enhancer), adenovirus, (e.g., the adenovirus major late promoter (AdMLP)), polyoma and strong mammalian promoters such as native immunoglobulin and actin promoters. For further description of viral regulatory elements, and sequences thereof, see e.g., U.S. Pat. Nos. 5,168,062, 4,510,245, and 4,968,615, each of which is hereby incorporated by reference. Methods of expressing polypeptides in bacterial cells or fungal cells, e.g., yeast cells, are also well known in the art.

In addition to the nucleic acids according to at least some embodiments of the invention and regulatory sequences, the recombinant expression vectors according to at least some embodiments of the invention may carry additional sequences, such as sequences that regulate replication of the vector in host cells (e.g., origins of replication) and selectable marker genes. The selectable marker gene facilitates selection of host cells into which the vector has been introduced (see, e.g., U.S. Pat. Nos. 4,399,216, 4,634,665 and 5,179,017). For example, typically the selectable marker gene confers resistance to drugs, such as G418, hygromycin or methotrexate, on a host cell into which the vector has been introduced. Preferred selectable marker genes include the dihydrofolate reductase (DHFR) gene, the neo gene (for G418 selection), and the glutamate synthetase gene.

Protein Modifications

Fusion Proteins

The present invention encompasses fusion proteins (conjugates) for use in therapy, comprising any of the T4, T5 or "skip 10" proteins or portions thereof fused to heterologous sequence as described herein. The invention contemplates the use thereof for treating cancer as described herein.

By heterologous sequence it is meant any peptide which is not included in any of T5, T4, or skip 10 variants, or SEQ ID NO:11.

According to at least some embodiments, a fusion protein may be prepared from a protein according to at least some embodiments of the invention by fusion with a portion of an immunoglobulin comprising a constant region of an immunoglobulin. Optionally, the portion of the immunoglobulin comprises a heavy chain constant region which is optionally and more preferably a human heavy chain constant region. The heavy chain constant region is optionally an IgG heavy chain constant region, and optionally an Fc chain, or an IgG Fc fragment that comprises CH2 and CH3 domains. Although any IgG subtype may optionally be used, the IgG1 subtype is preferred. The Fc chain may optionally be a known or "wild type" Fc chain, or alternatively may be mutated. Non-limiting, illustrative, exemplary types of mutations are described in US Patent Application No. 20060034852, published on Feb. 16, 2006, hereby incorporated by reference as if fully set forth herein. The term "Fc chain" also optionally comprises any type of Fc fragment.

Several of the specific amino acid residues that are important for antibody constant region-mediated activity in the IgG subclass have been identified. Inclusion, substitution or exclusion of these specific amino acids therefore allows for inclusion or exclusion of specific immunoglobulin constant region-mediated activity. Furthermore, specific changes may result in aglycosylation for example and/or other desired changes to the Fc chain. At least some changes may optionally be made to block a function of Fc which is considered to be undesirable, such as an undesirable immune system effect, as described in greater detail below.

Non-limiting, illustrative examples of mutations to Fc which may be made to modulate the activity of the fusion protein include the following changes (given with regard to the Fc sequence nomenclature as given by Kabat, from Kabat E A et al: Sequences of Proteins of Immunological Interest. US Department of Health and Human Services, NIH, 1991): 220 C→S; 233-238 ELLGGP→EAEGAP; 265D→A, preferably in combination with 434N→A; 297N→A (for example to block N-glycosylation); 318-322 EYKCK→AYACA; 330-331AP→SS; or a combination thereof (see for example M. Clark, "Chemical Immunol and Antibody Engineering", pp 1-31 for a description of these mutations and their effect). The construct for the Fc chain which features the above changes optionally and preferably comprises a combination of the hinge region with the CH2 and CH3 domains.

The above mutations may optionally be implemented to enhance desired properties or alternatively to block non-desired properties. For example, aglycosylation of antibodies was shown to maintain the desired binding functionality while blocking depletion of T-cells or triggering cytokine release, which may optionally be undesired functions (see M. Clark, "Chemical Immunol and Antibody Engineering", pp 1-31). Substitution of 331 proline for serine may block the ability to activate complement, which may optionally be considered an undesired function (see M. Clark, "Chemical Immunol and Antibody Engineering", pp 1-31). Changing 330 alanine to serine in combination with this change may also enhance the desired effect of blocking the ability to activate complement.

Residues 235 and 237 were shown to be involved in antibody-dependent cell-mediated cytotoxicity (ADCC), such that changing the block of residues from 233-238 as described may also block such activity if ADCC is considered to be an undesirable function.

Residue 220 is normally a cysteine for Fc from IgG1, which is the site at which the heavy chain forms a covalent linkage with the light chain. Optionally, this residue may be changed to a serine, to avoid any type of covalent linkage (see M. Clark, "Chemical Immunol and Antibody Engineering", pp 1-31).

The above changes to residues 265 and 434 may optionally be implemented to reduce or block binding to the Fc receptor, which may optionally block undesired functionality of Fc related to its immune system functions (see "Binding site on Human IgG1 for Fc Receptors", Shields et al, Vol 276, pp 6591-6604, 2001).

The above changes are intended as illustrations only of optional changes and are not meant to be limiting in any way. Furthermore, the above explanation is provided for descriptive purposes only, without wishing to be bound by a single hypothesis.

According to at least some embodiments, the present invention provides a chimeric molecule featuring a polypeptide according to any variant protein as described herein joined to a heterologous polypeptide, wherein said heterologous polypeptide comprises an immunoglobulin heavy chain constant region corresponding to an antibody isotype selected from the group consisting of an IgG1, IgG2, IgG3, IgG4, IgM, IgE, IgA and IgD.

Addition of Groups

If a protein according to the present invention is a linear molecule, it is possible to place various functional groups at various points on the linear molecule which are susceptible to or suitable for chemical modification. Functional groups can be added to the termini of linear forms of the protein according to at least some embodiments of the invention. In some embodiments, the functional groups improve the activity of the protein with regard to one or more characteristics, including but not limited to, improvement in stability, penetration (through cellular membranes and/or tissue barriers), tissue localization, efficacy, decreased clearance, decreased toxicity, improved selectivity, improved resistance to expulsion by cellular pumps, and the like. For convenience sake and without wishing to be limiting, the free N-terminus of one of the sequences contained in the compositions according to at least some embodiments of the composition will be termed as the N-terminus of the composition, and the free C-terminal of the sequence will be considered as the C-terminus of the composition. Either the C-terminus or the N-terminus of the sequences, or both, can be linked to a carboxylic acid functional groups or an amine functional group, respectively.

Non-limiting examples of suitable functional groups are described in Green and Wuts, "Protecting Groups in Organic Synthesis", John Wiley and Sons, Chapters 5 and 7, 1991, the teachings of which are incorporated herein by reference. Preferred protecting groups are those that facilitate transport of the active ingredient attached thereto into a cell, for example, by reducing the hydrophilicity and increasing the lipophilicity of the active ingredient, these being an example for "a moiety for transport across cellular membranes".

These moieties can optionally be cleaved in vivo, either by hydrolysis or enzymatically, inside the cell. (Ditter et al., J. Pharm. Sci. 57:783 (1968); Ditter et al., J. Pharm. Sci. 57:828 (1968); Ditter et al., J. Pharm. Sci. 58:557 (1969); King et al., Biochemistry 26:2294 (1987); Lindberg et al., Drug Metabolism and Disposition 17:311 (1989); and Tunek et al., Biochem. Pharm. 37:3867 (1988), Anderson et al., Arch. Biochem. Biophys. 239:538 (1985) and Singhal et al., FASEB J. 1:220 (1987)). Hydroxyl protecting groups include esters, carbonates and carbamate protecting groups. Amine protecting groups include alkoxy and aryloxy carbonyl groups, as described above for N-terminal protecting groups. Carboxylic acid protecting groups include aliphatic, benzylic and aryl esters, as described above for C-terminal protecting groups. In one embodiment, the carboxylic acid group in the side chain of one or more glutamic acid or aspartic acid residue in a composition according to at least some embodiments of the present invention is protected, optionally with a methyl, ethyl, benzyl or substituted benzyl ester.

Non-limiting, illustrative examples of N-terminal protecting groups include acyl groups (—CO—R1) and alkoxy carbonyl or aryloxy carbonyl groups (—CO—O—R1), wherein R1 is an aliphatic, substituted aliphatic, benzyl, substituted benzyl, aromatic or a substituted aromatic group. Specific examples of acyl groups include but are not limited to acetyl, (ethyl)-CO—, n-propyl-CO—, iso-propyl-CO—, n-butyl-CO—, sec-butyl-CO—, t-butyl-CO—, hexyl, lauroyl, palmitoyl, myristoyl, stearyl, oleoyl phenyl-CO—, substituted phenyl-CO—, benzyl-CO— and (substituted benzyl)-CO—. Examples of alkoxy carbonyl and aryloxy carbonyl groups include CH3-O—CO—, (ethyl)-O—CO—, n-propyl-O—CO—, iso-propyl-O—CO—, n-butyl-O—CO—, sec-butyl-O—CO—, t-butyl-O—CO—, phenyl-O—CO—, substituted phenyl-O—CO— and benzyl-O—CO—, (substituted benzyl)-O—CO—, Adamantan, naphtalen, myristoleyl, toluen, biphenyl, cinnamoyl, nitrobenzoy, toluoyl, furoyl, benzoyl, cyclohexane, norbornane, or Z-caproic. In order to facilitate the N-acylation, one to four glycine residues can be present in the N-terminus of the molecule.

The carboxyl group at the C-terminus of the compound can be protected, for example, by a group including but not limited to an amide (i.e., the hydroxyl group at the C-terminus is replaced with —NH$_2$, —NHR$_2$ and —NR$_2$R$_3$) or ester (i.e. the hydroxyl group at the C-terminus is replaced with —OR$_2$). R$_2$ and R$_3$ are optionally independently an aliphatic, substituted aliphatic, benzyl, substituted benzyl, aryl or a substituted aryl group. In addition, taken together with the nitrogen atom, R$_2$ and R$_3$ can optionally form a C4 to C8 heterocyclic ring with from about 0-2 additional heteroatoms such as nitrogen, oxygen or sulfur. Non-limiting suitable examples of suitable heterocyclic rings include piperidinyl, pyrrolidinyl, morpholino, thiomorpholino or piperazinyl. Examples of C-terminal protecting groups include but are not limited to —NH$_2$, —NHCH 3, —N(CH$_3$)$_2$, —NH(ethyl), —N(ethyl)$_2$, —N(methyl) (ethyl), —NH(benzyl), —N(C1-C4 alkyl)(benzyl), —NH (phenyl), —N(C1-C4 alkyl) (phenyl), —OCH$_3$, —O-(ethyl), —O-(n-propyl), —O-(n-butyl), —O-(iso-propyl), —O-(sec-butyl), —O-(t-butyl), —O-benzyl and —O-phenyl.

Substitution by Peptidomimetic Moieties

A "peptidomimetic organic moiety" can optionally be substituted for amino acid residues in the composition of this invention both as conservative and as non-conservative substitutions. These moieties are also termed "non-natural amino acids" and may optionally replace amino acid residues, amino acids or act as spacer groups within the peptides in lieu of deleted amino acids. The peptidomimetic organic moieties optionally have steric, electronic or configurational properties similar to the replaced amino acid and such peptidomimetics are used to replace amino acids in the essential positions, and are considered conservative substitutions. However such similarities are not necessarily required. According to at least some embodiments of the present invention, one or more peptidomimetics are selected such that the composition at least substantially retains its physiological activity as compared to the native protein according to the present invention.

Peptidomimetics may optionally be used to inhibit degradation of the peptides by enzymatic or other degradative processes. The peptidomimetics can optionally be produced by organic synthetic techniques. Non-limiting examples of suitable peptidomimetics include D amino acids of the corresponding L amino acids, tetrazol (Zabrocki et al., J. Am. Chem. Soc. 110:5875-5880 (1988)); isosteres of amide bonds (Jones et al., Tetrahedron Lett. 29: 3853-3856 (1988)); LL-3-amino-2-propenidone-6-carboxylic acid (LL-Acp) (Kemp et al., J. Org. Chem. 50:5834-5838 (1985)). Similar analogs are shown in Kemp et al., Tetrahedron Lett. 29:5081-5082 (1988) as well as Kemp et al., Tetrahedron Lett. 29:5057-5060 (1988), Kemp et al., Tetrahedron Lett. 29:4935-4938 (1988) and Kemp et al., J. Org. Chem. 54:109-115 (1987). Other suitable but exemplary peptidomimetics are shown in Nagai and Sato, Tetrahedron Lett. 26:647-650 (1985); Di Maio et al., J. Chem. Soc. Perkin Trans., 1687 (1985); Kahn et al., Tetrahedron Lett. 30:2317

(1989); Olson et al., J. Am. Chem. Soc. 112:323-333 (1990); Garvey et al., J. Org. Chem. 56:436 (1990). Further suitable exemplary peptidomimetics include hydroxy-1,2,3,4-tetrahydroisoquinoline-3-carboxylate (Miyake et al., J. Takeda Res. Labs 43:53-76 (1989)); 1,2,3,4-tetrahydro-isoquinoline-3-carboxylate (Kazmierski et al., J. Am. Chem. Soc. 133:2275-2283 (1991)); histidine isoquinolone carboxylic acid (HIC) (Zechel et al., Int. J. Pep. Protein Res. 43 (1991)); (2S, 3S)-methyl-phenylalanine, (2S, 3R)-methyl-phenylalanine, (2R, 3S)-methyl-phenylalanine and (2R, 3R)-methyl-phenylalanine (Kazmierski and Hruby, Tetrahedron Lett. (1991)).

Exemplary, illustrative but non-limiting non-natural amino acids include beta-amino acids (beta3 and beta2), homo-amino acids, cyclic amino acids, aromatic amino acids, Pro and Pyr derivatives, 3-substituted Alanine derivatives, Glycine derivatives, ring-substituted Phe and Tyr Derivatives, linear core amino acids or diamino acids. They are available from a variety of suppliers, such as Sigma-Aldrich (USA) for example.

Chemical Modifications

In the present invention any part of a protein according to at least some embodiments of the invention may optionally be chemically modified, i.e. changed by addition of functional groups. For example the side amino acid residues appearing in the native sequence may optionally be modified, although as described below alternatively other parts of the protein may optionally be modified, in addition to or in place of the side amino acid residues. The modification may optionally be performed during synthesis of the molecule if a chemical synthetic process is followed, for example by adding a chemically modified amino acid. However, chemical modification of an amino acid when it is already present in the molecule ("in situ" modification) is also possible.

The amino acid of any of the sequence regions of the molecule can optionally be modified according to any one of the following exemplary types of modification (in the peptide conceptually viewed as "chemically modified"). Non-limiting exemplary types of modification include carboxymethylation, acylation, phosphorylation, glycosylation or fatty acylation. Ether bonds can optionally be used to join the serine or threonine hydroxyl to the hydroxyl of a sugar. Amide bonds can optionally be used to join the glutamate or aspartate carboxyl groups to an amino group on a sugar (Garg and Jeanloz, Advances in Carbohydrate Chemistry and Biochemistry, Vol. 43, Academic Press (1985); Kunz, Ang. Chem. Int. Ed. English 26:294-308 (1987)). Acetal and ketal bonds can also optionally be formed between amino acids and carbohydrates. Fatty acid acyl derivatives can optionally be made, for example, by acylation of a free amino group (e.g., lysine) (Toth et al., Peptides: Chemistry, Structure and Biology, Rivier and Marshal, eds., ESCOM Publ., Leiden, 1078-1079 (1990)).

As used herein the term "chemical modification", when referring to a protein or peptide according to the present invention, refers to a protein or peptide where at least one of its amino acid residues is modified either by natural processes, such as processing or other post-translational modifications, or by chemical modification techniques which are well known in the art. Examples of the numerous known modifications typically include, but are not limited to: acetylation, acylation, amidation, ADP-ribosylation, glycosylation, GPI anchor formation, covalent attachment of a lipid or lipid derivative, methylation, myristylation, pegylation, prenylation, phosphorylation, ubiquitination, or any similar process.

Other types of modifications optionally include the addition of a cycloalkane moiety to a biological molecule, such as a protein, as described in PCT Application No. WO 2006/050262, hereby incorporated by reference as if fully set forth herein. These moieties are designed for use with biomolecules and may optionally be used to impart various properties to proteins.

Furthermore, optionally any point on a protein may be modified. For example, pegylation of a glycosylation moiety on a protein may optionally be performed, as described in PCT Application No. WO 2006/050247, hereby incorporated by reference as if fully set forth herein. One or more polyethylene glycol (PEG) groups may optionally be added to O-linked and/or N-linked glycosylation. The PEG group may optionally be branched or linear. Optionally any type of water-soluble polymer may be attached to a glycosylation site on a protein through a glycosyl linker.

Altered Glycosylation

Proteins according to at least some embodiments of the invention may be modified to have an altered glycosylation pattern (i.e., altered from the original or native glycosylation pattern). As used herein, "altered" means having one or more carbohydrate moieties deleted, and/or having at least one glycosylation site added to the original protein.

Glycosylation of proteins is typically either N-linked or O-linked. N-linked refers to the attachment of the carbohydrate moiety to the side chain of an asparagine residue. The tripeptide sequences, asparagine-X-serine and asparagine-X-threonine, where X is any amino acid except proline, are the recognition sequences for enzymatic attachment of the carbohydrate moiety to the asparagine side chain. Thus, the presence of either of these tripeptide sequences in a polypeptide creates a potential glycosylation site. O-linked glycosylation refers to the attachment of one of the sugars N-acetylgalactosamine, galactose, or xylose to a hydroxyamino acid, most commonly serine or threonine, although 5-hydroxyproline or 5-hydroxylysine may also be used.

Addition of glycosylation sites to proteins according to at least some embodiments of the invention is conveniently accomplished by altering the amino acid sequence of the protein such that it contains one or more of the above-described tripeptide sequences (for N-linked glycosylation sites). The alteration may also be made by the addition of, or substitution by, one or more serine or threonine residues in the sequence of the original protein (for O-linked glycosylation sites). The protein's amino acid sequence may also be altered by introducing changes at the DNA level.

Another means of increasing the number of carbohydrate moieties on proteins is by chemical or enzymatic coupling of glycosides to the amino acid residues of the protein. Depending on the coupling mode used, the sugars may be attached to (a) arginine and histidine, (b) free carboxyl groups, (c) free sulfhydryl groups such as those of cysteine, (d) free hydroxyl groups such as those of serine, threonine, or hydroxyproline, (e) aromatic residues such as those of phenylalanine, tyrosine, or tryptophan, or (f) the amide group of glutamine. These methods are described in WO 87/05330, and in Aplin and Wriston, CRC Crit. Rev. Biochem., 22: 259-306 (1981).

Removal of any carbohydrate moieties present on proteins according to at least some embodiments of the invention may be accomplished chemically or enzymatically. Chemical deglycosylation requires exposure of the protein to trifluoromethanesulfonic acid, or an equivalent compound. This treatment results in the cleavage of most or all sugars except the linking sugar (N-acetylglucosamine or N-acetylgalactosamine), leaving the amino acid sequence intact.

Chemical deglycosylation is described by Hakimuddin et al., Arch. Biochem. Biophys., 259: 52 (1987); and Edge et al., Anal. Biochem., 118: 131 (1981). Enzymatic cleavage of carbohydrate moieties on proteins can be achieved by the use of a variety of endo- and exo-glycosidases as described by Thotakura et al., Meth. Enzymol., 138: 350 (1987).

EXAMPLE 4

Antibodies According to at Least Some Embodiments of the Present Invention

This Example relates to antibodies which specifically bind to and recognize T4, T5 or "skip 10" proteins according to at least some embodiments of the present invention, and uses and compositions thereof.

The antibodies according to at least some embodiments of the invention including those having the particular germline sequences, homologous antibodies, antibodies with conservative modifications, engineered and modified antibodies are characterized by particular functional features or properties of the antibodies. For example, the antibodies bind specifically to human T4, T5 or "skip 10" proteins. Optionally, an antibody according to at least some embodiments of the invention binds to corresponding T4, T5 or "skip 10" proteins with high affinity, for example with a KD of 10-8 M or less or 10-9 M or less or even 10-10 M or less. The Anti-T4, anti-T5 or anti-"skip 10" antibodies according to at least some embodiments of the invention optionally exhibit one or more of the following characteristics:

(i) binds to one of the corresponding human T4, T5 or "skip 10" polypeptides with a KD of 5×10-8 M or less;

(ii) binds to one of the T4, T5 or "skip 10" antigen expressed by cancer cells including for example ovarian cancer, lung cancer, colon cancer, breast cancer, kidney cancer, liver cancer, pancreatic cancer, prostate cancer, melanoma and hematological malignancies such as Multiple Myeloma, lymphoma, Non-Hodgkin's lymphoma, leukemia, T cell leukemia, but does not substantially bind to normal cells. In addition, optionally these antibodies and conjugates thereof will be effective in eliciting selective killing of such cancer cells and for modulating immune responses involved in autoimmunity and cancer.

Optionally, the antibody binds to one of the corresponding human T4, T5 or "skip 10" antigens with a KD of 3×10-8 M or less, or with a KD of 1×10-9 M or less, or with a KD of 0.1×10-9 M or less, or with a KD Of 0.05×10-9 M or less or with a KD of between 1×10-9 and 1×10-11 M.

According to some embodiments, the anti-T5, T4 or "skip 10" antibody circumvents the coagulation-related side effects, associated with known heparanase antagonists, as it doesn't effect the coagulation cascade.

Standard assays to evaluate the binding ability of the antibodies toward T4, T5 or "skip 10" polypeptides are known in the art, including for example, ELISAs, Western blots and RIAs. Suitable assays are described in detail in the Examples. The binding kinetics (e.g., binding affinity) of the antibodies also can be assessed by standard assays known in the art, such as by Biacore analysis.

Upon production of Anti-T4, anti-T5 or anti-"skip 10" antibody sequences from antibodies can bind to T4, T5 or "skip 10", the VH and VL sequences can be "mixed and matched" to create other anti-T4, T5 or "skip 10" binding molecules according to at least some embodiments of the invention. T4, T5 or "skip 10" binding of such "mixed and matched" antibodies can be tested using the binding assays described above. e.g., ELISAs). Optionally, when VH and VL chains are mixed and matched, a VH sequence from a particular VH/VL pairing is replaced with a structurally similar VH sequence. Likewise, optionally a VL sequence from a particular VH/VL pairing is replaced with a structurally similar VL sequence. For example, the VH and VL sequences of homologous antibodies are particularly amenable for mixing and matching.

Antibodies Having Particular Germline Sequences

In certain embodiments, an antibody according to at least some embodiments of the invention comprises a heavy chain variable region from a particular germline heavy chain immunoglobulin gene and/or a light chain variable region from a particular germline light chain immunoglobulin gene.

As used herein, a human antibody comprises heavy or light chain variable regions that is "the product of" or "derived from" a particular germline sequence if the variable regions of the antibody are obtained from a system that uses human germline immunoglobulin genes. Such systems include immunizing a transgenic mouse carrying human immunoglobulin genes with the antigen of interest or screening a human immunoglobulin gene library displayed on phage with the antigen of interest. A human antibody that is "the product of" or "derived from" a human germline immunoglobulin sequence can be identified as such by comparing the amino acid sequence of the human antibody to the amino acid sequences of human germline immunoglobulins and selecting the human germline immunoglobulin sequence that is closest in sequence (i.e., greatest % identity) to the sequence of the human antibody.

A human antibody that is "the product of" or "derived from" a particular human germline immunoglobulin sequence may contain amino acid differences as compared to the germline sequence, due to, for example, naturally-occurring somatic mutations or intentional introduction of site-directed mutation. However, a selected human antibody typically is at least 90% identical in amino acids sequence to an amino acid sequence encoded by a human germline immunoglobulin gene and contains amino acid residues that identify the human antibody as being human when compared to the germline immunoglobulin amino acid sequences of other species (e.g., murine germline sequences). In certain cases, a human antibody may be at least 95, 96, 97, 98 or 99%, or even at least 96%, 97%, 98%, or 99% identical in amino acid sequence to the amino acid sequence encoded by the germline immunoglobulin gene. Typically, a human antibody derived from a particular human germline sequence will display no more than 10 amino acid differences from the amino acid sequence encoded by the human germline immunoglobulin gene. In certain cases, the human antibody may display no more than 5, or even no more than 4, 3, 2, or 1 amino acid difference from the amino acid sequence encoded by the germline immunoglobulin gene.

Homologous Antibodies

In yet another embodiment, an antibody according to at least some embodiments of the invention comprises heavy and light chain variable regions comprising amino acid sequences that are homologous to isolated Anti-T4, T5 or "skip 10" amino acid sequences of preferred Anti-T4, T5 or "skip 10" antibodies, respectively, wherein the antibodies retain the desired functional properties of the parent Anti-T4, T5 or "skip 10" antibodies.

As used herein, the percent homology between two amino acid sequences is equivalent to the percent identity between the two sequences. The percent identity between the two sequences is a function of the number of identical positions shared by the sequences (i.e., % homology=# of identical positions/total # of positions×100), taking into account the number of gaps, and the length of each gap, which need to be introduced for optimal alignment of the two sequences. The comparison of sequences and determination of percent identity between two sequences can be accomplished using a mathematical algorithm, as described in the non-limiting examples below.

The percent identity between two amino acid sequences can be determined using the algorithm of E. Meyers and W. Miller (Comput. Appl. Biosci., 4:11-17 (1988)) which has been incorporated into the ALIGN program (version 2.0), using a PAM120 weight residue table, a gap length penalty of 12 and a gap penalty of 4. In addition, the percent identity between two amino acid sequences can be determined using the Needleman and Wunsch (J. Mol. Biol. 48:444-453 (1970)) algorithm which has been incorporated into the GAP program in the GCG software package (available commercially), using either a Blossum 62 matrix or a PAM250 matrix, and a gap weight of 16, 14, 12, 10, 8, 6, or 4 and a length weight of 1, 2, 3, 4, 5, or 6.

Additionally or alternatively, the protein sequences according to at least some embodiments of the present invention can further be used as a "query sequence" to perform a search against public databases to, for example, identify related sequences. Such searches can be performed using the XBLAST program (version 2.0) of Altschul, et al. (1990) J Mol. Biol. 215:403-10. BLAST protein searches can be performed with the XBLAST program, score=50, wordlength=3 to obtain amino acid sequences homologous to the antibody molecules according to at least some embodiments of the invention. To obtain gapped alignments for comparison purposes, Gapped BLAST can be utilized as described in Altschul et al., (1997) Nucleic Acids Res. 25(17):3389-3402. When utilizing BLAST and Gapped BLAST programs, the default parameters of the respective programs (e.g., XBLAST and NBLAST) can be used.

Antibodies with Conservative Modifications

In certain embodiments, an antibody according to at least some embodiments of the invention comprises a heavy chain variable region comprising CDR1, CDR2 and CDR3 sequences and a light chain variable region comprising CDR1, CDR2 and CDR3 sequences, wherein one or more of these CDR sequences comprise specified amino acid sequences based on preferred Anti-T4, T5 or "skip 10" antibodies isolated and produced using methods herein, or conservative modifications thereof, and wherein the antibodies retain the desired functional properties of the Anti-T4, T5 or "skip 10" antibodies according to at least some embodiments of the invention, respectively.

In various embodiments, the Anti-T4, T5 or "skip 10" antibody can be, for example, human antibodies, humanized antibodies or chimeric antibodies.

As used herein, the term "conservative sequence modifications" is intended to refer to amino acid modifications that do not significantly affect or alter the binding characteristics of the antibody containing the amino acid sequence. Such conservative modifications include amino acid substitutions, additions and deletions. Modifications can be introduced into an antibody according to at least some embodiments of the invention by standard techniques known in the art, such as site-directed mutagenesis and PCR-mediated mutagenesis. Conservative amino acid substitutions are ones in which the amino acid residue is replaced with an amino acid residue having a similar side chain Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine, tryptophan), nonpolar side chains (e.g., alanine, valine, leucine, isoleucine, proline, phenylalanine, methionine), beta-branched side chains (e.g., threonine, valine, isoleucine) and aromatic side chains (e.g., tyrosine, phenylalanine, tryptophan, histidine). Thus, one or more amino acid residues within the CDR regions of an antibody according to at least some embodiments of the invention can be replaced with other amino acid residues from the same side chain family and the altered antibody can be tested for retained function (i.e., the functions set forth in (c) through (j) above) using the functional assays described herein.

Engineered and Modified Antibodies

An antibody according to at least some embodiments of the invention can be prepared using an antibody having one or more of the VH and/or VL sequences derived from an Anti-T4, T5 or "skip 10" antibody starting material to engineer a modified antibody, which modified antibody may have altered properties from the starting antibody. An antibody can be engineered by modifying one or more residues within one or both variable regions (i.e., VH and/or VL), for example within one or more CDR regions and/or within one or more framework regions. Additionally or alternatively, an antibody can be engineered by modifying residues within the constant regions, for example to alter the effector functions of the antibody.

One type of variable region engineering that can be performed is CDR grafting. Antibodies interact with target antigens predominantly through amino acid residues that are located in the six heavy and light chain complementarity determining regions (CDRs). For this reason, the amino acid sequences within CDRs are more diverse between individual antibodies than sequences outside of CDRs. Because CDR sequences are responsible for most antibody-antigen interactions, it is possible to express recombinant antibodies that mimic the properties of specific naturally occurring antibodies by constructing expression vectors that include CDR sequences from the specific naturally occurring antibody grafted onto framework sequences from a different antibody with different properties (see, e.g., Riechmann, L. et al. (1998) Nature 332:323-327; Jones, P. et al. (1986) Nature 321:522-525; Queen, C. et al. (1989) Proc. Natl. Acad. See. U.S.A. 86:10029-10033; U.S. Pat. No. 5,225,539 to Winter, and U.S. Pat. Nos. 5,530,101; 5,585,089; 5,693,762 and 6,180,370 to Queen et al.)

Suitable framework sequences can be obtained from public DNA databases or published references that include germline antibody gene sequences. For example, germline DNA sequences for human heavy and light chain variable region genes can be found in the "VBase" human germline sequence database (available on the Internet), as well as in Kabat, E. A., et al. (1991) Sequences of Proteins of Immunological Interest, Fifth Edition, U.S. Department of Health and Human Services, NIH Publication No. 91-3242; Tomlinson, I. M., et al. (1992) "The Repertoire of Human Germline VH Sequences Reveals about Fifty Groups of VH Segments with Different Hypervariable Loops" J. Mol. Biol. 227:776-798; and Cox, J. P. L. et al. (1994) "A Directory of Human Germ-line VH Segments Reveals a Strong Bias in their Usage" Eur. J Immunol. 24:827-836; the contents of each of which are expressly incorporated herein by reference.

Another type of variable region modification is to mutate amino acid residues within the VH and/or VL CDR 1, CDR2 and/or CDR3 regions to thereby improve one or more binding properties (e.g., affinity) of the antibody of interest. Site-directed mutagenesis or PCR-mediated mutagenesis can be performed to introduce the mutations and the effect on antibody binding, or other functional property of interest, can be evaluated in appropriate in vitro or in vivo assays. Optionally conservative modifications (as discussed above) are introduced. The mutations may be amino acid substitutions, additions or deletions, but are preferably substitutions. Moreover, typically no more than one, two, three, four or five residues within a CDR region are altered.

Engineered antibodies according to at least some embodiments of the invention include those in which modifications have been made to framework residues within VH and/or VL, e.g. to improve the properties of the antibody. Typically such framework modifications are made to decrease the immunogenicity of the antibody. For example, one approach is to "backmutate" one or more framework residues to the corresponding germline sequence. More specifically, an antibody that has undergone somatic mutation may contain framework residues that differ from the germline sequence from which the antibody is derived. Such residues can be identified by comparing the antibody framework sequences to the germline sequences from which the antibody is derived.

In addition or alternative to modifications made within the framework or CDR regions, antibodies according to at least some embodiments of the invention may be engineered to include modifications within the Fc region, typically to alter one or more functional properties of the antibody, such as serum half-life, complement fixation, Fc receptor binding, and/or antigen-dependent cellular cytotoxicity. Furthermore, an antibody according to at least some embodiments of the invention may be chemically modified (e.g., one or more chemical moieties can be attached to the antibody) or be modified to alter its glycosylation, again to alter one or more functional properties of the antibody. Such embodiments are described further below. The numbering of residues in the Fc region is that of the EU index of Kabat.

In one embodiment, the hinge region of CH1 is modified such that the number of cysteine residues in the hinge region is altered, e.g., increased or decreased. This approach is described further in U.S. Pat. No. 5,677,425 by Bodmer et al. The number of cysteine residues in the hinge region of CH1 is altered to, for example, facilitate assembly of the light and heavy chains or to increase or decrease the stability of the antibody.

In another embodiment, the Fc hinge region of an antibody is mutated to decrease the biological half life of the antibody. More specifically, one or more amino acid mutations are introduced into the CH2-CH3 domain interface region of the Fc-hinge fragment such that the antibody has impaired Staphylococcyl protein A (SpA) binding relative to native Fc-hinge domain SpA binding. This approach is described in further detail in U.S. Pat. No. 6,165,745 by Ward et al.

In another embodiment, the antibody is modified to increase its biological half life. Various approaches are possible. For example, one or more of the following mutations can be introduced: T252L, T254S, T256F, as described in U.S. Pat. No. 6,277,375 to Ward. Alternatively, to increase the biological half life, the antibody can be altered within the CH1 or CL region to contain a salvage receptor binding epitope taken from two loops of a CH2 domain of an Fc region of an IgG, as described in U.S. Pat. Nos. 5,869,046 and 6,121,022 by Presta et al.

In yet other embodiments, the Fc region is altered by replacing at least one amino acid residue with a different amino acid residue to alter the effector functions of the antibody. For example, one or more amino acids selected from amino acid residues 234, 235, 236, 237, 297, 318, 320 and 322 can be replaced with a different amino acid residue such that the antibody has an altered affinity for an effector ligand but retains the antigen-binding ability of the parent antibody. The effector ligand to which affinity is altered can be, for example, an Fc receptor or the C1 component of complement. This approach is described in further detail in U.S. Pat. Nos. 5,624,821 and 5,648,260, both by Winter et al.

In another example, one or more amino acids selected from amino acid residues 329, 331 and 322 can be replaced with a different amino acid residue such that the antibody has altered C1q binding and/or reduced or abolished complement dependent cytotoxicity (CDC). This approach is described in further detail in U.S. Pat. No. 6,194,551 by Idusogie et al.

In another example, one or more amino acid residues within amino acid positions 231 and 239 are altered to thereby alter the ability of the antibody to fix complement. This approach is described further in PCT Publication WO 94/29351 by Bodmer et al.

In yet another example, the Fc region is modified to increase the ability of the antibody to mediate antibody dependent cellular cytotoxicity (ADCC) and/or to increase the affinity of the antibody for an Fcγ receptor by modifying one or more amino acids at the following positions: 238, 239, 248, 249, 252, 254, 255, 256, 258, 265, 267, 268, 269, 270, 272, 276, 278, 280, 283, 285, 286, 289, 290, 292, 293, 294, 295, 296, 298, 301, 303, 305, 307, 309, 312, 315, 320, 322, 324, 326, 327, 329, 330, 331, 333, 334, 335, 337, 338, 340, 360, 373, 376, 378, 382, 388, 389, 398, 414, 416, 419, 430, 434, 435, 437, 438 or 439. This approach is described further in PCT Publication WO 00/42072 by Presta. Moreover, the binding sites on human IgG1 for Fc grammar, Fc gamma RII, Fc gammaRIII and FcRn have been mapped and variants with improved binding have been described (see Shields, R. L. et al. (2001) J. Biol. Chem. 276:6591-6604). Specific mutations at positions 256, 290, 298, 333, 334 and 339 are shown to improve binding to FcγRIII. Additionally, the following combination mutants are shown to improve Fcgamma.RIII binding: T256A/S298A, S298A/E333A, S298A/K224A and S298A/E333A/K334A.

In still another embodiment, the glycosylation of an antibody is modified. For example, an aglycoslated antibody can be made (i.e., the antibody lacks glycosylation). Glycosylation can be altered to, for example, increase the affinity of the antibody for antigen. Such carbohydrate modifications can be accomplished by, for example, altering one or more sites of glycosylation within the antibody sequence. For example, one or more amino acid substitutions can be made that result in elimination of one or more variable region framework glycosylation sites to thereby eliminate glycosylation at that site. Such aglycosylation may increase the affinity of the antibody for antigen. Such an approach is described in further detail in U.S. Pat. Nos. 5,714,350 and 6,350,861 by Co et al.

Additionally or alternatively, an antibody can be made that has an altered type of glycosylation, such as a hypofucosylated antibody having reduced amounts of fucosyl residues or an antibody having increased bisecting GlcNac structures. Such altered glycosylation patterns have been demonstrated to increase the ADCC ability of antibodies. Such carbohydrate modifications can be accomplished by, for example, expressing the antibody in a host cell with altered glycosylation machinery. Cells with altered glycosylation machinery have been described in the art and can be used as host cells in which to express recombinant antibodies according to at least some embodiments of the invention to thereby produce an antibody with altered glycosylation. For example, the cell lines Ms704, Ms705, and Ms709 lack the fucosyltransferase gene, FUT8 (alpha (1,6) fucosyltransferase), such that antibodies expressed in the Ms704, Ms705, and Ms709 cell lines lack fucose on their carbohydrates. The Ms704, Ms705, and Ms709 FUT8.−/− cell lines are created by the targeted disruption of the FUT8 gene in CHO/DG44 cells using two replacement vectors (see U.S. Patent Publication No. 20040110704 by Yamane et al. and Yamane-Ohnuki et al. (2004) Biotechnol Bioeng 87:614-22). As another example, EP 1,176,195 by Hanai et al. describes a cell line with a functionally disrupted FUT8 gene, which encodes a fucosyl transferase, such that antibodies expressed in such a cell line exhibit hypofucosylation by reducing or eliminating the alpha 1,6 bond-related enzyme. Hanai et al. also describe cell lines which have a low enzyme activity for adding fucose to the N-acetylglucosamine that binds to the Fc region of the antibody or does not have the enzyme activity, for example the rat myeloma cell line YB2/0 (ATCC CRL 1662). PCT Publication WO 03/035835 by Presta describes a variant CHO cell line, Lec13 cells, with reduced ability to attach fucose to Asn (297)-linked carbohydrates, also resulting in hypofucosylation of antibodies expressed in that host cell (see also Shields, R. L. et al. (2002) J. Biol. Chem. 277:26733-26740). PCT Publication WO 99/54342 by Umana et al. describes cell lines engineered to express glycoprotein-modifying glycosyl transferases (e.g., beta(1,4)-N-acetylglucosaminyltransferase III (GnTIII)) such that antibodies expressed in the engineered cell lines exhibit increased bisecting GlcNac structures which results in increased ADCC activity of the antibodies (see also Umana et al. (1999) Nat. Biotech. 17:176-180). Alternatively, the fucose residues of the antibody may be cleaved off using a fucosidase enzyme. For example, the fucosidase alpha-L-fucosidase removes fucosyl residues from antibodies (Tarentino, A. L. et al. (1975) Biochem. 14:5516-23).

Another modification of the antibodies herein that is contemplated by the invention is pegylation. An antibody can be pegylated to, for example, increase the biological (e.g., serum) half life of the antibody. To pegylate an antibody, the antibody, or fragment thereof, typically is reacted with polyethylene glycol (PEG), such as a reactive ester or aldehyde derivative of PEG, under conditions in which one or more PEG groups become attached to the antibody or antibody fragment. Optionally, the pegylation is carried out via an acylation reaction or an alkylation reaction with a reactive PEG molecule (or an analogous reactive water-soluble polymer). As used herein, the term "polyethylene glycol" is intended to encompass any of the forms of PEG that have been used to derivatize other proteins, such as mono (C1-C10) alkoxy- or aryloxy-polyethylene glycol or polyethylene glycol-maleimide. In certain embodiments, the antibody to be pegylated is an aglycosylated antibody. Methods for pegylating proteins are known in the art and can be applied to the antibodies according to at least some embodiments of the invention. See for example, EP 0 154 316 by Nishimura et al. and EP 0 401 384 by Ishikawa et al.

Methods of Engineering Antibodies

As discussed above, the Anti-T4, T5 or "skip 10" antibodies having VH and VK sequences disclosed herein can be used to create new Anti-T4, T5 or "skip 10" antibodies, respectively, by modifying the VH and/or VL sequences, or the constant regions attached thereto. Thus, according to at least some embodiments of the invention, the structural features of an Anti-T4, T5 or "skip 10" antibody according to at least some embodiments of the invention, are used to create structurally related Anti-T4, T5 or "skip 10" antibodies that retain at least one functional property of the antibodies according to at least some embodiments of the invention, such as binding to human T4, T5 or "skip 10", respectively. For example, one or more CDR regions of one T4, T5 or "skip 10" antibody or mutations thereof, can be combined recombinantly with known framework regions and/or other CDRs to create additional, recombinantly-engineered, Anti-T4, T5 or "skip 10" antibodies according to at least some embodiments of the invention, as discussed above. Other types of modifications include those described in the previous section. The starting material for the engineering method is one or more of the VH and/or VK sequences provided herein, or one or more CDR regions thereof. To create the engineered antibody, it is not necessary to actually prepare (i.e., express as a protein) an antibody having one or more of the VH and/or VK sequences provided herein, or one or more CDR regions thereof. Rather, the information contained in the sequences is used as the starting material to create a "second generation" sequences derived from the original sequences and then the "second generation" sequences is prepared and expressed as a protein.

Standard molecular biology techniques can be used to prepare and express altered antibody sequence.

Optionally, the antibody encoded by the altered antibody sequences is one that retains one, some or all of the functional properties of the Anti-T4, T5 or "skip 10" antibodies, respectively, produced by methods and with sequences provided herein, which functional properties include binding to T4, T5 or "skip 10" antigen with a specific KD level or less and/or selectively binding to desired target cells such as ovarian cancer, lung cancer, breast cancer, colon cancer, kidney cancer, liver cancer, pancreatic cancer, prostate cancer, melanoma and hematological malignancies such as Multiple Myeloma, lymphoma, Non-Hodgkin's lymphoma, leukemia, T cell leukemia, that express T4, T5 or "skip 10" antigen.

The functional properties of the altered antibodies can be assessed using standard assays available in the art and/or described herein.

In certain embodiments of the methods of engineering antibodies according to at least some embodiments of the invention, mutations can be introduced randomly or selectively along all or part of an Anti-T4, T5 or "skip 10" antibody coding sequence and the resulting modified Anti-T4, T5 or "skip 10" antibodies can be screened for binding activity and/or other desired functional properties.

Mutational methods have been described in the art. For example, PCT Publication WO 02/092780 by Short describes methods for creating and screening antibody mutations using saturation mutagenesis, synthetic ligation assembly, or a combination thereof. Alternatively, PCT Publication WO 03/074679 by Lazar et al. describes methods of using computational screening methods to optimize physiochemical properties of antibodies.

Nucleic Acid Molecules Encoding Antibodies

According to at least some embodiments of the invention pertains to nucleic acid molecules that encode the antibodies according to at least some embodiments of the invention. The nucleic acids may be present in whole cells, in a cell lysate, or in a partially purified or substantially pure form. A nucleic acid is "isolated" or "rendered substantially pure" when purified away from other cellular components or other contaminants, e.g., other cellular nucleic acids or proteins, by standard techniques, including alkaline/SDS treatment, CsCl banding, column chromatography, agarose gel electrophoresis and others well known in the art. See, F. Ausubel, et al., ed. (1987) Current Protocols in Molecular Biology, Greene Publishing and Wiley Interscience, New York. A nucleic acid according to at least some embodiments of the invention can be, for example, DNA or RNA and may or may not contain intronic sequences. In a preferred embodiment, the nucleic acid is a cDNA molecule.

Nucleic acids according to at least some embodiments of the invention can be obtained using standard molecular biology techniques. For antibodies expressed by hybridomas (e.g., hybridomas prepared from transgenic mice carrying human immunoglobulin genes as described further below), cDNAs encoding the light and heavy chains of the antibody made by the hybridoma can be obtained by standard PCR amplification or cDNA cloning techniques. For antibodies obtained from an immunoglobulin gene library (e.g., using phage display techniques), nucleic acid encoding the antibody can be recovered from the library.

Once DNA fragments encoding VH and VL segments are obtained, these DNA fragments can be further manipulated by standard recombinant DNA techniques, for example to convert the variable region genes to full-length antibody chain genes, to Fab fragment genes or to a scFv gene. In these manipulations, a VL- or VH-encoding DNA fragment is operatively linked to another DNA fragment encoding another protein, such as an antibody constant region or a flexible linker.

The term "operatively linked", as used in this context, is intended to mean that the two DNA fragments are joined such that the amino acid sequences encoded by the two DNA fragments remain in-frame.

The isolated DNA encoding the VH region can be converted to a full-length heavy chain gene by operatively linking the VH-encoding DNA to another DNA molecule encoding heavy chain constant regions (CH1, CH2 and CH3). The sequences of human heavy chain constant region genes are known in the art (see e.g., Kabat, E. A., el al. (1991) Sequences of Proteins of Immunological Interest, Fifth Edition, U.S. Department of Health and Human Services, NIH Publication No. 91-3242) and DNA fragments encompassing these regions can be obtained by standard PCR amplification. The heavy chain constant region can be an IgG1, IgG2, IgG3, IgG4, IgA, IgE, IgM or IgD constant region. For a Fab fragment heavy chain gene, the VH-encoding DNA can be operatively linked to another DNA molecule encoding only the heavy chain CH1 constant region.

The isolated DNA encoding the VL region can be converted to a full-length light chain gene (as well as a Fab light chain gene) by operatively linking the VL-encoding DNA to another DNA molecule encoding the light chain constant region, CL. The sequences of human light chain constant region genes are known in the art (see e.g., Kabat, E. A., et al. (1991) Sequences of Proteins of Immunological Interest, Fifth Edition, U.S. Department of Health and Human Services, NIH Publication No. 91-3242) and DNA fragments encompassing these regions can be obtained by standard PCR amplification. The light chain constant region can be a kappa or lambda constant region.

To create a scFv gene, the VH- and VL-encoding DNA fragments are operatively linked to another fragment encoding a flexible linker, e.g., encoding the amino acid sequence (Gly4-Ser)3, such that the VH and VL sequences can be expressed as a contiguous single-chain protein, with the VL and VH regions joined by the flexible linker (see e.g., Bird et al. (1988) Science 242:423-426; Huston et al. (1988) Proc. Natl. Acad. Sci. USA 85:5879-5883; McCafferty et al., (1990) Nature 348:552-554).

Production of Anti-T4, T5 or "Skip 10" Monoclonal Antibodies

Monoclonal antibodies (mAbs) according to at least some embodiments of the present invention can be produced by a variety of techniques, including conventional monoclonal antibody methodology e.g., the standard somatic cell hybridization technique of Kohler and Milstein (1975) Nature 256:495. Although somatic cell hybridization procedures are preferred, in principle, other techniques for producing monoclonal antibody can be employed e.g., viral or oncogenic transformation of B lymphocytes.

A preferred animal system for preparing hybridomas is the murine system. Hybridoma production in the mouse is a very well-established procedure Immunization protocols and techniques for isolation of immunized splenocytes for fusion are known in the art. Fusion partners (e.g., murine myeloma cells) and fusion procedures are also known.

Chimeric or humanized antibodies according to at least some embodiments of the present invention can be prepared based on the sequence of a murine monoclonal antibody prepared as described above. DNA encoding the heavy and light chain immunoglobulins can be obtained from the murine hybridoma of interest and engineered to contain non-murine (e.g., human) immunoglobulin sequences using standard molecular biology techniques. For example, to create a chimeric antibody, the murine variable regions can be linked to human constant regions using methods known in the art (see e.g., U.S. Pat. No. 4,816,567 to Cabilly et al.). To create a humanized antibody, the murine CDR regions can be inserted into a human framework using methods known in the art (see e.g., U.S. Pat. No. 5,225,539 to Winter, and U.S. Pat. Nos. 5,530,101; 5,585,089; 5,693,762 and 6,180,370 to Queen et al.).

In a preferred embodiment, the antibodies according to at least some embodiments of the invention are human monoclonal antibodies. Such human monoclonal antibodies directed against T4, T5 or "skip 10" can be generated using transgenic or transchromosomic mice carrying parts of the human immune system rather than the mouse system. These transgenic and transchromosomic mice include mice referred to herein as the HuMAb Mouse® and KM Mouse® respectively, and are collectively referred to herein as "human Ig mice." The HuMAb Mouse™ (Medarex. Inc.) contains human immunoglobulin gene miniloci that encode unrearranged human heavy (.mu. and .gamma.) and .kappa. light chain immunoglobulin sequences, together with targeted mutations that inactivate the endogenous.mu. and .kappa. chain loci (see e.g., Lonberg, et al. (1994) Nature 368(6474): 856-859). Accordingly, the mice exhibit reduced expression of mouse IgM or .kappa., and in response to immunization, the introduced human heavy and light chain transgenes undergo class switching and somatic mutation to generate high affinity human IgGkappa. monoclonal (Lonberg, N. et al. (1994), supra; reviewed in Lonberg, N. (1994) Handbook of Experimental Pharmacology 113:49-101; Lonberg, N. and Huszar, D. (1995) Intern. Rev. Immunol. 13: 65-93, and Harding, F. and Lonberg, N. (1995) Ann. N.Y. Acad. Sci. 764:536-546). The preparation and use of the HuMab Mouse®, and the genomic modifications carried by such mice, is further described in Taylor, L. et al. (1992) Nucleic Acids Research 20:6287-6295; Chen, J. et al. (1993) International Immunology 5:647-656; Tuaillon et al. (1993) Proc. Natl. Acad. Sci. USA 90:3720-3724; Choi et al. (1993) Nature Genetics 4:117-123; Chen, J. et al. (1993) EMBO J. 12: 821-830; Tuaillon et al. (1994) J. Immunol. 152:2912-2920; Taylor, L. et al. (1994) International Immunology 6:579-591; and Fishwild, D. et al. (1996) Nature Biotechnology 14: 845-851, the contents of all of which are hereby specifically incorporated by reference in their entirety. See further, U.S. Pat. Nos. 5,545,806; 5,569,825; 5,625,126; 5,633,425; 5,789,650; 5,877,397; 5,661,016; 5,814,318; 5,874,299; and 5,770,429; all to Lonberg and Kay; U.S. Pat. No. 5,545,807 to Surani et al.; PCT Publication Nos. WO 92/03918, WO 93/12227, WO 94/25585, WO 97/13852, WO 98/24884 and WO 99/45962, all to Lonberg and Kay; and PCT Publication No. WO 01/14424 to Korman et al.

In another embodiment, human antibodies according to at least some embodiments of the invention can be raised using a mouse that carries human immunoglobulin sequences on transgenes and transchromosomes, such as a mouse that carries a human heavy chain transgene and a human light chain transchromosome. Such mice, referred to herein as "KM Mice™", are described in detail in PCT Publication WO 02/43478 to Ishida et al.

Still further, alternative transgenic animal systems expressing human immunoglobulin genes are available in the art and can be used to raise anti-T4, T5 or "skip 10" antibodies according to at least some embodiments of the invention. For example, an alternative transgenic system referred to as the Xenomouse (Abgenix, Inc.) can be used; such mice are described in, for example, U.S. Pat. Nos. 5,939,598; 6,075,181; 6,114,598; 6, 150,584 and 6,162,963 to Kucherlapati et al.

Moreover, alternative transchromosomic animal systems expressing human immunoglobulin genes are available in the art and can be used to raise Anti-T4, T5 or "skip 10" antibodies according to at least some embodiments of the invention. For example, mice carrying both a human heavy chain transchromosome and a human light chain transchromosome, referred to as "TC mice" can be used; such mice are described in Tomizuka et al. (2000) Proc. Natl. Acad Sci. USA 97:722-727. Furthermore, cows carrying human heavy and light chain transchromosomes have been described in the art (Kuroiwa et al. (2002) Nature Biotechnology 20:889-894) and can be used to raise Anti-T4, T5 or "skip 10" antibodies according to at least some embodiments of the invention.

Human monoclonal antibodies according to at least some embodiments of the invention can also be prepared using phage display methods for screening libraries of human immunoglobulin genes. Such phage display methods for isolating human antibodies are established in the art. See for example: U.S. Pat. Nos. 5,223,409; 5,403,484; and 5,571,698 to Ladner et al.; U.S. Pat. Nos. 5,427,908 and 5,580,717 to Dower et al.; U.S. Pat. Nos. 5,969,108 and 6,172,197 to McCafferty et al.; and U.S. Pat. Nos. 5,885,793; 6,521,404; 6,544,731; 6,555,313; 6,582,915 and 6,593,081 to Griffiths et al.

Human monoclonal antibodies according to at least some embodiments of the invention can also be prepared using SCID mice into which human immune cells have been reconstituted such that a human antibody response can be generated upon immunization. Such mice are described in, for example, U.S. Pat. Nos. 5,476,996 and 5,698,767 to Wilson et al.

Immunization of Human Ig Mice

When human Ig mice are used to raise human antibodies according to at least some embodiments of the invention, such mice can be immunized with a purified or enriched preparation of T4, T5 or "skip 10" antigen and/or recombinant T4, T5 or "skip 10", or an T4, T5 or "skip 10" fusion protein, as described by Lonberg, N. et al. (1994) Nature 368(6474): 856-859; Fishwild, D. et al. (1996) Nature Biotechnology 14: 845-851; and PCT Publication WO 98/24884 and WO 01/14424. Preferably, the mice will be 6-16 weeks of age upon the first infusion. For example, a purified or recombinant preparation (5-50 .mu.g) of T4, T5 or "skip 10" antigen can be used to immunize the human Ig mice intraperitoneally.

Prior experience with various antigens by others has shown that the transgenic mice respond when initially immunized intraperitoneally (IP) with antigen in complete Freund's adjuvant, followed by every other week IP immunizations (up to a total of 6) with antigen in incomplete Freund's adjuvant. However, adjuvants other than Freund's are also found to be effective. In addition, whole cells in the absence of adjuvant are found to be highly immunogenic. The immune response can be monitored over the course of the immunization protocol with plasma samples being obtained by retroorbital bleeds. The plasma can be screened by ELISA (as described below), and mice with sufficient titers of anti-T4, T5 or "skip 10" human immunoglobulin can be used for fusions. Mice can be boosted intravenously with antigen 3 days before sacrifice and removal of the spleen. It is expected that 2-3 fusions for each immunization may need to be performed. Between 6 and 24 mice are typically immunized for each antigen. Usually both HCo7 and HCo12 strains are used. In addition, both HCo7 and HCo12 transgene can be bred together into a single mouse having two different human heavy chain transgenes (HCo7/HCo12). Alternatively or additionally, the KM Mouse® strain can be used.

Generation of Hybridomas Producing Human Monoclonal Antibodies

To generate hybridomas producing human monoclonal antibodies according to at least some embodiments of the invention, splenocytes and/or lymph node cells from immunized mice can be isolated and fused to an appropriate immortalized cell line, such as a mouse myeloma cell line. The resulting hybridomas can be screened for the production of antigen-specific antibodies. For example, single cell suspensions of splenic lymphocytes from immunized mice can be fused to one-sixth the number of P3X63-Ag8.653 non-secreting mouse myeloma cells (ATCC, CRL 1580) with 50% PEG. Cells are plated at approximately $2 \times 10^{-5}$ in flat bottom microtiter plate, followed by a two week incubation in selective medium containing 20% fetal Clone Serum, 18% "653" conditioned media, 5% origen (IGEN), 4 mM L-glutamine, 1 mM sodium pyruvate, 5 mM HEPES, 0.055 mM 2-mercaptoethanol, 50 units/ml penicillin, 50 mg/ml streptomycin, 50 mg/ml gentamycin and 1×HAT (Sigma; the HAT is added 24 hours after the fusion). After approximately two weeks, cells can be cultured in medium in which the HAT is replaced with HT. Individual wells can then be screened by ELISA for human monoclonal IgM and IgG antibodies. Once extensive hybridoma growth occurs, medium can be observed usually after 10-14 days. The antibody secreting hybridomas can be replated, screened again, and if still positive for human IgG, the monoclonal antibodies can be subcloned at least twice by limiting dilution. The stable subclones can then be cultured in vitro to generate small amounts of antibody in tissue culture medium for characterization.

To purify human monoclonal antibodies, selected hybridomas can be grown in two-liter spinner-flasks for monoclonal antibody purification. Supernatants can be filtered and concentrated before affinity chromatography with protein A-Sepharose (Pharmacia, Piscataway, N.J.). Eluted IgG can be checked by gel electrophoresis and high performance liquid chromatography to ensure purity. The buffer solution can be exchanged into PBS, and the concentration can be determined by OD280 using 1.43 extinction coefficient. The monoclonal antibodies can be aliquoted and stored at −80 degrees C.

Generation of Transfectomas Producing Monoclonal Antibodies

Antibodies according to at least some embodiments of the invention also can be produced in a host cell transfectoma using, for example, a combination of recombinant DNA techniques and gene transfection methods as is well known in the art (e.g., Morrison, S. (1985) Science 229:1202).

For example, to express the antibodies, or antibody fragments thereof, DNAs encoding partial or full-length light and heavy chains, can be obtained by standard molecular biology techniques (e.g., PCR amplification or cDNA cloning using a hybridoma that expresses the antibody of interest) and the DNAs can be inserted into expression vectors such that the genes are operatively linked to transcriptional and translational control sequences. In this context, the term "operatively linked" is intended to mean that an antibody gene is ligated into a vector such that transcriptional and translational control sequences within the vector serve their intended function of regulating the transcription and translation of the antibody gene. The expression vector and expression control sequences are chosen to be compatible with the expression host cell used. The antibody light chain gene and the antibody heavy chain gene can be inserted into separate vector or, more typically, both genes are inserted into the same expression vector. The antibody genes are inserted into the expression vector by standard methods (e.g., ligation of complementary restriction sites on the antibody gene fragment and vector, or blunt end ligation if no restriction sites are present). The light and heavy chain variable regions of the antibodies described herein can be used to create full-length antibody genes of any antibody isotype by inserting them into expression vectors already encoding heavy chain constant and light chain constant regions of the desired isotype such that the VH segment is operatively linked to the CH segments within the vector and the VK segment is operatively linked to the CL segment within the vector. Additionally or alternatively, the recombinant expression vector can encode a signal peptide that facilitates secretion of the antibody chain from a host cell. The antibody chain gene can be cloned into the vector such that the signal peptide is linked in-frame to the amino terminus of the antibody chain gene. The signal peptide can be an immunoglobulin signal peptide or a heterologous signal peptide (i.e., a signal peptide from a non-immunoglobulin protein).

In addition to the antibody chain genes, the recombinant expression vectors according to at least some embodiments of the invention carry regulatory sequences that control the expression of the antibody chain genes in a host cell. The term "regulatory sequence" is intended to include promoters, enhancers and other expression control elements (e.g., polyadenylation signals) that control the transcription or translation of the antibody chain genes. Such regulatory sequences are described, for example, in Goeddel (Gene Expression Technology. Methods in Enzymology 185, Academic Press, San Diego, Calif. (1990)). It will be appreciated by those skilled in the art that the design of the expression vector, including the selection of regulatory sequences, may depend on such factors as the choice of the host cell to be transformed, the level of expression of protein desired, etc. Preferred regulatory sequences for mammalian host cell expression include viral elements that direct high levels of protein expression in mammalian cells, such as promoters and/or enhancers derived from cytomegalovirus (CMV), Simian Virus 40 (SV40), adenovirus, (e.g., the adenovirus major late promoter (AdMLP) and polyoma. Alternatively, nonviral regulatory sequences may be used, such as the ubiquitin promoter or .beta.-globin promoter. Still further, regulatory elements composed of sequences from different sources, such as the SR alpha. promoter system, which contains sequences from the SV40 early promoter and the long terminal repeat of human T cell leukemia virus type 1 (Takebe, Y. et al. (1988) Mol. Cell. Biol. 8:466-472).

In addition to the antibody chain genes and regulatory sequences, the recombinant expression vectors according to at least some embodiments of the invention may carry additional sequences, such as sequences that regulate replication of the vector in host cells (e.g., origins of replication) and selectable marker genes. The selectable marker gene facilitates selection of host cells into which the vector has been introduced (see, e.g., U.S. Pat. Nos. 4,399,216, 4,634,665 and 5,179,017, all by Axel et al.). For example, typically the selectable marker gene confers resistance to drugs, such as G418, hygromycin or methotrexate, on a host cell into which the vector has been introduced. Preferred selectable marker genes include the dihydrofolate reductase (DHFR) gene (for use in dhfr− host cells with methotrexate selection/amplification) and the neo gene (for G418 selection).

For expression of the light and heavy chains, the expression vectors encoding the heavy and light chains is transfected into a host cell by standard techniques. The various forms of the term "transfection" are intended to encompass a wide variety of techniques commonly used for the introduction of exogenous DNA into a prokaryotic or eukaryotic host cell, e.g., electroporation, calcium-phosphate precipitation, DEAE-dextran transfection and the like. Although it is theoretically possible to express the antibodies according to at least some embodiments of the invention in either prokaryotic or eukaryotic host cells, expression of antibodies in eukaryotic cells, and most preferably mammalian host cells, is the most preferred because such eukaryotic cells, and in particular mammalian cells, are more likely than prokaryotic cells to assemble and secrete a properly folded and immunologically active antibody. Prokaryotic expression of antibody genes has been reported to be ineffective for production of high yields of active antibody (Boss, M. A. and Wood, C. R. (1985) Immunology Today 6:12-13).

Preferred mammalian host cells for expressing the recombinant antibodies according to at least some embodiments of the invention include Chinese Hamster Ovary (CHO cells) (including dhfr− CHO cells, described in Urlaub and Chasin, (1980) Proc. Natl. Acad. Sci. USA 77:4216-4220, used with a DHFR selectable marker, e.g., as described in R. J. Kaufman and P. A. Sharp (1982) Mol. Biol. 159:601-621), NSO myeloma cells, COS cells and SP2 cells. In particular, for use with NSO myeloma cells, another preferred expression system is the GS gene expression system disclosed in WO 87/04462, WO 89/01036 and EP 338,841. When recombinant expression vectors encoding antibody genes are introduced into mammalian host cells, the antibodies are produced by culturing the host cells for a period of time sufficient to allow for expression of the antibody in the host cells or, preferably, secretion of the antibody into the culture medium in which the host cells are grown. Antibodies can be recovered from the culture medium using standard protein purification methods.

Characterization of Antibody Binding to Antigen

Antibodies according to at least some embodiments of the invention can be tested for binding to T4, T5 or "skip 10" by, for example, standard ELISA. Briefly, microtiter plates are coated with purified T4, T5 or "skip 10" at 0.25 .mu.g/ml in PBS, and then blocked with 5% bovine serum albumin in PBS. Dilutions of antibody (e.g., dilutions of plasma from T4, T5 or "skip 10"-immunized mice) are added to each well and incubated for 1-2 hours at 37 degrees C. The plates are washed with PBS/Tween and then incubated with secondary reagent (e.g., for human antibodies, a goat-anti-human IgG Fc-specific polyclonal reagent) conjugated to alkaline phosphatase for 1 hour at 37 degrees C. After washing, the plates are developed with pNPP substrate (1 mg/ml), and analyzed at OD of 405-650. Preferably, mice which develop the highest titers will be used for fusions.

An ELISA assay as described above can also be used to screen for hybridomas that show positive reactivity with T4, T5 or "skip 10" immunogen. Hybridomas that bind with high avidity to T4, T5 or "skip 10" are subcloned and further characterized. One clone from each hybridoma, which retains the reactivity of the parent cells (by ELISA), can be chosen for making a 5-10 vial cell bank stored at −140 degrees C., and for antibody purification.

To purify anti-T4, T5 or "skip 10" antibodies, selected hybridomas can be grown in two-liter spinner-flasks for monoclonal antibody purification. Supernatants can be filtered and concentrated before affinity chromatography with protein A-sepharose (Pharmacia, Piscataway, N.J.). Eluted IgG can be checked by gel electrophoresis and high performance liquid chromatography to ensure purity. The buffer solution can be exchanged into PBS, and the concentration can be determined by OD280 using 1.43 extinction coefficient. The monoclonal antibodies can be aliquoted and stored at −80 degrees C.

To determine if the selected anti-T4, T5 or "skip 10" monoclonal antibodies bind to unique epitopes, each antibody can be biotinylated using commercially available reagents (Pierce, Rockford, Ill.). Competition studies using unlabeled monoclonal antibodies and biotinylated monoclonal antibodies can be performed using T4, T5 or "skip 10" coated-ELISA plates as described above. Biotinylated mAb binding can be detected with a strep-avidin-alkaline phosphatase probe.

To determine the isotype of purified antibodies, isotype ELISAs can be performed using reagents specific for antibodies of a particular isotype. For example, to determine the isotype of a human monoclonal antibody, wells of microtiter plates can be coated with 1 .mu.g/ml of anti-human immunoglobulin overnight at 4 degrees C. After blocking with 1% BSA, the plates are reacted with 1 mug/ml or less of test monoclonal antibodies or purified isotype controls, at ambient temperature for one to two hours. The wells can then be reacted with either human IgG1 or human IgM-specific alkaline phosphatase-conjugated probes. Plates are developed and analyzed as described above.

Anti-T4, T5 or "skip 10" human IgGs can be further tested for reactivity with T4, T5 or "skip 10" antigen, respectively, by Western blotting. Briefly, T4, T5 or "skip 10" antigen can be prepared and subjected to sodium dodecyl sulfate polyacrylamide gel electrophoresis. After electrophoresis, the separated antigens are transferred to nitrocellulose membranes, blocked with 10% fetal calf serum, and probed with the monoclonal antibodies to be tested. Human IgG binding can be detected using anti-human IgG alkaline phosphatase and developed with BCIP/NBT substrate tablets (Sigma Chem. Co., St. Louis, Mo.).

Conjugates or Immunoconjugates

According to at least some embodiments, the present invention features immunoconjugates comprising an anti-T4, T5 or "skip 10" antibody, or a fragment thereof, conjugated to a therapeutic moiety, such as a cytotoxin, a drug (e.g., an immunosuppressant) or a radiotoxin. Such conjugates are referred to herein as "immunoconjugates" Immunoconjugates that include one or more cytotoxins are referred to as "immunotoxins." A cytotoxin or cytotoxic agent includes any agent that is detrimental to (e.g., kills) cells. Examples include taxol, cytochalasin B, gramicidin D, ethidium bromide, emetine, mitomycin, etoposide, tenoposide, vincristine, vinblastine, colchicin, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, and puromycin and analogs or homologs thereof. Therapeutic agents also include, for example, antimetabolites (e.g., methotrexate, 6-mercaptopurine, 6-thioguanine, cytarabine, 5-fluorouracil decarbazine), alkylating agents (e.g., mechlorethamine, thioepa chlorambucil, melphalan, carmustine (BSNU) and lomustine (CCNU), cyclothosphamide, busulfan, dibromomannitol, streptozotocin, mitomycin C, and cis-dichlorodiamine platinum (II) (DDP) cisplatin), anthracyclines (e.g., daunorubicin (formerly daunomycin) and doxorubicin), antibiotics (e.g., dactinomycin (formerly actinomycin), bleomycin, mithramycin, and anthramycin (AMC)), and anti-mitotic agents (e.g., vincristine and vinblastine).

Other preferred examples of therapeutic cytotoxins that can be conjugated to an antibody according to at least some embodiments of the invention include duocarmycins, calicheamicins, maytansines and auristatins, and derivatives thereof. An example of a calicheamicin antibody conjugate is commercially available (Mylotarg™; Wyeth).

Cytotoxins can be conjugated to antibodies according to at least some embodiments of the invention using linker technology available in the art. Examples of linker types that have been used to conjugate a cytotoxin to an antibody include, but are not limited to, hydrazones, thioethers, esters, disulfides and peptide-containing linkers. A linker can be chosen that is, for example, susceptible to cleavage by low pH within the lysosomal compartment or susceptible to cleavage by proteases, such as proteases preferentially expressed in tumor tissue such as cathepsins (e.g., cathepsins B, C, D).

For further discussion of types of cytotoxins, linkers and methods for conjugating therapeutic agents to antibodies, see also Saito, G. et al. (2003) Adv. Drug Deliv. Rev. 55:199-215; Trail, P. A. et al. (2003) Cancer Immunol. Immunother. 52:328-337; Payne, G. (2003) Cancer Cell 3:207-212; Allen, T. M. (2002) Nat. Rev. Cancer 2:750-763; Pastan, I. and Kreitman, R. J. (2002) Curr. Opin. Investig. Drugs 3:1089-1091; Senter, P. D. and Springer, C. J. (2001) Adv. Drug Deliv. Rev. 53:247-264.

Antibodies according to at least some embodiments of the present invention also can be conjugated to a radioactive isotope to generate cytotoxic radiopharmaceuticals, also referred to as radioimmunoconjugates. Examples of radioactive isotopes that can be conjugated to antibodies for use diagnostically or therapeutically include, but are not limited to, iodine 131, indium 111, yttrium 90 and lutetium 177. Method for preparing radioimmunconjugates are established in the art. Examples of radioimmunoconjugates are commercially available, including Zevalin™ (IDEC Pharmaceuticals) and Bexxar™ (Corixa Pharmaceuticals), and similar methods can be used to prepare radioimmunoconjugates using the antibodies according to at least some embodiments of the invention.

The antibody conjugates according to at least some embodiments of the invention can be used to modify a given biological response, and the drug moiety is not to be construed as limited to classical chemical therapeutic agents. For example, the drug moiety may be a protein or polypeptide possessing a desired biological activity. Such proteins may include, for example, an enzymatically active toxin, or active fragment thereof, such as abrin, ricin A, *pseudomonas* exotoxin, or diphtheria toxin; a protein such as tumor necrosis factor or interferon-.gamma.; or, biological response modifiers such as, for example, lymphokines, interleukin-1 ("IL-1"), interleukin-2 ("IL-2"), interleukin-6 ("IL-6"), granulocyte macrophage colony stimulating factor ("GM-CSF"), granulocyte colony stimulating factor ("G-CSF"), or other growth factors.

Techniques for conjugating such therapeutic moiety to antibodies are well known, see, e.g., Arnon et al., "Monoclonal Antibodies For Immunotargeting Of Drugs In Cancer Therapy", in Monoclonal Antibodies And Cancer Therapy, Reisfeld et al. (eds.), pp. 243-56 (Alan R. Liss, Inc. 1985); Hellstrom et al., "Antibodies For Drug Delivery", in Controlled Drug Delivery (2nd Ed.), Robinson et al. (eds.), pp. 623-53 (Marcel Dekker, Inc. 1987); Thorpe, "Antibody Carriers Of Cytotoxic Agents In Cancer Therapy: A Review", in Monoclonal Antibodies '84: Biological And Clinical Applications, Pinchera et al. (eds.), pp. 475-506 (1985); "Analysis, Results, And Future Prospective Of The Therapeutic Use Of Radiolabeled Antibody In Cancer Therapy", in Monoclonal Antibodies For Cancer Detection And Therapy, Baldwin et al. (eds.), pp. 303-16 (Academic Press 1985), and Thorpe et al., "The Preparation And Cytotoxic Properties Of Antibody-Toxin Conjugates", Immunol. Rev., 62:119-58 (1982).

Bispecific Molecules

In another aspect, the present invention features bispecific molecules comprising an anti-T4, T5 or "skip 10" antibody, or a fragment thereof, according to at least some embodiments of the invention. An antibody according to at least some embodiments of the invention, or antigen-binding portions thereof, can be derivatized or linked to another functional molecule, e.g., another peptide or protein (e.g., another antibody or ligand for a receptor) to generate a bispecific molecule that binds to at least two different binding sites or target molecules. The antibody according to at least some embodiments of the invention may in fact be derivatized or linked to more than one other functional molecule to generate multispecific molecules that bind to more than two different binding sites and/or target molecules; such multispecific molecules are also intended to be encompassed by the term "bispecific molecule" as used herein. To create a bispecific molecule according to at least some embodiments of the invention, an antibody according to at least some embodiments of the invention can be functionally linked (e.g., by chemical coupling, genetic fusion, noncovalent association or otherwise) to one or more other binding molecules, such as another antibody, antibody fragment, peptide or binding mimetic, such that a bispecific molecule results.

Accordingly, the present invention includes bispecific molecules comprising at least one first binding specificity for a T4, T5 or "skip 10" polypeptide and a second binding specificity for a second target epitope. In a particular embodiment according to at least some embodiments of the invention, the second target epitope is an Fc receptor, e.g., human Fc gamma RI (CD64) or a human Fc alpha receptor (CD89). Therefore, the invention includes bispecific molecules capable of binding both to Fc gamma R, Fc alpha R or Fc epsilon R expressing effector cells (e.g., monocytes, macrophages or polymorphonuclear cells (PMNs)), and to target cells expressing a T4, T5 or "skip 10" polypeptide, respectively. These bispecific molecules target T4, T5 or "skip 10" polypeptide expressing cells to effector cell and trigger Fc receptor-mediated effector cell activities, such as phagocytosis of T4, T5 or "skip 10" polypeptide expressing cells, antibody dependent cell-mediated cytotoxicity (ADCC), cytokine release, or generation of superoxide anion.

In an embodiment according to at least some embodiments of the invention in which the bispecific molecule is multispecific, the molecule can further include a third binding specificity, in addition to an anti-Fc binding specificity and an anti-6f binding specificity. In one embodiment, the third binding specificity is an anti-enhancement factor (EF) portion, e.g., a molecule which binds to a surface protein involved in cytotoxic activity and thereby increases the immune response against the target cell.

The "anti-enhancement factor portion" can be an antibody, functional antibody fragment or a ligand that binds to a given molecule, e.g., an antigen or a receptor, and thereby results in an enhancement of the effect of the binding determinants for the Fc receptor or target cell antigen. The "anti-enhancement factor portion" can bind an Fc receptor or a target cell antigen. Alternatively, the anti-enhancement factor portion can bind to an entity that is different from the entity to which the first and second binding specificities bind. For example, the anti-enhancement factor portion can bind a cytotoxic T-cell (e.g., via CD2, CD3, CD8, CD28, CD4, CD40, ICAM-1 or other immune cell that results in an increased immune response against the target cell).

In one embodiment, the bispecific molecules according to at least some embodiments of the invention comprise as a binding specificity at least one antibody, or an antibody fragment thereof, including, e.g., an Fab, Fab', F(ab')2, Fv, or a single chain Fv. The antibody may also be a light chain or heavy chain dimer, or any minimal fragment thereof such as a Fv or a single chain construct as described in Ladner et al. U.S. Pat. No. 4,946,778, the contents of which is expressly incorporated by reference.

The production and characterization of certain preferred anti-Fc gamma. monoclonal antibodies are described by Fanger et al. in PCT Publication WO 88/00052 and in U.S. Pat. No. 4,954,617, the teachings of which are fully incorporated by reference herein. These antibodies bind to an epitope of Fc R1, FcγRII or FcγRIII at a site which is distinct from the Fc binding site of the receptor and, thus, their binding is not blocked substantially by physiological levels of IgG. Specific anti-Fc RI antibodies useful in this invention are mAb 22, mAb 32, mAb 44, mAb 62 and mAb 197. The hybridoma producing mAb 32 is available from the American Type Culture Collection, ATCC Accession No. HB9469. In other embodiments, the anti-Fcγ receptor antibody is a humanized form of monoclonal antibody 22 (H22).

The production and characterization of the H22 antibody is described in Graziano, R. F. et al. (1995) J. Immunol. 155 (10): 4996-5002 and PCT Publication WO 94/10332. The H22 antibody producing cell line is deposited at the American Type Culture Collection under the designation HAO22CLI and has the accession no. CRL 11177.

In still other preferred embodiments, the binding specificity for an Fc receptor is provided by an antibody that binds to a human IgA receptor, e.g., an Fc-alpha receptor (Fc alpha RI(CD89)), the binding of which is preferably not blocked by human immunoglobulin A (IgA). The term "IgA receptor" is intended to include the gene product of one alpha.-gene (Fc alpha RI) located on chromosome 19. This gene is known to encode several alternatively spliced transmembrane isoforms of 55 to 10 kDa.

Fc alpha RI (CD89) is constitutively expressed on monocytes/macrophages, eosinophilic and neutrophilic granulocytes, but not on non-effector cell populations. Fc alpha RI has medium affinity (Approximately $5 \times 10^{-7}$ M-1) for both IgA1 and IgA2, which is increased upon exposure to cytokines such as G-CSF or GM-CSF (Morton, H. C. et al. (1996) Critical Reviews in Immunology 16:423-440). Four Fca RI-specific monoclonal antibodies, identified as A3, A59, A62 and A77, which bind Fc alpha RI outside the IgA ligand binding domain, have been described (Monteiro, R. C. et al. (1992) J. Immunol. 148:1764).

Fc alpha RI and Fc gamma RI are preferred trigger receptors for use in the bispecific molecules according to at least some embodiments of the invention because they are (1) expressed primarily on immune effector cells, e.g., monocytes, PMNs, macrophages and dendritic cells; (2) expressed at high levels (e.g., 5,000-100,000 per cell); (3) mediators of cytotoxic activities (e.g., ADCC, phagocytosis); (4) mediate enhanced antigen presentation of antigens, including self-antigens, targeted to them.

While human monoclonal antibodies are preferred, other antibodies which can be employed in the bispecific molecules according to at least some embodiments of the invention are murine, chimeric and humanized monoclonal antibodies.

The bispecific molecules according to at least some embodiments of the present invention can be prepared by conjugating the constituent binding specificities, e.g., the anti-FcR and anti-T4, T5 or "skip 10" polypeptide binding specificities, using methods known in the art. For example, each binding specificity of the bispecific molecule can be generated separately and then conjugated to one another. When the binding specificities are proteins or peptides, a variety of coupling or cross-linking agents can be used for covalent conjugation. Examples of cross-linking agents include protein A, carbodiimide, N-succinimidyl-S-acetyl-thioacetate (SATA), 5,5'-dithiobis(2-nitrobenzoic acid) (DTNB), o-phenylenedimaleimide (oPDM), N-succinimidyl-3-(2-pyridyld-ithio)propionate (SPDP), and sulfosuccinimidyl 4-(N-maleimidomethyl) cyclohaxane-1-carboxylate (sulfo-SMCC) (see e.g., Karpovsky et al. (1984) J. Exp. Med. 160:1686; Liu, M A et al. (1985) Proc. Natl. Acad. Sci. USA 82:8648). Other methods include those described in Paulus (1985) Behring Ins. Mitt. No. 78, 118-132; Brennan et al. (1985) Science 229:81-83), and Glennie et al. (1987) J. Immunol. 139: 2367-2375). Preferred conjugating agents are SATA and sulfo-SMCC, both available from Pierce Chemical Co. (Rockford, Ill.).

When the binding specificities are antibodies, they can be conjugated via sulfhydryl bonding of the C-terminus hinge regions of the two heavy chains. In a particularly preferred embodiment, the hinge region is modified to contain an odd number of sulfhydryl residues, preferably one, prior to conjugation.

Alternatively, both binding specificities can be encoded in the same vector and expressed and assembled in the same host cell. This method is particularly useful where the bispecific molecule is a mAbXmAb, mAbXFab, FabXF(ab')2 or ligandXFab fusion protein. A bispecific molecule according to at least some embodiments of the invention can be a single chain molecule comprising one single chain antibody and a binding determinant, or a single chain bispecific molecule comprising two binding determinants. Bispecific molecules may comprise at least two single chain molecules. Methods for preparing bispecific molecules are described for example in U.S. Pat. No. 5,260,203; U.S. Pat. No. 5,455,030; U.S. Pat. No. 4,881,175; U.S. Pat. No. 5,132,405; U.S. Pat. No. 5,091,513; U.S. Pat. No. 5,476,786; U.S. Pat. No. 5,013,653; U.S. Pat. No. 5,258,498; and U.S. Pat. No. 5,482,858.

Binding of the bispecific molecules to their specific targets can be confirmed by, for example, enzyme-linked immunosorbent assay (ELISA), radioimmunoassay (RIA), FACS analysis, bioassay (e.g., growth inhibition), or Western Blot assay. Each of these assays generally detects the presence of protein-antibody complexes of particular interest by employing a labeled reagent (e.g., an antibody) specific for the complex of interest. For example, the FcR-antibody complexes can be detected using e.g., an enzyme-linked antibody or antibody fragment which recognizes and specifically binds to the antibody-FcR complexes. Alternatively, the complexes can be detected using any of a variety of other immunoassays. For example, the antibody can be radioactively labeled and used in a radioimmunoassay (RIA) (see, for example, Weintraub, B., Principles of Radioimmunoassays, Seventh Training Course on Radioligand Assay Techniques, The Endocrine Society, March, 1986, which is incorporated by reference herein). The radioactive isotope can be detected by such means as the use of a gamma. counter or a scintillation counter or by autoradiography.

Pharmaceutical Compositions

In another aspect, the present invention provides a composition, e.g., a pharmaceutical composition, containing one or a combination of monoclonal antibodies, or antigen-binding portions thereof, according to at least some embodiments of the present invention, formulated together with a pharmaceutically acceptable carrier. Such compositions may include one or a combination of (e.g., two or more different) antibodies, or immunoconjugates or bispecific molecules according to at least some embodiments of the invention. For example, a pharmaceutical composition according to at least some embodiments of the invention can comprise a combination of antibodies (or immunoconjugates or bispecifics) that bind to different epitopes on the target antigen or that have complementary activities.

As discussed supra, at least some embodiments of the present invention further embrace identifying other molecules such as small organic molecules, peptides, ribozymes, carbohydrates, glycoprotein, siRNAs, antisense RNAs and the like which specifically bind and/or modulate (enhance or inhibit) an activity elicited by the T4, T5 or "skip 10" antigen or polypeptides, respectively. These molecules may be identified by known screening methods such as binding assays. Typically these assays will be high throughput and will screen a large library of synthesized or native compounds in order to identify putative drug candidates that bind and/or modulate T4, T5 or "skip 10" related activities. According to at least some embodiments, the pharmaceutical composition comprises one or a combination of ribosymes, siRNAs and antisense RNAs, which specifically bind and/or modulate (enhance or inhibit) the activity elicited by any one of the T4, T5 or "skip 10" antigens or polypeptides.

The pharmaceutical composition according to the present invention is further optionally used for the treatment of cancer.

The therapeutic agents according to at least some embodiments of the present invention can be provided to the subject alone, or as part of a pharmaceutical composition where they are mixed with a pharmaceutically acceptable carrier.

Pharmaceutical compositions according to at least some embodiments of the invention also can be administered in combination therapy, i.e., combined with other agents. For example, the combination therapy can include an anti-T4, T5 or "skip 10" antibody or T4, T5 or "skip 10" modulating agent according to the present invention such as a small molecule such as a peptide, ribozyme, siRNA, or other drug that binds a T4, T5 or "skip 10" polypeptide, combined with at least one other therapeutic or immune modulatory agent.

A composition according to at least some embodiments of the present invention can be administered via one or more routes of administration using one or more of a variety of methods known in the art. As will be appreciated by the skilled artisan, the route and/or mode of administration will vary depending upon the desired results. Preferred routes of administration for antibodies according to at least some embodiments of the invention include intravenous, intramuscular, intradermal, intraperitoneal, subcutaneous, spinal or other parenteral routes of administration, for example by injection or infusion. The phrase "parenteral administration" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal, epidural and intrasternal injection and infusion. Preferred routes of administration for pharmaceutical compositions comprising inducing polypeptides or polynucleotides according to at least some embodiments of the invention include intravenous, intracoronary, intra-aortic, intrafemoral, intrapopliteal, intrapedialis, intra-posterior tibialis, intracarotideal and intraradialis routes. The pharmaceutical compound may be also administered by intrapericardial, intra-amniotic sac, intrapleural, intramyocardial-transepicardial, intramyocardial-transendocardial, intra-peripheral muscle, subcutaneous, intraspinal, and intracardiac (intra-atrial and intraventricular) routes. In addition, the inducing agent may be administered by sublingual, inhalatory, oral, rectal, periadventitial, perivascular, topical epicardial, topical epidermal, transdermal, ophthalmic routes or through theconjunctival, nasopharyngeal, bucopharyngeal, laryngopharyngeal, vaginal, colonic, urethral and vesical mucoses. Preferably, the inducing agent is administered by intramyocardial-transepicardial or intramyocardial-transendocardial injections. Moreprefer- ably, the inducing agent is administered by intramyocardial-transepicardial injection. In one embodiment of parenteral administration, the polynucleotide is administered in vehicles that are microbubbles, and the microbubbles are then disrupted byultrasound directed at a site of interest, such that the polynucleotide is released at and introduced into the site of interest. The ultrasound treatment permits one to direct the release of the polynucleotide by disruption of the bubbles at thespecific site at which the ultrasound is directed.

As used herein, "pharmaceutically acceptable carrier" includes any and all solvents, dispersion media, coatings, antibacterial and antifungal agents, isotonic and absorption delaying agents, and the like that are physiologically compatible. Preferably, the carrier is suitable for intravenous, intramuscular, subcutaneous, parenteral, spinal or epidermal administration (e.g., by injection or infusion). Depending on the route of administration, the active compound, i.e., antibody, immunoconjugate, or bispecific molecule, may be coated in a material to protect the compound from the action of acids and other natural conditions that may inactivate the compound.

A pharmaceutical composition according to at least some embodiments of the invention also may include a pharmaceutically acceptable anti-oxidant. Examples of pharmaceutically acceptable antioxidants include: (1) water soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal chelating agents, such as citric acid, ethylenediamine tetraacetic acid (EDTA), sorbitol, tartaric acid, phosphoric acid, and the like. Examples of suitable aqueous and nonaqueous carriers that may be employed in the pharmaceutical compositions according to at least some embodiments of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as preservatives, wetting agents, emulsifying agents and dispersing agents. Prevention of presence of microorganisms may be ensured both by sterilization procedures, supra, and by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption such as aluminum monostearate and gelatin.

Pharmaceutically acceptable carriers include sterile aqueous solutions or dispersions and sterile powders for the extemporaneous preparation of sterile injectable solutions or dispersion. The use of such media and agents for pharmaceutically active substances is known in the art. Except insofar as any conventional media or agent is incompatible with the active compound, use thereof in the pharmaceutical compositions according to at least some embodiments of the invention is contemplated. Supplementary active compounds can also be incorporated into the compositions.

Therapeutic compositions typically must be sterile and stable under the conditions of manufacture and storage. The composition can be formulated as a solution, microemulsion, liposome, or other ordered structure suitable to high drug concentration. The carrier can be a solvent or dispersion medium containing, for example, water, ethanol, polyol (for example, glycerol, propylene glycol, and liquid polyethylene glycol, and the like), and suitable mixtures thereof.

The proper fluidity can be maintained, for example, by the use of a coating such as lecithin, by the maintenance of the required particle size in the case of dispersion and by the use of surfactants. In many cases, it will be preferable to include isotonic agents, for example, sugars, polyalcohols such as mannitol, sorbitol, or sodium chloride in the composition. Prolonged absorption of the injectable compositions can be brought about by including in the composition an agent that delays absorption, for example, monostearate salts and gelatin. Sterile injectable solutions can be prepared by incorporating the active compound in the required amount in an appropriate solvent with one or a combination of ingredients enumerated above, as required, followed by sterilization microfiltration. Generally, dispersions are prepared by incorporating the active compound into a sterile vehicle that contains a basic dispersion medium and the required other ingredients from those enumerated above. In the case of sterile powders for the preparation of sterile injectable solutions, the preferred methods of preparation are vacuum drying and freeze-drying (lyophilization) that yield a powder of the active ingredient plus any additional desired ingredient from a previously sterile-filtered solution thereof.

Sterile injectable solutions can be prepared by incorporating the active compound in the required amount in an appropriate solvent with one or a combination of ingredients enumerated above, as required, followed by sterilization microfiltration. Generally, dispersions are prepared by incorporating the active compound into a sterile vehicle that contains a basic dispersion medium and the required other ingredients from those enumerated above. In the case of sterile powders for the preparation of sterile injectable solutions, the preferred methods of preparation are vacuum drying and freeze-drying (lyophilization) that yield a powder of the active ingredient plus any additional desired ingredient from a previously sterile-filtered solution thereof.

The amount of active ingredient which can be combined with a carrier material to produce a single dosage form will vary depending upon the subject being treated, and the particular mode of administration. The amount of active ingredient which can be combined with a carrier material to produce a single dosage form will generally be that amount of the composition which produces a therapeutic effect. Generally, out of one hundred percent, this amount will range from about 0.01 percent to about ninety-nine percent of active ingredient, optionally from about 0.1 percent to about 70 percent, optionally from about 1 percent to about 30 percent of active ingredient in combination with a pharmaceutically acceptable carrier.

Dosage regimens are adjusted to provide the optimum desired response (e.g., a therapeutic response). For example, a single bolus may be administered, several divided doses may be administered over time or the dose may be proportionally reduced or increased as indicated by the exigencies of the therapeutic situation. It is especially advantageous to formulate parenteral compositions in dosage unit form for ease of administration and uniformity of dosage. Dosage unit form as used herein refers to physically discrete units suited as unitary dosages for the subjects to be treated; each unit contains a predetermined quantity of active compound calculated to produce the desired therapeutic effect in association with the required pharmaceutical carrier. The specification for the dosage unit forms according to at least some embodiments of the invention are dictated by and directly dependent on (a) the unique characteristics of the active compound and the particular therapeutic effect to be achieved, and (b) the limitations inherent in the art of compounding such an active compound for the treatment of sensitivity in individuals.

For administration of the antibody, the dosage ranges from about 0.0001 to 100 mg/kg, and more usually 0.01 to 5 mg/kg, of the host body weight. For example dosages can be 0.3 mg/kg body weight, 1 mg/kg body weight, 3 mg/kg body weight, 5 mg/kg body weight or 10 mg/kg body weight or within the range of 1-10 mg/kg. An exemplary treatment regime entails administration once per week, once every two weeks, once every three weeks, once every four weeks, once a month, once every 3 months or once every three to 6 months.

Alternatively, antibody can be administered as a sustained release formulation, in which case less frequent administration is required. Dosage and frequency vary depending on the half-life of the antibody in the patient. In general, human antibodies show the longest half life, followed by humanized antibodies, chimeric antibodies, and nonhuman antibodies. The dosage and frequency of administration can vary depending on whether the treatment is prophylactic or therapeutic. In prophylactic applications, a relatively low dosage is administered at relatively infrequent intervals over a long period of time. Some patients continue to receive treatment for the rest of their lives. In therapeutic applications, a relatively high dosage at relatively short intervals is sometimes required until progression of the disease is reduced or terminated, and preferably until the patient shows partial or complete amelioration of symptoms of disease. Thereafter, the patient can be administered a prophylactic regime.

Actual dosage levels of the active ingredients in the pharmaceutical compositions according to at least some embodiments of the present invention may be varied so as to obtain an amount of the active ingredient which is effective to achieve the desired therapeutic response for a particular patient, composition, and mode of administration, without being toxic to the patient. The selected dosage level will depend upon a variety of pharmacokinetic factors including the activity of the particular compositions according to at least some embodiments of the present invention employed, or the ester, salt or amide thereof, the route of administration, the time of administration, the rate of excretion of the particular compound being employed, the duration of the treatment, other drugs, compounds and/or materials used in combination with the particular compositions employed, the age, sex, weight, condition, general health and prior medical history of the patient being treated, and like factors well known in the medical arts.

A "therapeutically effective dosage" of an anti-T4, T5 or "skip 10" antibody according to at least some embodiments of the invention preferably results in a decrease in severity of disease symptoms, an increase in frequency and duration of disease symptom-free periods, an increase in lifespan, disease remission, or a prevention of impairment or disability due to the disease affliction. For example, for the treatment of T4, T5 or "skip 10" polypeptide positive tumors, e.g., ovarian tumors, lung tumors, breast tumors, colon tumors, kidney tumors, liver tumors, pancreatic tumors, prostate cancer, melanoma and hematological malignancies such as Multiple Myeloma, lymphoma, Non-Hodgkin's lymphoma, leukemia, T cell leukemia, a "therapeutically effective dosage" optionally inhibits cell growth or tumor growth by at least about 20%, 40%, 60%, 80% relative to untreated subjects. The ability of a compound to inhibit tumor growth can be evaluated in an animal model system predictive of efficacy in human tumors. Alternatively, this property of a composition can be evaluated by examining the ability of the compound to inhibit, such inhibition in vitro by assays known to the skilled practitioner.

Alternatively or additionally, a "therapeutically effective dosage" preferably results in at least stable disease, preferably partial response, more preferably complete response, as assessed by the WHO or RECIST criteria for tumor response (Natl Cancer Inst 1999; 91:523-8 and Cancer 1981; 47:207-14).

A therapeutically effective amount of a therapeutic compound can decrease tumor size, or otherwise ameliorate symptoms in a subject, or otherwise support partial or complete stable disease and/or partial or complete response as determined above. One of ordinary skill in the art would be able to determine such amounts based on such factors as the subject's size, the severity of the subject's symptoms, and the particular composition or route of administration selected.

Therapeutic compositions can be administered with medical devices known in the art. For example, in a preferred embodiment, a therapeutic composition according to at least some embodiments of the invention can be administered with a needles hypodermic injection device, such as the devices disclosed in U.S. Pat. Nos. 5,399,163; 5,383,851; 5,312,335; 5,064,413; 4,941,880; 4,790,824; or 4,596,556. Examples of well-known implants and modules useful in the present invention include: U.S. Pat. No. 4,487,603, which discloses an implantable micro-infusion pump for dispensing medication at a controlled rate; U.S. Pat. No. 4,486,194, which discloses a therapeutic device for administering medicaments through the skin; U.S. Pat. No. 4,447,233, which discloses a medication infusion pump for delivering medication at a precise infusion rate; U.S. Pat. No. 4,447,224, which discloses a variable flow implantable infusion apparatus for continuous drug delivery; U.S. Pat. No. 4,439,196, which discloses an osmotic drug delivery system having multi-chamber compartments; and U.S. Pat. No. 4,475,196, which discloses an osmotic drug delivery system. These patents are incorporated herein by reference. Many other such implants, delivery systems, and modules are known to those skilled in the art.

In certain embodiments, the antibodies or other T4, T5 or "skip 10" related drugs according to at least some embodiments of the invention can be formulated to ensure proper distribution in vivo. For example, the blood-brain barrier (BBB) excludes many highly hydrophilic compounds. To ensure that the therapeutic compounds according to at least some embodiments of the invention cross the BBB (if desired), they can be formulated, for example, in liposomes. For methods of manufacturing liposomes, see, e.g., U.S. Pat. Nos. 4,522,811; 5,374,548; and 5,399,331. The liposomes may comprise one or more moieties which are selectively transported into specific cells or organs, thus enhance targeted drug delivery (see, e.g., V. V. Ranade (1989) J. Clin. Pharmacol. 29:685). Exemplary targeting moieties include folate or biotin (see, e.g., U.S. Pat. No. 5,416,016 to Low et al.); mannosides (Umezawa et al., (1988) Biochem. Biophys. Res. Commun 153:1038); antibodies (P. G. Bloeman et al. (1995) FEBS Lett. 357:140; M. Owais et al. (1995) Antimicrob. Agents Chemother. 39:180); surfactant protein A receptor (Briscoe et al. (1995) Am. J Physiol. 1233:134); p120 (Schreier et al. (1994) J. Biol. Chem. 269:9090); see also K. Keinanen; M. L. Laukkanen (1994) FEBS Lett. 346:123; J. J. Killion; I. J. Fidler (1994) Immunomethods 4:273.

Given the specific binding of the antibodies according to at least some embodiments of the invention for T4, T5 or "skip 10" polypeptides, the antibodies can be used to specifically detect T4, T5 or "skip 10" expression on the surface of cells and, moreover, can be used to purify T4, T5 or "skip 10" antigen via immunoaffinity purification.

Furthermore, given the expression of T4, T5 or "skip 10" polypeptides on various tumor cells, the human antibodies, antibody compositions and methods according to at least some embodiments of the present invention can be used to treat a subject with a tumorigenic disorder, e.g., a disorder characterized by the presence of tumor cells expressing T4, T5 or "skip 10" antigen such as ovarian cancer, colon cancer, lung cancer, breast cancer, kidney cancer, liver cancer, pancreatic cancer, prostate cancer, melanoma and hematological malignancies such as Multiple Myeloma, lymphoma, Non-Hodgkin's lymphoma, leukemia, T cell leukemia, as mentioned.

In one embodiment, the antibodies (e.g., human monoclonal antibodies, multispecific and bispecific molecules and compositions) according to at least some embodiments of the invention can be used to detect levels of a T4, T5 or "skip 10" polypeptide or levels of cells which contain a T4, T5 or "skip 10" polypeptide, respectively, on their membrane surface, which levels can then be linked to certain disease symptoms.

Alternatively, the antibodies can be used to inhibit or block functioning of T4, T5 or "skip 10" polypeptides which, in turn, can be linked to the prevention or amelioration of certain disease symptoms, thereby implicating T4, T5 or "skip 10" polypeptides, respectively, as a mediator of the disease. This can be achieved by contacting a sample and a control sample with the anti-T4, T5 or "skip 10" antibody under conditions that allow for the formation of a complex between the corresponding antibody and T4, T5 or "skip 10" polypeptides, respectively. Any complexes formed between the antibody and T4, T5 or "skip 10" polypeptides are detected and compared in the sample and the control.

In another embodiment, the antibodies (e.g., human antibodies, multispecific and bispecific molecules and compositions) according to at least some embodiments of the invention can be initially tested for binding activity associated with therapeutic or diagnostic use in vitro. For example, compositions according to at least some embodiments of the invention can be tested using low cytometric assays.

As previously described, human anti-T4, T5 or "skip 10" antibodies according to at least some embodiments of the invention can be co-administered with one or other more therapeutic agents, e.g., an cytotoxic agent, a radiotoxic agent or an immunosuppressive agent. The antibody can be linked to the agent (as an immunocomplex) or can be administered separate from the agent. In the latter case (separate administration), the antibody can be administered before, after or concurrently with the agent or can be co-administered with other known therapies, e.g., an anti-cancer therapy, e.g., radiation. Such therapeutic agents include, among others, anti-neoplastic agents such as doxorubicin (adriamycin), cisplatin bleomycin sulfate, carmustine, chlorambucil, and cyclophosphamide hydroxyurea which, by themselves, are only effective at levels which are toxic or subtoxic to a patient. Cisplatin is intravenously administered as a 100 mg/dose once every four weeks and adriamycin is intravenously administered as a 60-75 mg/ml dose once every 21 days. Co-administration of the human anti-T4, T5 or "skip 10" antibodies, or antigen binding fragments thereof, according to at least some embodiments of the present invention with chemotherapeutic agents provides two anti-cancer agents which operate via different mechanisms which yield a cytotoxic effect to human tumor cells. Such co-administration can solve problems due to development of resistance to drugs or a change in the antigenicity of the tumor cells which would render them unreactive with the antibody.

Also within the scope according to at least some embodiments of the present invention are kits comprising the T4, T5 or "skip 10" polypeptide or antibody compositions according to at least some embodiments of the invention (e.g., human antibodies, bispecific or multispecific molecules, or immunoconjugates) and instructions for use. The kit can further contain one or more additional reagents, such as an immunosuppressive reagent, a cytotoxic agent or a radiotoxic agent, or one or more additional human antibodies according to at least some embodiments of the invention (e.g., a human antibody having a complementary activity which binds to an epitope in the T4, T5 or "skip 10" antigen distinct from the first human antibody).

In other embodiments, the subject can be additionally treated with an agent that modulates, e.g., enhances or inhibits, the expression or activity of Fcγ or Fcγ receptors by, for example, treating the subject with a cytokine. Preferred cytokines for administration during treatment with the multispecific molecule include of granulocyte colony-stimulating factor (G-CSF), granulocyte-macrophage colony-stimulating factor (GM-CSF), interferon-.gamma. (IFN-.gamma.), and tumor necrosis factor (TNF).

The compositions (e.g., human antibodies, multispecific and bispecific molecules) according to at least some embodiments of the invention can also be used to target cells expressing Fc gamma R or T4, T5 or "skip 10", for example for labeling such cells. For such use, the binding agent can be linked to a molecule that can be detected. Thus, the invention provides methods for localizing ex vivo or in vitro cells expressing Fc receptors, such as FcgammaR, or T4, T5 or "skip 10" antigen. The detectable label can be, e.g., a radioisotope, a fluorescent compound, an enzyme, or an enzyme co-factor.

EXAMPLE 5

Methods of Treatment According to at Least Some Embodiments of the Present Invention As mentioned hereinabove the T4, T5 or "skip 10" proteins and polypeptides according to at least some embodiments of the present invention or nucleic acid sequence or fragments thereof especially the secreted forms of such proteins and polypeptides, such as T5 for example, can be used to treat cancer, including but not limited to lymphoma, especially Non-Hodgkin's Lymphoma, Multiple Myeloma, kidney cancer, Liver cancer and pancreatic cancer. Thus, according to at least some embodiments of the present invention there is provided a method of treating cancer.

Optionally such a method may feature altering one or more aspects of the protein, such as T5 for example, to enable it to block or antagonize a cancer related function. Alternatively or additionally, the protein, such as T5 for example, may be conjugated to a toxin or other substance which blocks or antagonizes a cancer related function. All of these options and alternatives are encompassed within "treatment".

As used herein the term "treating" refers to preventing, curing, reversing, attenuating, alleviating, minimizing, suppressing or halting the deleterious effects of the above-described diseases, disorders or conditions. The term treatment as used herein refers also to "maintenance therapy", which is a treatment that is given to keep a pathologic condition or disorder from coming back after it has disappeared following the initial therapy.

Treating, according to the present invention, can be effected by specifically upregulating the expression of at least one of the polypeptides according to at least some embodiments of the present invention in the subject.

Optionally, upregulation may be effected by administering to the subject at least one of the polypeptides according to at least some embodiments of the present invention (e.g., recombinant or synthetic) or an active portion thereof, as described herein. However, since the bioavailability of large polypeptides may potentially be relatively small due to high degradation rate and low penetration rate, administration of polypeptides is preferably confined to small peptide fragments (e.g., about 100 amino acids). The polypeptide or peptide may optionally be administered in as part of a pharmaceutical composition, described in more detail below.

It will be appreciated that treatment of the above-described diseases according to the present invention may be combined with other treatment methods known in the art (i.e., combination therapy).

EXAMPLE 6

Clinical Significance of Heparanase T5 Splice Variant: Development of T5-Specific Monoclonal Antibodies In heparanase T5 splice variant, 144 bp of intron 5 are joined with exon 4, resulting in a truncated, enzymatically inactive protein. T5 over-expression resulted in increased cell proliferation and larger colonies in soft agar, mediated by Src activation. Furthermore, T5 over-expression markedly enhanced tumor xenograft development. T5 expression is up-regulated in 75% of human renal cell carcinoma biopsies examined, suggesting that this splice variant is clinically relevant (as described in Example 1, FIG. 6 herein). To investigate the significance and contribution of T5 to human tumor progression, generation of reagents (i.e., inhibitors, antibodies) specific for T5 was required. These specific reagents would react with T5 but not wild type (known) heparanase. T5 is thought to assume a distinct three-dimensional conformation which is different from that of the wild type (WT) heparanase protein. This feature was exploited to generate monoclonal antibodies recognizing the unique structure of T5 without, or with minimal recognition of WT heparanase.

Cloning and Expression of MBP-T5 Fusion Protein

The plasmid for expression and purification of maltose binding protein (MBP)-T5 fusion protein used pMAL-p2X (#N8077S; New England BioLabs (Beverly, Mass.)) as its base and included the T5 sequence set forth in SEQ ID NO:16, encoding the T5 heparanase variant protein set forth in SEQ ID NO:15, fused to the MBP polynucleotide sequence. The cloning and expression of the fusion protein was carried out according to Guan C. et al, Gene 67: 21-30, 1987; Maina C V et al, Gene 74: 365-373, 1988.

Generation of Anti-T5 Monoclonal Antibodies (mAb).

Anti-T5 mAb, including the 9c9 antibody, were generated according to established protocol (Harlow Ed and David Lane, Antibodies-A laboratory manual. Cold Spring Harbor Laboratory, 1988).

Briefly, Balb/c mice were immunized with MBP-T5 fusion protein mixed with complete Freund's adjuvant (Sigma) followed by three immunization with incomplete adjuvant, all administrated i.p. Mice were injected i.v. with MBP-T5 in PBS; spleen was harvested three days later and splenocytes were fused with NSO myeloma cells (ATCC accession No: CRL 11705). Hybridomas were screened 10 days later by ELISA plates coated with recombinant heparanase. Positive hybridomas were further expanded and single cell clones were isolated by ELISA.

The 9c9 hybridomas have been submitted for deposit according to the provisions of the Budapest Treaty with European Collection of Cell Cultures, Health Protection Agency Culture Collections (Centre for Emergency Preparedness & Response, Porton Down, Salisbury SP4 0JG, United Kingdom) on 11 Nov. 2010 (ECACC Accession Number: 10111101).

Staining Protocol for Anti-T5 9c9 Monoclonal Antibody:

Sections were de-waxed with xylene—5 min×2 and rinsed in 100% alcohol. The endogenous peroxidase activity was blocked with hydrogen peroxide in methanol for 30 min (50 ml methanol, 1.5 ml 30% $H_2O_2$), and the sections were rinsed in alcohol 100%; alcohol 70% and then in double distilled water, and kept in water until ready for antigen retrieval.

Antigen retrival was performed in Sodium Citrate Buffer (10 mM Sodium Citrate, pH 6.0). The slides, in an appropriate rack, were boiled for 20 min in a microwave oven (samples were kept completely covered with liquid), then rinsed in water, washed with phosphate buffered saline (PBS), and blocked with 10% goat serum (in PBS) for 1 hour at room temp.

The sections were incubated with anti-T5 9c9 monoclonal antibody diluted 1:200 in blocking solution overnight at 4° c., and then were incubated for 30 min at room temperature. Following a rinse in phosphate buffered saline three times, 5 minutes for each rinse, the slides were reacted with Alk Phos Detection Kit reagent according to the manufacturer's instructions(Cell Marque, Rocklin Calif.; ITEM #952D-20), washed with PBS and a permanent red dye (ITEM #960D-20, Cell Marque) was applied for 5 min, according to the manufacturer's instructions. Finally, the slides were counterstained with hematoxylin and mounted (Immu-Mount; Thermo Shandon Cat no 9990402).

Results

Figure 11A:
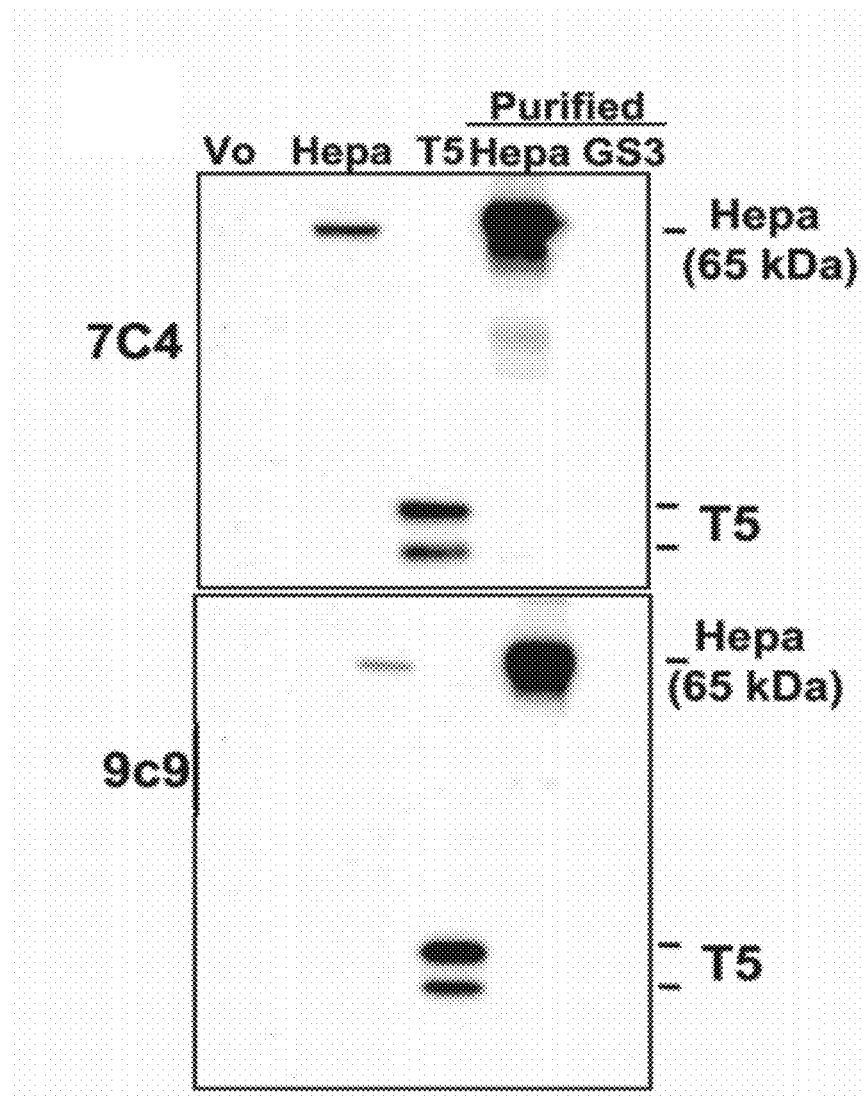
FIG. 11A presents the immunoblotting results with 7c4 antibody as compared to 9c9 antibody.

The results of the screen of hybridomas generated against recombinant MBP-T5 fusion protein are shown in FIG. 11. While antibody 7c4 recognized the WT heparanase and T5 to a similar extent during immunoblotting, antibody 9c9 preferentially reacted with T5 (FIG. 11A). Notably, the epitope of both antibodies is localized to the linker region of pro-heparanase which is removed by proteolytic processing and is not present in the active enzyme, as previously described (FIG. 11A, GS3). These results suggested that the generation of T5-specific monoclonal antibodies is feasible.

In order to explore whether the antibodies are suitable for immunohistochemical analysis, tumor xenografts were subjected to immunostaining. Notably, the specificity observed by immunoblotting was also seen in staining. Thus, antibody 7c4 reacted with tumor xenografts generated by CAG myeloma cells over expressing heparanase or T5 (FIG. 11B, left). In contrast, antibody 9c9 only reacted with tumor xenografts produced by CAG cells over expressing T5 (FIG. 11B, right lower panel).

Next the ability of antibody 9c9 to stain human tumor biopsies was examined A cohort of renal cell carcinoma (RCC) specimens collected at the Bnai-Zion Medical Center (Haifa, Israel) was subjected to immunostaining applying antibody 9c9 and staining intensity was scored. Notably, while staining was not detected in some specimens (FIG. 11C, upper panel), others stained strongly with antibody 9c9 (FIG. 11C, middle panel). In addition to the reactivity with tumor cells, antibody 9c9 also stained endothelial cells lining blood vessels (FIG. 11C, lower panel), in agreement with pro-angiogenic activity of T5.

As evident from the characterization data of the 9c9 hybridoma, the region recognized by the T5 specific mAb is within the linker region of the protein. This region is common to both proteins, but clearly the 9c9 hybridoma derived mAb binds T5 in denatured form preferentially, as demonstrated by Western blotting, and only T5 in its native form, as demonstrated by the immunohistochemistry. Clearly T5 adopts a different conformation structure as compared to the WT protein, and possesses one or more novel conformational epitopes to which 9c9 hybridoma derived mAb specifically bind.

EXAMPLE 7

Diagnostic Methods, Markers and Kits According to at Least Some Embodiments of the Present Invention In certain embodiments the polypeptides and/or polynucleotides according to at least some embodiments of the present invention are used as markers for diagnosis of diseases wherein T4, T5 or "skip 10" polypeptides and/or polynucleotides are differentially present. According to at least some embodiments, the diseases optionally include but are not limited to cancer.

According to further embodiments markers according to at least some embodiments of the present invention might optionally be used alone or in combination one or more other compounds described herein, and/or in combination with known markers for lung cancer, including but not limited to CEA, CA15-3, Beta-2-microglobulin, CA19-9, TPA, and/or in combination with the known proteins for the variant marker as described herein.

According to further embodiments markers according to at least some embodiments of the present invention might optionally be used alone or in combination with one or more other compounds described herein, and/or in combination known markers for ovarian cancer, including but not limited to CEA, CA125 (Mucin 16), CA72-4TAG, CA-50, CA 54-61, CA-195 and CA 19-9 in combination with CA-125, and/or in combination with the known proteins for the variant marker as described herein.

According to further embodiments markers according to at least some embodiments of the present invention might optionally be used alone or in combination with one or more other compounds described herein, and/or in combination with known markers for breast cancer, including but not limited to Calcitonin, CA15-3 (Mucin1), CA27-29, TPA, a combination of CA 15-3 and CEA, CA 27.29 (monoclonal antibody directed against MUC1), Estrogen 2 (beta), HER-2 (c-erbB2), and/or in combination with the known proteins for the variant marker as described herein.

According to further embodiments markers according to at least some embodiments of the present invention might optionally be used alone or in combination with one or more other compounds described herein, and/or in combination with known markers for renal cancer, including but not limited to urinary protein, creatinine or creatinine clearance, and/or markers used for the diagnosis or assessment of prognosis of renal cancer, specifically of renal cell carcinoma, including but not limited to vascular endothelial growth factor, interleukin-12, the soluble interleukin-2 receptor, intercellular adhesion molecule-1, human chorionic gonadotropin beta, insulin-like growth factor-1 receptor, Carbonic anhydrase 9 (CA 9), endostatin, Thymidine phosphorylase and/or in combination with the known proteins for the variant marker as described herein.

According to further embodiments markers according to at least some embodiments of the present invention might optionally be used alone or in combination with one or more other compounds described herein, and/or in combination with known markers for liver cancer, including but not limited to Alpha fetoprotein (AFP), des-gamma-carboxyprothrombin (DCP), Squamous cell carcinoma antigen (SCCA)-immunoglobulin M (IgM), AFP (L3), or fucosylated AFP, GP73 (a golgi protein marker) and its fucosylated form, (TGF)-beta1, HS-GGT, free insulin-like growth factor (IGF)-II.

According to further embodiments markers according to at least some embodiments of the present invention might optionally be used alone or in combination with one or more other compounds described herein, and/or in combination with known markers for melanoma cancer, including but not limited to S100-beta, melanoma inhibitory activity (MIA), lactate dehydrogenase (LDH), tyrosinase, 5-S-Cysteinyldopa, L-Dopa/L-tyrosine, VEGF, bFGF, IL-8, ICAM-1, MMPs, IL-6, IL-10, sIL-2R (soluble interleukin-2-receptor), sHLA-DR (soluble HLA-DR), sHLA-class-I (soluble HLA-class I), TuM2-PK, Fas/CD95, sHLA-class-I (soluble HLA-class I), Albumin, TuM2-PK (Tumour pyruvate kinase type M2), sFas/CD95, YKL-40, CYT-MAA (cytoplasmic melanoma-associated antigen), HMW-MAA (high-molecular-weight melanoma-associated antigen), STATS, STAT1, gp100/HMB45, p16 INK4A, PTEN, pRb (retinoblastoma protein), EGFR, p-Akt, c-Kit, c-myc, AP-2, HDM2, bcl-6, Ki67 (detected by Mib1), Cyclin A, B, D, E, p21CIP1, Geminin, PCNA (proliferating cell nuclear antigen), bcl-2, bax, bak, APAF-1, LYVE-1 (lymphatic vascular endothelial hyaluronan receptor-1), PTN, P-Cadherin, E-Cadherin, Beta-catenin, Integrins beta1 and beta3, MMPs (matrix metalloproteinases), Dysadherin, CEACAM1 (carcinoembryonic-antigen-related cell-adhesion molecule 1), Osteonectin, TA, Melastatin, ALCAM/CD166 (Activated leukocyte cell adhesion molecule), CXCR4, Metallothionein.

According to further embodiments n markers according to at least some embodiments of the present invention might optionally be used alone or in combination with one or more other compounds described herein, and/or in combination with known markers for prostate cancer, including but not limited to PSA, PAP (prostatic acid phosphatase), CPK-BB, PSMA, PCA3, DD3, and/or in combination with the known protein(s) for the variant marker as described herein.

According to further embodiments markers according to at least some embodiments of the present invention might optionally be used alone or in combination with one or more other compounds described herein, and/or in combination with known markers for pancreatic cancer, including but not limited to CA 19-9, and/or in combination with the known protein(s) for the variant marker as described herein.

According to further embodiments markers according to at least some embodiments of the present invention might optionally be used alone or in combination with one or more other compounds described herein, and/or in combination with known markers for hematological cancer, including but not limited to soluble forms of tumor markers like P-Selectin, CD-22, interleukins, cytokines, and/or in combination with the known protein(s) for the variant marker as described herein.

According to further embodiments markers according to at least some embodiments of the present invention might optionally be used alone or in combination with one or more other compounds described herein, and/or in combination with known markers for colon cancer, including but not limited to CEA, CA19-9, CA50, and/or in combination with the known proteins for the variant marker as described herein. The diagnostic assay is performed in a subject or in a sample obtained from a subject.

According to some embodiments, the sample taken from a subject to perform a diagnostic assay according to at least some embodiments of the present invention is selected from the group consisting of a body fluid or secretion including but not limited to blood, serum, urine, plasma, prostate fluid, seminal fluid, semen, the external secretions of the skin, respiratory, intestinal, and genitourinary tracts, tears, cerebrospinal fluid, sputum, saliva, milk, peritoneal fluid, pleural fluid, cyst fluid, secretions of the breast ductal system (and/or lavage thereof), broncho alveolar lavage, lavage of the reproductive system and lavage of any other part of the body or system in the body; samples of any organ including isolated cells or tissues, wherein the cell or tissue can be obtained from an organ selected from, but not limited to lung, colon, kidney, pancreas, ovary, prostate, liver, skin, bone marrow, lymph node, breast, and/or blood tissue; stool or a tissue sample, or any combination thereof. Prior to be subjected to the diagnostic assay, the sample can optionally be diluted with a suitable diluent. In certain embodiments, cells obtained from the sample are cultured in vitro prior to performing the diagnostic assay.

Numerous well known tissue or fluid collection methods can be utilized to collect the biological sample from a subject in order to determine the level of nucleic acid and/or polypeptide of the marker of interest in the subject.

Examples include, but are not limited to, fine needle biopsy, needle biopsy, core needle biopsy and surgical biopsy (e.g., brain biopsy), and lavage. Regardless of the procedure employed, once a biopsy/sample is obtained the level of the marker can be determined and a diagnosis can thus be made.

In at least some embodiments the present invention provides variant proteins, which may optionally be used as diagnostic markers, optionally as markers for in vivo imaging. According to at least some embodiments the present invention therefore overcomes the many deficiencies of the background art with regard to the need to obtain tissue samples and subjective interpretations of results. As in vivo imaging markers, the markers according to at least some embodiments of the present invention may also provide different and/or better measurement parameters for various diseases and/or pathological conditions. Molecular imaging using these markers could be performed in conjunction with other imaging modalities as CT and MRI which capture body anatomy and overlap it with the in-vivo marker distribution.

In at least some embodiments the present invention further relates to diagnostic assays for detecting a disease, particularly in a sample taken from a subject (patient), optionally a blood sample or a body secretion sample. In at least some embodiments of the present invention, the diagnostic assays are immunoassays, including, for example, immunohistochemical assay, radioimaging assays, in-vivo imaging, positron emission tomography (PET), single photon emission computer tomography (SPECT), magnetic resonance imaging (MRI), Ultra Sound, Optical Imaging, Computer Tomography, radioimmunoassay (RIA), ELISA, slot blot, competitive binding assays, fluorimetric imaging assays, Western blot, FACS, and the like. According to another embodiments, the diagnostic assays are NAT (nucleic acid amplification technology)-based assays, including, for example, nucleic acid hybridization assays, PCR or variations thereof, e.g. real-time PCR. The diagnostic assays can be qualitative or quantitative.

In some embodiments, the phrase "differentially present" refers to differences in the quantity of a marker present in a sample taken from subjects having one of the herein-described diseases or conditions as compared to a comparable sample taken from subjects who do not have one of the herein-described diseases or conditions. For example, a nucleic acid fragment may optionally be differentially present between the two samples if the amount of the nucleic acid fragment in one sample is significantly different from the amount of the nucleic acid fragment in the other sample, for example as measured by hybridization and/or NAT-based assays. A polypeptide is differentially present between the two samples if the amount of the polypeptide in one sample is significantly different from the amount of the polypeptide in the other sample. It should be noted that if the marker is detectable in one sample and not detectable in the other, then such a marker can be considered to be differentially present. Optionally, a relatively low amount of up-regulation may serve as the marker, as described herein. One of ordinary skill in the art could easily determine such relative levels of the markers; further guidance is provided in the description of each individual marker below.

The term "marker" in the context of the present invention refers to a nucleic acid fragment, a peptide, or a polypeptide, which is differentially present in a sample taken from subjects having one of the herein-described diseases or conditions, as compared to a comparable sample taken from subjects who do not have one the above-described diseases or conditions.

According to at least some embodiments of the present invention, a diagnostic assay can provide qualitative or quantitative information on the level of the markers in the sample.

In some embodiments, the phrase "qualitative" when in reference to differences in expression levels of a polynucleotide or polypeptide as described herein, refers to the presence versus absence of expression, or in some embodiments, the temporal regulation of expression, or in some embodiments, the timing of expression, or in some embodiments, any post-translational modifications to the expressed molecule, and others, as will be appreciated by one skilled in the art. In some embodiments, the phrase "quantitative" when in reference to differences in expression levels of a polynucleotide or polypeptide as described herein, refers to absolute differences in quantity of expression, as determined by any means, known in the art, or in other embodiments, relative differences, which may be statistically significant, or in some embodiments, when viewed as a whole or over a prolonged period of time, etc., indicate a trend in terms of differences in expression.

The term "level" refers to expression levels of nucleic acids (e.g. RNA) and/or polypeptides of the marker according to at least some embodiments of the present invention.

In certain embodiments, the diagnostic markers according to at least some embodiments of the invention are correlated to a condition or disease by their mere presence or absence. In other embodiments, threshold levels of the diagnostic markers can be established, and the level of the markers in a patient's sample can be compared to the threshold levels.

In some embodiments, the term "test amount" of a marker refers to an amount of a marker in a subject's sample that is consistent with a diagnosis of a particular disease or condition. A test amount can be either in absolute amount (e.g., microgram/ml) or a relative amount (e.g., relative intensity of signals).

In some embodiments, the term "control amount" of a marker can be any amount or a range of amounts to be compared against a test amount of a marker. For example, a control amount of a marker can be the amount of a marker in a patient with a particular disease or condition or a person without such a disease or condition. A control amount can be either in absolute amount (e.g., microgram/ml) or a relative amount (e.g., relative intensity of signals).

In some embodiments, the term "detect" refers to identifying the presence, absence or amount of the object to be detected.

In some embodiments, the term "label" includes any moiety or item detectable by spectroscopic, photo chemical, biochemical, immunochemical, or chemical means. For example, useful labels include 32P, 35S, fluorescent dyes, electron-dense reagents, enzymes (e.g., as commonly used in an ELISA), biotin-streptavadin, dioxigenin, haptens and proteins for which antisera or monoclonal antibodies are available, or nucleic acid molecules with a sequence complementary to a target. The label often generates a measurable signal, such as a radioactive, chromogenic, or fluorescent signal, that can be used to quantify the amount of bound label in a sample. The label can be incorporated in or attached to a primer or probe either covalently, or through ionic, van der Waals or hydrogen bonds, e.g., incorporation of radioactive nucleotides, or biotinylated nucleotides that are recognized by streptavadin. The label may be directly or indirectly detectable. Indirect detection can involve the binding of a second label to the first label, directly or indirectly. For example, the label can be the ligand of a binding partner, such as biotin, which is a binding partner for streptavadin, or a nucleotide sequence, which is the binding partner for a complementary sequence, to which it can specifically hybridize. The binding partner may itself be directly detectable, for example, an antibody may be itself labeled with a fluorescent molecule. The binding partner also may be indirectly detectable, for example, a nucleic acid having a complementary nucleotide sequence can be a part of a branched DNA molecule that is in turn detectable through hybridization with other labeled nucleic acid molecules (see, e.g., P. D. Fahrlander and A. Klausner, Bio/Technology 6:1165 (1988)). Quantitation of the signal is achieved by, e.g., scintillation counting, densitometry, or flow cytometry.

Exemplary detectable labels, optionally for use with immunoassays, include but are not limited to magnetic beads, fluorescent dyes, radiolabels, enzymes (e.g., horse radish peroxide, alkaline phosphatase and others commonly used in an ELISA), and calorimetric labels such as colloidal gold or colored glass or plastic beads. Alternatively, the marker in the sample can be detected using an indirect assay, wherein, for example, a second, labeled antibody is used to detect bound marker-specific antibody, and/or in a competition or inhibition assay wherein, for example, a monoclonal antibody which binds to a distinct epitope of the marker are incubated simultaneously with the mixture.

The phrase "specifically (or selectively) binds" to an antibody or "specifically (or selectively) immunoreactive with," or "specifically interacts or binds" when referring to a protein or peptide (or other epitope), refers, in some embodiments, to a binding reaction that is determinative of the presence of the protein in a heterogeneous population of proteins and other biologics. Thus, under designated immunoassay conditions, the specified antibodies bind to a particular protein at least two times greater than the background (non-specific signal) and do not substantially bind in a significant amount to other proteins present in the sample. Specific binding to an antibody under such conditions may require an antibody that is selected for its specificity for a particular protein. For example, polyclonal antibodies raised to seminal basic protein from specific species such as rat, mouse, or human can be selected to obtain only those polyclonal antibodies that are specifically immunoreactive with seminal basic protein and not with other proteins, except for polymorphic variants and alleles of seminal basic protein. This selection may be achieved by subtracting out antibodies that cross-react with seminal basic protein molecules from other species. A variety of immunoassay formats may be used to select antibodies specifically immunoreactive with a particular protein. For example, solid-phase ELISA immunoassays are routinely used to select antibodies specifically immunoreactive with a protein (see, e.g., Harlow & Lane, Antibodies, A Laboratory Manual (1988), for a description of immunoassay formats and conditions that can be used to determine specific immunoreactivity). Typically a specific or selective reaction will be at least twice background signal or noise and more typically more than 10 to 100 times background. Diagnostic assays according to at least some embodiments of the present invention include, but are not limited to immunoassays and nucleic acid based assays "Immunoassay" is an assay that uses an antibody to specifically bind an antigen. The immunoassay is characterized by the use of specific binding properties of a particular antibody to isolate, target, and/or quantify the antigen.

According to at least some embodiments, the present invention provides a method for detecting the polypeptides according to at least some embodiments of the invention in a biological sample, comprising: contacting a biological sample with an antibody specifically recognizing a polypeptide according to at least some embodiments of the present invention and detecting said interaction; wherein the presence of an interaction correlates with the presence of a polypeptide in the biological sample.

According to at least some embodiments, the present invention provides a method for detecting a polynucleotide according to at least some embodiments of the invention in a biological sample, using NAT based assays, comprising: hybridizing the isolated nucleic acid molecules or oligonucleotide fragments of at least about a minimum length to a nucleic acid material of a biological sample and detecting a hybridization complex; wherein the presence of a hybridization complex correlates with the presence of the polynucleotide in the biological sample.

Non-limiting examples of methods or assays are described below.

The present invention also relates to kits based upon such diagnostic methods or assays.

Immunoassays

Immunological binding assays include, for example, an enzyme immune assay (EIA) such as enzyme-linked immunosorbent assay (ELISA), a radioimmune assay (RIA), a Western blot assay, or a slot blot assay (see, e.g., U.S. Pat. Nos. 4,366,241; 4,376,110; 4,517,288; and 4,837,168). Generally, a subject or a sample obtained from a subject is contacted with an antibody that specifically binds a polypeptide according to at least some embodiments of the invention, or a fragment thereof. Optionally, the antibody can be fixed to a solid support prior to contacting the antibody with a sample. Examples of solid supports include but are not limited to glass or plastic in the form of, e.g., a microtiter plate, a stick, a bead, or a microbead. After incubating the sample with antibodies, the mixture is washed and the antibody-marker complex formed can be detected. This can be accomplished by incubating the washed mixture with a detection reagent. Alternatively, the marker in the sample can be detected using an indirect assay, wherein, for example, a second, labeled antibody is used to detect bound marker-specific antibody. Throughout the assays, incubation and/or washing steps may be required after each combination of reagents. Incubation steps can vary from about 5 seconds to several hours, preferably from about 5 minutes to about 24 hours. However, the incubation time will depend upon the assay format, marker, volume, concentrations and the like. Usually the assays will be carried out at ambient temperature, although they can be conducted over a range of temperatures, such as 10° C. to 40° C.

The amount of an antibody-marker complex can optionally be determined by comparing to a standard or to a control amount and/or signal.

Radio-immunoassay (RIA): According to one embodiment, this method involves contacting the biological sample with a specific antibody followed by a radiolabeled secondary antibody or antibody binding protein (e.g., protein A labeled with 1125) immobilized on a precipitable carrier such as agarose beads. The number of counts in the precipitated pellet is proportional to the amount of the marker polypeptide in the sample.

Enzyme linked immunosorbent assay (ELISA): This method involves fixation of a sample containing the target polypeptide to a surface such as a well of a microtiter plate. A substrate specific antibody coupled to an enzyme is applied and allowed to bind to the target polypeptide. Presence of the antibody is then detected and quantitated by a colorimetric reaction employing the enzyme coupled to the antibody. Enzymes commonly employed in this method include horseradish peroxidase and alkaline phosphatase. The amount of substrate present in the sample is proportional to the amount of color produced. A substrate standard is generally employed to improve quantitative accuracy.

Western blot: This method involves separation of a solution containing the target polypeptide by means of an acrylamide gel followed by transfer of the polypeptides to a membrane (e.g., nylon or PVDF). Presence of the target polypeptide is then detected by specific antibodies, which are in turn detected by antibody binding reagents. Antibody binding reagents may be, for example, protein A, or secondary antibodies. Antibody binding reagents may be radiolabeled or enzyme linked as described hereinabove. Detection may be by autoradiography, colorimetric reaction or chemiluminescence. This method allows both quantitative analysis of the amount of target polypeptide and determination of its identity by a relative position on the membrane which is indicative of a migration distance in the acrylamide gel during electrophoresis.

Immunohistochemical analysis: This method involves detection of a substrate in situ in fixed cells by specific antibodies. The antibodies may be enzyme linked or linked to fluorophores. Detection is by microscopy and subjective evaluation. If enzyme linked antibodies are employed, a colorimetric reaction may be required.

Fluorescence activated cell sorting (FACS): This method involves detection of a target polypeptide in situ in cells by specific antibodies. The antibodies are linked to fluorophores. Detection is by means of a cell sorting machine which reads the wavelength of light emitted from each cell as it passes through a light beam. This method may employ two or more antibodies simultaneously.

Nucleic Acid Technology (Nat) Based Assays:

According to at least some embodiments the invention also contemplates nucleic acids which selectively hybridize with the polynucleotides according to at least some embodiments of the invention. The following are non-limiting examples of Nucleic Acid Technology-based assays: polymerase chain reaction (PCR), Real-Time PCR, ligase chain reaction (LCR), Self-Sustained Synthetic Reaction, Q-Beta Replicase, Cycling probe reaction, Branched DNA, RFLP analysis, DGGE/TGGE, Single-Strand Conformation Polymorphism, Dideoxy fingerprinting, microarrays, Fluorescense In Situ Hybridization and Comparative Genomic Hybridization. Detection of a nucleic acid of interest in a biological sample may be effected by assays which involve nucleic acid amplification technology Amplification of a target nucleic acid sequence may be carried out by a number of suitable methods known in the art. Non-limiting examples of amplification techniques include primer based-PCR, LCR, strand displacement amplification (SDA), transcription-based amplification, the q3 replicase system and NASBA (Kwoh et al., 1989, Proc. Natl. Acad. Sci. USA 86, 1173-1177; Lizardi et al., 1988, BioTechnology 6:1197-1202; Malek et al., 1994, Methods Mol. Biol., 28:253-260; and Sambrook et al., 1989, supra). As used herein, a "primer" refers to an oligonucleotide which is capable of annealing to (hybridizing with) a target sequence, thereby creating a double stranded region which can serve as an initiation point for DNA synthesis under suitable conditions. The terminology "amplification pair" (or "primer pair") refers herein to a pair of oligonucleotides (oligos), which are selected to be used together in amplifying a selected nucleic acid sequence by one of a number of types of amplification processes, preferably a polymerase chain reaction.

Oligonucleotide primers according to at least some embodiments of the present invention may be of any suitable length, depending on the particular assay format and the particular needs and targeted genomes employed. Optionally, the oligonucleotide primers are at least 12 nucleotides in length, preferably between 15 and 24 nucleotides, and they may be adapted to be especially suited to a chosen nucleic acid amplification system. As commonly known in the art, the oligonucleotide primers can be designed by taking into consideration the melting point of hybridization thereof with its targeted sequence (Sambrook et al., 1989, Molecular Cloning—A Laboratory Manual, 2nd Edition, CSH Laboratories; Ausubel et al., 1989, in Current Protocols in Molecular Biology, John Wiley & Sons Inc., N.Y.).

Radio-Imaging Methods

These methods include but are not limited to, positron emission tomography (PET) and single photon emission computed tomography (SPECT). Both of these techniques are non-invasive, and can be used to detect and/or measure a wide variety of tissue events and/or functions, such as detecting cancerous cells for example. Unlike PET, SPECT can optionally be used with two labels simultaneously. SPECT has some other advantages as well, for example with regard to cost and the types of labels that can be used. For example, U.S. Pat. No. 6,696,686 describes the use of SPECT for detection of breast cancer.

According to at least some embodiments the present invention also relates to kits based upon such diagnostic methods or assays.

Theranostics:

According to at least some embodiments the present invention also relates to the ude of markers and antibodies according to at least some embodiments of the invention for theranostics. The term theranostics describes the use of diagnostic testing to diagnose the disease, choose the correct treatment regime according to the results of diagnostic testing and/or monitor the patient response to therapy according to the results of diagnostic testing. Theranostic tests optionally may be used to select patients for treatments that are particularly likely to benefit them and unlikely to produce side-effects. They can also provide an early and objective indication of treatment efficacy in individual patients, so that (if necessary) the treatment can be altered with a minimum of delay. For example: DAKO and Genentech together created HercepTest and Herceptin (trastuzumab) for the treatment of breast cancer, the first theranostic test approved simultaneously with a new therapeutic drug. In addition to HercepTest (which is an immunohistochemical test), other theranostic tests are in development which use traditional clinical chemistry, immunoassay, cell-based technologies and nucleic acid tests. PPGx's recently launched TPMT (thiopurine S-methyltransferase) test, which is enabling doctors to identify patients at risk for potentially fatal adverse reactions to 6-mercaptopurine, an agent used in the treatment of leukemia. Also, Nova Molecular pioneered SNP genotyping of the apolipoprotein E gene to predict Alzheimer's disease patients' responses to cholinomimetic therapies and it is now widely used in clinical trials of new drugs for this indication. Thus, the field of theranostics represents the intersection of diagnostic testing information that predicts the response of a patient to a treatment with the selection of the appropriate treatment for that particular patient.

Surrogate Markers:

According to at least some embodiments the present invention also relates to the ude of markers and antibodies according to at least some embodiments of the invention as Surrogate markers. A surrogate marker is a marker, that is detectable in a laboratory and/or according to a physical sign or symptom on the patient, and that is used in therapeutic trials as a substitute for a clinically meaningful endpoint. The surrogate marker is a direct measure of how a patient feels, functions, or survives which is expected to predict the effect of the therapy. The need for surrogate markers mainly arises when such markers can be measured earlier, more conveniently, or more frequently than the endpoints of interest in terms of the effect of a treatment on a patient, which are referred to as the clinical endpoints. Ideally, a surrogate marker will be biologically plausible, predictive of disease progression and measurable by standardized assays (including but not limited to traditional clinical chemistry, immunoassay, cell-based technologies, nucleic acid tests and imaging modalities).

Surrogate endpoints were used first mainly in the cardiovascular area. For example, antihypertensive drugs have been approved based on their effectiveness in lowering blood pressure. Similarly, in the past, cholesterol-lowering agents have been approved based on their ability to decrease serum cholesterol, not on the direct evidence that they decrease mortality from atherosclerotic heart disease. The measurement of cholesterol levels is now an accepted surrogate marker of atherosclerosis. In addition, currently two commonly used surrogate markers in HIV studies are CD4+ T cell counts and quantitative plasma HIV RNA (viral load). In some embodiments of this invention, the polypeptide/polynucleotide expression pattern may serve as a surrogate marker for a particular disease, as will be appreciated by one skilled in the art.

EXAMPLE 8

Small Interfering Nucleic Acids and Antisense Molecules According to at Least Some Embodiments of the Present Invention According to at least some embodiments the present invention further relates to small interfering nucleic acids, in particular siNA comprising complementary sequences capable of specifically hybridizing with the polynucleotides according to at least some embodiments of the invention and specifically silencing these genes. According to at least some embodiments the present invention also relates to sequences and constructs encoding such nucleic acids and to the uses of such nucleic acids or constructs to modify gene expression, particularly to reduce or inhibit gene expression.

Certain single stranded nucleic acid molecules are able to form a self-complementary double stranded region where part of the nucleotide sequence is able to interact with another part of the sequence by Watson-Crick base pairing between inverted repeats of the sequence. Where the repeated regions are adjacent or in close proximity to each other, the double stranded regions may form structures known as hairpin structures. The hairpin structure forms with an unpaired "loop" of nucleotides at one end of the hairpin structure, with the inverted repeat sequence annealed. The loop may also facilitate the folding of the nucleic acid chain.

Hairpin RNA sequences have been used in interfering RNA and gene silencing technologies. Such techniques are described for example in U.S. Pat. No. 6,573,099 and in Grimm D. (Adv. Drug Deliv. Rev. 2009 61 (9): 672-703). According to at least some embodiments the present invention further contemplates antisense RNA molecules complementary to the polynucleotides according to at least some embodiments of the invention, or to any fragment thereof. Antisense RNA may be introduced into a cell to inhibit translation of the complementary mRNA by hybridizing with the polynucleotides of the according to at least some embodiments of the invention and obstructing the translation machinery.

siNA or antisense molecules according to at least some embodiments of the invention may be used as a therapeutic tool to inhibit gene expression in vivo.

The descriptions given are intended to exemplify, but not limit, the scope of the invention. The invention is now further described by the claims which follow.

What is claimed is:

1. A monoclonal or polyclonal antibody comprising an antigen binding site that binds specifically to T5, with SEQ ID NO: 1, polypeptide, wherein said antibody binds to the known, wild type heparanase protein with a binding affinity that is at least 5 times lower than a binding affinity to T5, with SEQ ID NO: 1, wherein the antibody is secreted by 9c9 hybridoma deposited according to the provisions of the Budapest Treaty with the Health Protection Agency Culture Collections (Centre for Emergency Preparedness & Response, Porton Down, Salisbury SP4 OJG, United Kingdom), having a Accession Number: 10111101.

2. A pharmaceutical composition, comprising the antibody of claim 1, and a pharmaceutically acceptable carrier.

3. A method of treating a subject suffering from a disorder characterized by the presence of tumor cells expressing T5, by administering to the subject a therapeutically effective amount of the antibody of claim 1.

* * * * *